(12) United States Patent
Brown et al.

(10) Patent No.: US 6,455,520 B1
(45) Date of Patent: Sep. 24, 2002

(54) BENZAMIDE DERIVATIVES AND THEIR USE AS CYTOKINE INHIBITORS

(75) Inventors: Dearg S Brown; George R Brown, both of Macclesfield (GB)

(73) Assignee: Astra Zeneca AB, Sodertalje (SE)

( * ) Notice: Subject to any disclaimer, the term of this patent is extended or adjusted under 35 U.S.C. 154(b) by 0 days.

(21) Appl. No.: 09/787,882

(22) PCT Filed: Sep. 21, 1999

(86) PCT No.: PCT/GB99/03144

§ 371 (c)(1),
(2), (4) Date: Mar. 23, 2001

(87) PCT Pub. No.: WO00/18738

PCT Pub. Date: Apr. 6, 2000

(30) Foreign Application Priority Data

Sep. 25, 1998 (GB) ............................................. 9820770
Dec. 9, 1998 (GB) ............................................. 9826938
Mar. 17, 1999 (GB) ............................................. 9905969

(51) Int. Cl.$^7$ .................. A61K 31/496; A61K 31/5377; C07D 401/04; C07D 403/02; C07D 413/14
(52) U.S. Cl. .................... 514/212; 514/218; 514/231.8; 514/235.5; 514/239.5; 514/252; 514/311; 514/314; 514/343; 514/354; 514/448; 514/461; 540/575; 540/598; 544/82; 544/121; 544/124; 544/131; 544/146; 544/362; 544/363; 544/364; 544/365; 544/366; 544/367; 544/371; 544/376; 544/378; 544/379; 546/176; 546/276.4; 546/323; 549/72; 549/487
(58) Field of Search .................................. 540/575, 598; 544/82, 121, 124, 131, 146, 362, 363, 364, 365, 366, 367, 371, 376, 378, 379; 546/176, 276.4, 323; 549/72, 487; 514/212, 218, 231.8, 235.5, 239.5, 252, 311, 314, 343, 354, 448, 461

(56) References Cited

U.S. PATENT DOCUMENTS

| | | | |
|---|---|---|---|
| 1,903,899 A | 4/1933 | Laska et al. | 564/139 |
| 1,909,960 A | 5/1933 | Hitch | 564/140 |
| 3,211,555 A | 10/1965 | Mory et al. | 96/99 |
| 3,755,332 A | 8/1973 | Wasley et al. | 260/288 |
| 4,524,168 A | 6/1985 | Wick | 524/190 |
| 4,749,729 A | 6/1988 | Kohli et al. | 523/468 |

FOREIGN PATENT DOCUMENTS

| | | |
|---|---|---|
| DE | 522 788 | 3/1931 |
| DE | 28 12 252 | 10/1979 |
| EP | 0 635 507 | 1/1995 |
| EP | 0 849 256 A1 | 6/1998 |
| WO | WO 93/04170 | 3/1993 |
| WO | WO 95/19774 | 7/1995 |
| WO | WO 97/05878 | 2/1997 |
| WO | WO 97/13771 | 4/1997 |
| WO | WO 97/32853 | 9/1997 |
| WO | WO 98/06715 | 2/1998 |
| WO | WO 98/22103 | 5/1998 |
| WO | WO 99/15164 | 4/1999 |
| WO | WO 99/59959 | 11/1999 |
| WO | WO 99/59960 | 11/1999 |
| WO | WO 00/07980 | 2/2000 |
| WO | WO 00/07991 | 2/2000 |
| WO | WO 00/18738 | 4/2000 |
| WO | WO 00/20402 | 4/2000 |
| WO | WO 00/55120 | 9/2000 |
| WO | WO 00/55153 | 9/2000 |
| WO | WO 00/56738 | 9/2000 |
| WO | WO 01/27089 | 4/2001 |

OTHER PUBLICATIONS

Adams et al., "Search for trypanocides. III. Analogs of suramin.", Chemical Abstracts, vol. 51, 1957, columns 5068 and 5069.

Ando et al., "Producing azo lake pigments"; Chemical Abstract, vol. 106, Abstract No., 215574, 1987.

Ando et al., Magn. Reson.Chem. 33(8) 639–45, 1995, Chemical Abstract: 123: 227514, 1995.

Beilstein Reg. No. 2164595.

Beilstein Reg. No. 3166971.

(List continued on next page.)

Primary Examiner—Fiona T. Powers
(74) Attorney, Agent, or Firm—Morgan, Lewis & Bockius LLP

(57) ABSTRACT

The invention concerns amide derivatives of formula (I)

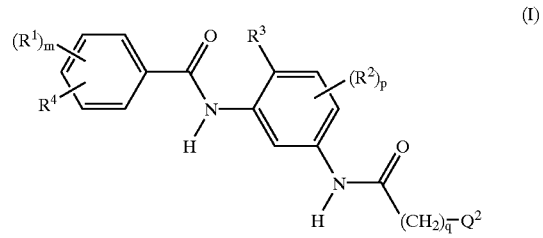

(I)

wherein $R^3$ is (1–6C)alkyl or halogeno; m is 0–3, p is 0–2 and q is 0–4; each of $R^1$ and $R^2$ is a group such as hydroxy, halogeno, trifluoromethyl and cyano; $R^4$ is a basic group such as amino, (1–6C)alkylamino, di-[(1–6C)alkyl]amino, di-[(1–6C)alkyl]amino-(1–6C)alkyl, di-[(1–6C)alkyl]amino-(2–6C)alkoxy, heteroaryl, heteroaryloxy, heteroaryl-(1–6C)alkoxy, heterocyclyl, heterocyclyloxy and heterocyclyl-(1–6C)alkoxy; and $Q^2$ is a group such as heteroaryl, heteroaryloxy or heteroaryl-(1–6C)alkoxy which is optionally substituted; or pharmaceutically-acceptable salts or in-vivo-cleavable esters thereof; processes for their preparation, pharmaceutical compositions containing them and their use in the treatment of diseases or medical conditions mediated by cytokines.

13 Claims, No Drawings

OTHER PUBLICATIONS

Beilstein Reg. No. 3451759.

Beilstein Reg. No. 3480574.

Beilstein Reg. No. 3483669.

Beilstein Reg. No. 3534091.

Chemical Abstract No. 12076g, vol. 65, 1966.

Chemical Abstract No. 12932a, vol. 51, 1957.

Denny et al., "Potential Antitumour Agents. 29. Quantitative Structure–Activity Relationships for the Antileukemic Bisquaternary Ammonium Heterocycles", Journal of Medicinal Chemistry, Feb. 1979, vol. 22, No. 2, pp. 134–150.

Hamuro et al., "Novel Folding Patterns in a Family of Oligoanthranilamides: . . . Secondary Structures", J. Amer. Chem. Soc., 1997, pp. 10587–10593.

Ito et al., Photosensitive material containing microencapsulated hydrazine derivatives; Chemical Abstract, vol. 118, Abstract No. 70021, 1993.

Kelly et al., "Antirhinorvirus Activity of 6–Anilino–9–benxyl–2–chloro–9H–purines", J. Med. Chem., 1990, vol. 33, pp. 1360–1363, XP–002140324.

Lesiak, "New amides of pyrrole–N– and indole–N–caboxylic acids", Chemical Abstracts, No. 76:126704, 1972.

Mühlbach, "Pyrazoles—A Novel Class of Blocking Agents for Isocyanates", Journal of Polymer Science: Part A: Polymer Chemistry, vol. 32, Mar. 1994, pp. 753–765.

Myers et al., "The Preparation and SAR of 4–(Anilino), 4–(Phenoxy), and 4–(Thiophenoxy)–Quinazoline: Inhibitors of P56$^{lck}$ and EGF–R Tyrosine Kinase Activity"; Bioorganic & Medicinal Chemistery Letters, vol. 7, No. 4, pp. 417–420.

Petrova et al., "Determination of the Structure of the Oxidative . . . by Spectroscopic Methods", Journal of Molecular Structure, vol. 142, 1986, pp. 459–462.

Sugawara et al., Kogyo Kaguku Zasshi 72(11) 2425–2429, 1969, Chemical Abstract: 72:66514, 1970.

Thompson et al., "Tyrosine Kinase Inhibitors. 7.7–Amino–4–(phenylamino– and 7–Amino–4–[(phenylmethyl)amino]purido[4,3–d]pyrimidines: A New Class of Inhibitors of the Tyrosine Kinase Activity of the Epidermal Growth Factor Receptor"; Journal of Medicinal Chemistry, US, American Chemical Society, vol. 38, No. 19, 1995, pp. 3780–3788, XP002140323.

Wang et al., "Low–valent Titanium–induced Reactions of Substituted Nitrobenzenes", J. Chem. Research, 1998, pp. 182–183.

M.J. Ashton et al: "New Low–Density Lipoprotein Upregulators Acting via a Novel Mechanism." Journal of Medicinal Chemistry, vol. 39, No. 17, Aug. 16, 1996, pp. 3342–3356, XP002086153, whole article.

G.J. Hanson et al: "Inhibitors of p38 kinase" Expert Opinion on Therapeutic patents, vol. 7, No. 7, 1997, pp. 729–733, XP002086152 cited in the application whole document.

Database WPI, Week 9730 Derwent Publications Ltd., London, GB; AN 323139 XP002086154 & JP 09 124571 A (Japan Tobacco Inc.), May 13, 1997, abstract, examples 175–192.

BENZAMIDE DERIVATIVES AND THEIR USE AS CYTOKINE INHIBITORS

This application is the national phase of international application PCT/GB99/03144 filed Sep. 21, 1999 which designated the U.S. and that application was published under PCT Article 21(2) in English.

This invention concerns certain amide derivatives which are useful as inhibitors of cytokine mediated disease. The invention also concerns processes for the manufacture of the amide derivatives of the invention, pharmaceutical compositions containing them and their use in therapeutic methods. for example by virtue of inhibition of cytokine mediated disease.

The amide derivatives disclosed in the present invention are inhibitors of the production of cytokines such as Tumour Necrosis Factor (hereinafter TNF), for example TNFα. and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other. cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in,the production and development of disease states such as inflammatory and allergic diseases, for example inflammation of the joints (especially rheumatoid arthritis, osteoarhritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis and adult respiratory distress syndrome), and in the production and development of various cardiovascular and cerebrovascular disorders such as congestive heart disease, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock sydrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet,* 1994, 344, 1125 and *British Journal of Rheumatology,* 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase. otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents,* 1997,7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

According to one aspect of the present invention there is provided a compound of the Formula I

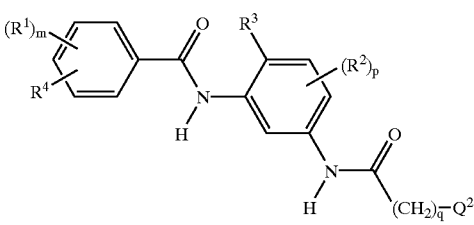

wherein
$R^3$ is (1–6C)alkyl or halogeno;
m is 0, 1, 2 or 3;
$R^1$ is hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)

alkylamino, di-[(1–6C)alkyl]amino, (1–6C) alkoxycarbonyl, N-(1–6C)alkylcarbamoyl, N,N-di-[(1–6C)alkyl]carbamoyl, (2–6C)alkanoyl, (2–6C) alkanoyloxy, (1–6C)alkanoylamino, N-(1–6C) alkylsulphamoyl, N,N-di-[(1–6C)alkyl]sulphamoyl, (1–6C)alkanesulphonylamino, N-(1–6C)alkyl-(1–6C) alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C) alkylamino-(1–6C)alkyl, di-[(1–6C)alkyl]amino-(1–6C)alkyl, carboxy-(1–6C)alkyl, (1–6C) alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C) alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C) alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C) alkylamino, (1–6C)alkoxy-(2–6C)alkylamino, cyano (1–6C)alkylamino, carboxy-(1–6C)alkylamino, (1–6C) alkoxycarbonyl-(1–6C)alkylamino, carbamoyl-(1–6C) alkylamino, N-(1–6C)alkylcarbamoyl-(1–6C) alkylamino, N,N-di-[(1–6C)alkyl]carbamoyl-(1–6C) alkylamino, amino-(2–6C)alkylamino, (1–6C) alkylamino-(2–6C)alkylamino, di-[(1–6C)alkyl] amino-(2–6C)alkylamino, N-(1–6C)alkyl-halogeno-(1–6C)alkylamino, N-(1–6C)alkyl-hydroxy-(2–6C) alkylamino, N-(1–6C)alkyl-(1–6C)alkoxy-(2–6C) alkylamino, N-(1–6C)alkyl-cyano-(1–6C)alkylamino, N-(1–6C)alkyl-carboxy-(1–6C)alkylamino, N-(1–6C) alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C) alkylamino, N-(1–6C)alkyl-N,N-di-[(1–6C)alkyl] carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl] amino-(2–6C)alkylamino, halogeno-(2–6C) alkanoylamino, hydroxy-(2–6C)alkanoylamino, (1–6C)alkoxy-(2–6C)alkanoylamino, cyano-(2–6C) alkanoylamino, carboxy-(2–6C)alkanoylamino, (1–6C)alkoxycarbonyl-(2–6C)alkanoylamino, carbamoyl-(2–6C)alkanoylamino, N-(1–6C) alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino or di-[(1–6C)alkyl]amino-(2–6C)alkanoylamino, or $R^1$ is aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C) alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C) alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C) alkanoylamino, heterocyclyl, heterocyclyl-(1–6C) alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl or heterocyclyl-(2–6C) alkanoylamino, and wherein any aryl, heteroaryl or heterocyclyl group in a $R^1$ substituent may optionally bear 1 or 2 substituents selected from hydroxy, halogeno, (1–6C)alkyl, (1–6C)alkoxy, carboxy, (1–6C) alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl] amino-(1–6C)alkyl, aryl and aryl-(1–6C)alkyl;

p is 0, 1 or 2;

$R^1$ is hydroxy, halogeno, trifluoromethyl, cyano, mercapto, nitro, amino, carboxy, (1–6C) alkoxycarbonyl; (1–6C)alkyl, (2–6C)alkenyl, (2–6C) alkynyl, (1–6C)alkoxy, (1–6C)alkylamino or di-[(1–6C)alkyl]amino;

$R^4$ is amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C) alkoxy, (1–6C)alkylamino-(2–6C)alkoxy, di-[(1–6C) alkyl]amino-(2–6C)alkoxy, amino-(2–6C)alkylamino, (1–6C)alkylamino-(2–6C)alkylamino, di-[(1–6C) alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl] amino-(2–6C)alkylamino, amino-(2–6C) alkanoylamino, (1–6C)alkylamino-(2–6C) alkanoylamino or di-[(1–6C)alkyl]amino-(2–6C) alkanoylamino, or $R^4$ is heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C) alkanoylamino, heteroaryl-(1–6C)alkoxy-(1–6C)alkyl, heteroaryl-(1–6C)alkylamino-(1–6C)alkyl, N-(1–6C) alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C) alkanoylamino, heterocyclyl-(1–6C)alkoxy-(1–6C) alkyl, heterocyclyl-(1–6C)alkylamino-(1–6C)alkyl or N-(1–6C)alkyl-heterocyclyl-(1–6C)alkylamino-(1–6C) alkyl, and wherein any of the $R^4$ substituents defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a $R^4$ substituent may optionally bear 1 or 2 substituents selected from hydroxy, halogeno, (1–6C)alkyl, (1–6C) alkoxy, carboxy, (1–6C)alkoxycarbonyl, N-(1–6C) alkylcarbamoyl, N,N-di-[(1–6C)alkyl]carbamoyl, (2–6C)

alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

q is 0, 1, 2, 3 or 4; and $Q^2$ is heteroaryl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl or heteroaryl-(2–6C)alkanoylamino and $Q^2$ is optionally substituted with 1, 2 or 3 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl and N-(1–6C)alkyl-heterocyclyl-(1–6C)alkylamino-(1–6C)alkyl, and wherein any of the substituents on $Q^2$ defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a substituent on $Q^2$ may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

or a pharmaceutically-acceptable salt or in-vivo-cleavable ester thereof.

According to a further aspect of the present invention there is provided a compound of the Formula I wherein $R^3$ is (1–6C)alkyl or halogeno;

m is 0, 1, 2 or 3;

$R^1$ is hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)

alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino or di-[(1–6C)alkyl]amino-(2–6C)alkanoylamino, or $R^1$ is aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–14 6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl or heterocyclyl-(2–6C)alkanoylamino, and wherein any aryl, heteroaryl or heterocyclyl group in a $R^1$ substituent may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino and di-[(1–6C)alkyl]amino;

p is 0, 1 or 2;

$R^2$ is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino;

$R^4$ is amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl -(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino or di-[(1–6C)alkyl]amino-(2–6C)alkanoylamino, or $R^4$ is heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl or heterocyclyl-(2–6C)alkanoylamino, and wherein any aryl, heteroaryl or heterocyclyl group in a $R^4$ substituent may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino and di-[(1–6C)alkyl]amino;

q is 0, 1, 2, 3 or 4; and $Q^2$ is heteroaryl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl or heteroaryl-(2–6C)alkanoylamino and $Q^2$ is optionally substituted with 1, 2 or 3 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)

alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C) alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C) alkylamino, (1–6C)alkoxy-(2–6C)alkylamino, cyano-(1–6C)alkylamino, carboxy-(1–6C)alkylamino, (1–6C) alkoxycarbonyl-(1–6C)alkylamino, carbamoyl-(1–6C) alkylamino, N-(1–6C)alkylcarbamoyl-(1–6C) alkylamino, N,N-di-[(1–6C)alkyl]carbamoyl-(1–6C) alkylamino, amino-(2–6C)alkylamino, (1–6C) alkylamino-(2–6C)alkylamino, di-[(1–6C)alkyl] amino-(2–6C)alkylamino, N-(–6C)alkyl-halogeno-(1–6C)alkylamino, N-(1–6C)alkyl-hydroxy-(2–6C) alkylamino, N-(1–6C)alkyl-(1–6C)alkoxy-(2–6C) alkylamino, N-(1–6C)alkyl-cyano-(1–6C)alkylamino, N-(1–6C)alkyl-carboxy-(1–6C)alkylamino, N-(1–6C) alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C) alkylamino, N-(1–6C)alkyl-N,N-di-[(1–6C)alkyl] carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl] amino-(2–6C)alkylamino, halogeno-(2–6C) alkanoylamino, hydroxy-(2–6C)alkanoylamino, (1–6C)alkoxy-(2–6C)alkanoylamino, cyano-(2–6C) alkanoylamino, carboxy-(2–6C)alkanoylamino, (1–6C)alkoxycarbonyl-(2–6C)alkanoylamino, carbamoyl-(2–6C)alkanoylamino, N-(1–6C) alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C) alkanoylamino, aryl, aryl-(1–6C)alkyl, aryl-(1–6C) alkoxy, aryloxy, arylamino, N-(1–6C)alkyl-arylamino, aryl-(1–6C)alkylamino, N-(1–6C)alkyl-aryl-(1–6C) alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C) alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C) alkanoylamino, heterocyclyl, heterocyclyl-(1–6C) alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C) alkanoylamino, and wherein any aryl, heteroaryl or heterocyclyl group in a substituent on $Q^2$ may optionally bear 1 or 2 substituents selected from hydroxy, halogeno, (1–6C)alkyl, (1–6C)alkoxy, carboxy, (1–6C) alkoxycarbonyl, N-(1–6C)alkylcarbamoyl, N,N-di-[(1–6C)alkyl]carbamoyl, (2–6C)alkanoyl, amino, (1–6C)alkylamino and di-[(1–6C)alkyl]amino;
or a pharmaceutically-acceptable salt or in-vivo-cleavable ester thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for $R^1$ or for a substituent on $Q^2$ when it is aryl or for the aryl group within a $R^1$ substituent or within a substituent on $Q^2$ is, for example, phenyl or naphthyl, preferably phenyl.

A suitable value for $R^1$, $R^4$ or $Q^2$ when it is heteroaryl, for the heteroaryl group within a $R^1$ or $R^4$ substituent or $Q^2$ group, for a substituent on $Q^2$ when it is heteroaryl or for the heteroaryl group within a substituent on $Q^2$ is, for example, an aromatic 5- or 6-membered monocyclic ring, a 9- or 10-membered bicyclic ring or a 13- or 14-membered tricyclic ring each with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3, 5-triazenyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl, more preferably furyl, thienyl, isoxazolyl, thiazolyl, pyridyl, benzothiophenyl, benzofurazanyl, quinolyl, carbazolyl, dibenzofuranyl or dibenzothiophenyl.

A suitable value for $R^1$ or $R^4$ or for a substituent on $R^4$ or $Q^2$ when it is heterocyclyl or for the heterocyclyl group within a $R^1$ or $R^4$ substituent or within a substituent on $Q^2$ is, for example, a non-aromatic saturated or partially saturated 5- to 10-membered monocyclic or bicyclic ring with up to five heteroatoms selected from oxygen, nitrogen and sulphur, for example pyrrolinyl, pyrrolidinyl, morpholinyl, piperidinyl, homopiperidinyl, piperazinyl, homopiperazinyl, dihydropyridinyl, tetrahydropyridinyl, dihydropyrimidinyl or tetrahydropyrimidinyl, preferably pyrrolidin-1-yl, pyrrolidin-2-yl, morpholino, piperidino, piperazin-1-yl or homopiperazin-1-yl.

Suitable values for various $R^1$, $R^2$, $R^3$ or $R^4$ groups, or for various substituents on $R^4$ or $Q^2$ or on an aryl, heteroaryl or heterocyclyl group within $R^1$ or $R^4$ or on an aryl, heteroaryl or heterocyclyl group on a substituent on $Q^2$ include:

for halogeno: fluoro, chloro, bromo and iodo;

for (1–6C)alkyl: methyl, ethyl, propyl, isopropyl and tert-butyl;

for (2–6C)alkenyl: vinyl and allyl;

for (2–6C)alkynyl: ethynyl and 2-propynyl;

for (1–6C)alkoxy: methoxy, ethoxy, propoxy, isopropoxy and butoxy;

for (1–6C)alkoxycarbonyl: methoxycarbonyl, ethoxycarbonyl, propoxycarbonyl and tert-butoxycarbonyl;

for N-(1–6C)alkylcarbamoyl: N-methylcarbamoyl, N-ethylcarbamoyl and N-propylcarbamoyl;

for N,N-di-[(1–6C)alkyl]carbamoyl: N N-dimethylcarbamoyl, N-ethyl-N-methylcarbamoyl and N,N-diethylcarbamoyl;

for (2–6C)alkanoyl: acetyl and propionyl;

for (1–6C)alkylamino: methylamino, ethylamino and propylamino;

for di-[(1–6C)alkyl]amino: dimethylamino, diethylamino and N-ethyl-N-methylamino;

for halogeno-(1–6C)alkyl: fluoromethyl, chloromethyl, bromomethyl, difluoromethyl, dichloromethyl, dibromomethyl, 2-fluoroethyl, 2-chloroethyl and 2-bromoethyl;

for hydroxy-(1–6C)alkyl: hydroxymethyl, 2-hydroxyethyl, 1-hydroxyethyl and 3-hydroxypropyl;

for (1–4C)alkoxy-(1–6C)alkyl: methoxymethyl, ethoxymethyl, 1-methoxyethyl, 2-methoxyethyl, 2-ethoxyethyl and 3-methoxypropyl;

for cyano-(1–6C)alkyl: cyanomethyl, 2-cyanoethyl, 1-cyanoethyl and 3-cyanopropyl;

for amino-(1–6C)alkyl: aminomethyl, 2-aminoethyl, 1-aminoethyl and 3-aminopropyl;

for (1–6C)alkylamino-(1–6C)alkyl; methylaminomethyl, ethylaminomethyl, 1-methylaminoethyl, 2-methylaminoethyl, 2-ethylaminoethyl and 3-methylaminopropyl;

for di-[(1–6C)alkyl]amino-(1–6C)alkyl: dimethylaminomethyl, diethylaminomethyl, 1dimethylaminoethyl, 2-dimethylaminoethyl and 3-dimethylaminopropyl.

Suitable values for $R^1$, $R^4$ or $Q^2$ and suitable values for a substituent on $R^1$, $R^4$ or $Q^2$ include:

for aryl-(1–6C)alkyl: benzyl, 2-phenylethyl, 2-phenylpropyl and 3-phenylpropyl;

for aryl-(1–6C)alkoxy: benzyloxy and 2-phenylethoxy;

for aryloxy: phenoxy and 2-naphthyloxy;

for arylamino: anilino;

for N-(1–6C)alkyl-arylamino: N-methylanilino and N-ethylanilino;

for aryl-(1–6C)alkylamino: benzylamino, 2-phenethylamino, 2-phenylpropylamino and 3-phenylpropylamino;

for N-(1–6C)alkyl-aryl-(1–6C)alkylamino: N-benzyl-N-methylamino;

for aroylamino: benzamido and 2-naphthoylamino; arylsulphonylamino: benzenesulphonylamido;

for N-arylsulphamoyl: N-phenylsulphamoyl;

for aryl-(2–6C)alkanoylamino: phenylacetamido and 3-phenylpropionamido;

for heteroaryl-(1–6C)alkyl: heteroarylmethyl, 2-heteroarylethyl, 2-heteroarylpropyl and 3-heteroarylpropyl;

for heteroaryl-(1–6C)alkoxy: heteroarylmethoxy and 2-heteroarylethoxy;

for N-(1–6C)alkyl-heteroarylamino: N-methylheteroarylamino;

for heteroaryl-(1–6C)alkylamino: heteroarylmethylamino, 2-heteroarylethylamino and 3-heteroarylpropylamino;

for N-(1–6C)alkyl-heteroaryl-(1–6C)alkylamino: N-methylheteroarylmethylamino and N-methyl-2-heteroarylethylamino;

for heteroaryl-(2–6C)alkanoylamino: heteroarylacetamido and 3-heteroarylpropionamido;

for heteroaryl-(1–6C)alkoxy-(1–6C)alkyl: heteroarylmethoxymethyl, 2-heteroarylethoxymethyl and 3-heteroarylpropoxymethyl;

for heteroaryl-(1–6C)alkylamino-(1–6C)alkyl: heteroarylmethylaminomethyl, 2-heteroarylethylaminomethyl and 3-heteroarylpropylaminomethyl;

for N-(1–6C)alkyl-heteroaryl-(1–6C)alkylamino-(1–6C)alkyl: N-heteroarylmethyl-N-methylaminomethyl, N-(2-heteroarylethyl)-N-methylaminomethyl and N-(3-heteroarylpropyl)-N-methylaminomethyl;

for heterocyclyl-(1–6C)alkyl: heterocyclylmethyl, 2-heterocyclylethyl, 2-heterocyclylpropyl and 3-heterocyclylpropyl;

for heterocyclyl-(1–6C)alkoxy: heterocyclylmethoxy and 2-heterocyclylethoxy;

for N-(1–6C)alkyl-heterocyclylamino: N-methylheterocyclylamino;

for heterocyclyl-(1–6C)alkylamino: heterocyclylmethylamino, 2-heterocyclylethylamino and 3-heterocyclylpropylamino;

for N-(1–6C)alkyl-heterocyclyl-(1–6C)alkylamino: N-methylheterocyclylmethylamino and N-methyl-2-heterocyclylethylamino;

for heterocyclyl-(2–6C)alkanoylamino: heterocyclylacetamido and 3-heterocyclylpropionamido;

for heterocyclyl-(1–6C)alkoxy-(1–6C)alkyl: heterocyclylmethoxymethyl, 2-heterocyclylethoxymethyl and 3-heterocyclylpropoxymethyl;

for heterocyclyl-(1–6C)alkylamino-(1–6C)alkyl: heterocyclylmethylaminomethyl, 2-heterocyclylethylaminomethyl and 3-heterocyclylethylaminomethyl;

for N-(1–6C)alkyl-heterocyclyl-(1–6C)alkylamino-(1–6C)alkyl: N-heterocyclylmethyl-N-methylaminomethyl, N-(2-heterocyclylethyl)-N-methylaminomethyl and N-(3-heterocyclylpropyl)-N-methylaminomethyl;

for (1–3C)alkylenedioxy: methylenedioxy, ethylenedioxy and propylenedioxy;

for (1–6C)alkylthio: methylthio, ethylthio and propylthio;

for (1–6C)alkylsulphinyl: methylsulphinyl, ethylsulphinyl and propylsulphinyl;

for (1–6C)alkylsulphonyl: methylsulphonyl, ethylsulphonyl and propylsulfonyl;

for (2–6C)alkanoyloxy: acetoxy and propionyloxy:
for (1–6C)alkanoylamino: formamido, acetamido and propionamido;
for N-(1–6C)alkylsulphamoyl: N-methylsulphamoyl and N-ethylsulphamoyl;
for N,N-di-[(1–6C)alkyl]sulphamoyl: N N-dimethylsulphamoyl;
for (1–6C)alkanesulphonylamino: methanesulphonylamino and ethanesulphonylamino;
for N-(1–6C)alkyl-(1–6C)alkanesulphonylamino: N-methylmethanesulphonylamino and N-methylethanesulphonylamino;
for halogeno-(1–6C)alkyl: fluoromethyl, chloromethyl, bromomethyl, difluoromethyl, dichloromethyl, dibromomethyl, 2-fluoroethyl, 2chloroethyl and 2-bromoethyl;
for hydroxy-(1–6C)alkyl: hydroxymethyl, 2-hydroxyethyl, 1-hydroxyethyl and 3-hydroxypropyl;
for (1–4C)alkoxy-(1–6C)alkyl: methoxymethyl, ethoxymethyl, 1-methoxyethyl, 2-methoxyethyl, 2-ethoxyethyl and 3-methoxypropyl;
for cyano-(1–6C)alkyl: cyanomethyl, 2-cyanoethyl, 1-cyanoethyl and 3-cyanopropyl;
for amino-(1–6C)alkyl: aminomethyl, 2-aminoethyl, 1-aminoethyl and 3-aminopropyl;
for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;
for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl;
for carboxy-(1–6C)alkyl: carboxymethyl, 1-carboxyethyl, 2-carboxyethyl, 3-carboxypropyl and 4-carboxybutyl;
for (1–6C)alkoxycarbonyl-(1–6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;
for carbamoyl-(1–6C)alkyl: carbamoylmethyl, 1-carbamoylethyl, 2carbamoylethyl and 3-carbamoylpropyl;
for N-(1–6C)alkylcarbamoyl-(1–6C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;
for N,N-di-[(1–6C)alkyl]carbamoyl-(1–6C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl;
for halogeno-(2–6C)alkoxy: 2-chloroethoxy, 2-bromoethoxy and 3-chloropropoxy;
for hydroxy-(2–6C)alkoxy: 2-hydroxyethoxy, 3-hydroxypropoxy, 2-hydroxy-1-methylethoxy, 2-hydroxy-2-propoxy and 4-hydroxybutoxy;
for (1–6C)alkoxy-(2–6C)alkoxy: 2-methoxyethoxy, 2-ethoxyethoxy, 3-methoxypropoxy, 2-methoxy-1-methylethoxy and 4-ethoxybutoxy;

for cyano-(1–6C)alkoxy: cyanomethoxy, 2-cyanoethoxy and 3-cyanopropoxy;
for carboxy-(1–6C)alkoxy: carboxymethoxy, 1-carboxyethoxy, 2-carboxyethoxy and 3-carboxypropoxy;
for (1–6C)alkoxycarbonyl-(1–6C)alkoxy: methoxycarbonylmethoxy, ethoxycarbonylmethoxy, tert-butoxycarbonylmethyl, 2-methoxycarbonylethoxy and 3-ethoxycarbonylpropoxy;
for carbamoyl-(1–6C)alkoxy: carbamoylmethoxy and 2-carbamoylethoxy;
for N-(1–6C)alkylcarbamoyl-(1–6C)alkoxy: N-methylcarbamoylmethoxy, 2-(N-ethylcarbamoyl)ethoxy and 3-(N-methylcarbamoyl)propoxy;
for N,N-di-[(1–6C)alkyl]carbamoyl-(1–6C)alkoxy: N,N-dimethylcarbamoylmethoxy, 2-(N,N-dimethylcarbamoyl)ethoxy and 3-(N,N-diethylcarbamoyl)propoxy;
for amino-(2–6C)alkoxy: 2-aminoethoxy, 2-amino-1-methylethoxy, 3-aminopropoxy, 2-amino-2-methylpropoxy and 4-aminobutoxy;
for (1–6C)alkylamino-(2–6C)alkoxy: 2-methylaminoethoxy, 2-methylamino-1-methylethoxy and 3-ethylaminopropoxy;
for di-[(1–6C)alkyl]amino-(2–6C)alkoxy: 2-dimethylaminoethoxy, 2-diethylaminoethoxy, 2-dimethylaminopropoxy, 2-dimethylamino-2-methylethoxy, 3-dimethylaminopropoxy and 4-dimethylaminobutoxy;
for halogeno-(2–6C)alkylamino: 2-fluoroethylamino, 2-chloroethylamino, 2-bromoethylamino, 3-fluoropropylamino and 3-chloropropylamino;
for hydroxy-(2–6C)alkylamino: 2-hydroxyethylamino, 3-hydroxypropylamino, 2-hydroxy-2-methylpropylamino and 4-hydroxybutylamino;
for (1–6C)alkoxy-(2–6C)alkylamino: 2-methoxyethylamino, 2-ethoxyethylamino, 3-methoxypropylamino and 3-ethoxypropylamino;
for cyano-(1–6C)alkylamino: cyanomethylamino, 2-cyanoethylamino and 3-cyanopropylamino;
for carboxy-(1–6C)alkylamino: carboxymethylamino, 1-carboxyethylamino, 2-carboxyethylamino and 3-carboxypropylamino;
for (1–6C)alkoxycarbonyl-(1–6C)alkylamino: methoxycarbonylmethylamino, 2-(ethoxycarbonyl)ethylamino and 3-(tert-butoxycarbonyl)propylamino;
for carbamoyl-(1–6C)alkylamino: carbamoylmethylamino and 2-carbamoylethylamino;
for N-(1–6C)alkylcarbamoyl-(1–6C)alkylamino: N-methylcarbamoylmethylamino, N-ethylcarbamoylmethylamino and 2(N-methylcarbamoyl)ethylamino;
for N,N-di-[(1–6C)alkyl]carbamoyl-(1–6C)alkylamino: N,N-dimethylcarbamoylmethylamino, N,N-diethylcarbamoylmethylamino and 2-(N-dimethylcarbamoyl)ethylamino;
for amino-(2–6C)alkylamino: 2-aminoethylamino, 3-aminopropylamino, 2-amino-2-methylpropylamino and 4-aminobutylamino;
for (1–6C)alkylamino-(2–6C)alkylamino: 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino;

for di-[(1–6C)alkyl]amino-(2–6C)alkylamino: 2-dimethylaminoethylamino, 2-(N-ethyl-N-methylamino)ethylamino, 2-diethylaminoethylamino, 2-dipropylaminoethylamino, 3dimethylaminoethylamino, 3-diethylaminopropylamino, 2-dimethylamino-2-methylpropylamino and 4-dimethylaminobutylamino;

for N-(1–6C)alkyl-halogeno-(2–6C)alkylamino: N-(2-chloroethyl)-N-methylamino, N-(2-bromoethyl)-N-methylamino and N-(2-bromoethyl)-N-ethylamino;

for N-(1–6C)alkyl-hydroxy-(2–6C)alkylamino: N-(2-hydroxyethyl)-N-methylamino, N-(3-hydroxypropyl)-N-methylamino and N-ethyl-N-(2-hydroxyethyl)amino;

for N-(1–6C)alkyl-(1–6C)alkoxy-(2–6C)alkylamino: N-methyl-N-(2-methoxyethyl)amino, N-methyl-N-(3-methoxypropyl)amino and N-ethyl-N-(2-methoxyethyl)amino;

for N-(1–6C)alkyl-cyano-(1–6C)alkylamino: N-(cyanomethyl)-N-methylamino;

for N-(1–6C)alkyl-carboxy-(1–6C)alkylamino: N-carboxymethyl-N-methylamino and N-(2-carboxyethyl)-N-methylamino;

for N-(1–6C)alkyl-(1–6C)alkoxycarbonyl-(1–6C)alkylamino: N-methoxycarbonylmethyl-N-methylamino, N-(2-ethoxycarbonylethyl)-N-ethylamino and N-(2-tert-butoxycarbonylethyl)-N-methylamino;

for N-(1–6C)alkyl-carbamoyl-(1–6C)alkylamino: N-carbamoylmethyl-N-methylamino and N-(2-carbamoylethyl)-N-methylamino;

for N-(1–6C)alkyl-N-(1–6C)alkylcarbamoyl-(1–6C)alkylamino: N-(-methylcarbamoylmethyl)-N-methylamino, N-(-ethylcarbamoylmethyl)-N-methylamino and N-[2-(N-methylcarbamoyl)ethyl]-N-methylamino;

for N-(1–6C)alkyl-N,N-di-[(1–6C)alkyl]carbamoyl-(1–6C)alkylamino: N-(N,N-dimethylcarbamoylmethyl)-N-methylamino and N-[2-(N,N-dimethylcarbamoyl)ethyl]-N-methylamino;

for N-(1–6C)alkyl-amino-(2–6C)alkylamino: N-(2-aminoethyl)-N-methylamino, N-(3-aminopropyl)-N-methylamino and N-(4-aminobutyl)-N-methylamino;

for N-(1–6C)alkyl-(1–6C)alkylamino-(2–6C)alkylamino: N-(2-methylaminoethyl)-N-methylamino, N-(2-methylaminoethyl)-N-methylamino, N-(3-methylaminopropyl)-N-methylamino, N-(3-ethylaminopropyl)-N-ethylamino and N-(4-methylaminobutyl)-N-methylamino;

for N-(1–6C)alkyl-di-[(1–6C)alkyl]amino-(2–6C)alkylamino: N-(2-dimethylaminoethyl)-N-methylamino, N-(2-diethylaminoethyl)-N-methylamino, N-(3-dimethylaminopropyl)-N-methylamino and N-(4-dimethylaminobutyl)-N-methylamino;

for halogeno-(2–6C)alkanoylamino: 2-chloroacetamido and 3-chloropropionamido;

for hydroxy-(2–6C)alkanoylamino: 2-hydroxyacetamido and 3-hydroxypropionamido;

for (1–6C)alkoxy-(2–6C)alkanoylamino: 2-methoxyacetamido and 3-methoxypropionamido;

for cyano-(2–6C)alkanoylamino: 2-cyanoacetamido and 3-cyanopropionamido;

for carboxy-(2–6C)alkanoylamino: 2-carboxyacetamido and 3-carboxypropionamido;

for(1–6C)alkoxycarbonyl-(2–6C)alkanoylamino: 2-methoxycarbonylacetamido, 2-(tert-butoxycarbonyl)acetamido and 3-methoxycarbonylpropionamido;

for carbamoyl-(2–6C)alkanoylamino: 2-carbamoylacetamido, 3-carbamoylpropionamido and 4-carbamoylbutyramido;

for N-(1–6C)alkylcarbamoyl-(2–6C)alkanoylamino: 2-(N-methylcarbamoyl)acetamido and 3-(N-ethylcarbamoyl)propionamido;

for N,N-di-[(1–6C)alkyl]carbamoyl-(2–6C)alkanoylamino: 2-(N,N-dimethylcarbamoyl)acetamido, 2-(N,N-diethylcarbamoyl)acetamido and 3-(N,N-dimethylcarbamoyl)propionamido;

for amino-(2–6C)alkanoylamino: 2-aminoacetamido, 2-aminopropionamido and 3-aminopropionamido;

for (1–6C)alkylamino-(2–6C)alkanoylamino: 2-methylaminoacetamido, 2-ethylaminoacetamido, 2-methylaminopropionamido and 3-methylaminopropionamido;

for di-[(1–6C)alkyl]amino-(2–6C)alkanoylamino: 2-dimethylaminoacetamido, 2-diethylaminoacetamido, 2-dimethylaminopropionamido and 3-dimethylaminopropionamido.

When, as defined hereinbefore, any of the substituents on $R^4$ or $Q^2$ which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, suitable substituents so formed include, for example, substituted heterocyclyl-(1–6C)alkoxy groups such as 2-hydroxy-3-piperidinopropoxy and 2-hydroxy-3-morpholinopropoxy, substituted amino-(2–6C)alkoxy groups such as 3-amino-2-hydroxypropoxy, substituted (1–6C)alkylamino-(2–6C)alkoxy groups such as 2-hydroxy-3-methylaminopropoxy, substituted di-[(1–6C)alkyl]amino-(2–6C)alkoxy groups such as 3-dimethylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl-(1–6C)alkylamino groups such as 2-hydroxy-3-piperidinopropylamino and 2-hydroxy-3-morpholinopropylamino, substituted amino-(2–6C)alkylamino groups such as 3-amino-2-hydroxypropylamino, substituted (1–6C)alkylamino-(2–6C)alkylamino groups such as 2-hydroxy-3-methylaminopropylamino, substituted di-[(1–6C)alkyl]amino-(2–6C)alkylamino groups such as 3-dimethylamino-2-hydroxypropylamino, 3-[N-(3-dimethylaminopropyl)-N-methylamino]propylamino and 3-[N-(3-dimethylaminopropyl)-N-methylamino]-2-hydroxypropylamino and substituted (1–6C)alkylamino-(1–6C)alkyl groups such as 2-dimethylaminoethylamino, 3-dimethylaminopropylaminomethyl, 3-dimethylamino-2,2-dimethylpropylaminomethyl, 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:
a) Design of Prodrugs, edited by H. Bundgaard, (Elsevier, 1985) and *Methods in Enzymology,* Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, *Advanced Drug Delivery Reviews,* 8, 1–38 (1992);
d) H. Bundgaard, et al., *Journal of Pharmaceutical Sciences,* 77, 285 (1988); and
e) N. Kakeya, et al., *Chem. Pharm. Bull.,* 32, 692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1–6C)alkoxymethyl esters, for example methoxymethyl; (1–6C)alkanoyloxymethyl esters, for example pivaloyloxymethyl; phthalidyl esters; (3–8C)cycloalkoxycarbonyloxy(1–6C)alkyl esters, for example 1-cyclohexylcarbonyloxyethyl; 1,3-dioxolan-2-ylmethyl esters, for example 5-methyl-1,3-dioxolan-2-ylmethyl; and (1–6C)alkoxycarbonyloxyethyl esters, for example 1-methoxycarbonyloxyethyl; and may be formed at any carboxy group in the compounds of this invention.

Particular novel compounds of the invention include, for example, amide derivatives of the Formula I, or pharmaceutically-acceptable salts thereof, wherein:

(a) $R^3$ is (1–6C)alkyl such as methyl, ethyl, propyl and isopropyl, preferably methyl and ethyl, more preferably methyl; and $R^1$, $R^2$, $R^4$, $Q^2$, m, p and q have any of the meanings defined hereinbefore or in this section relating to particular novel compounds of the invention;

(b) $R^3$ is halogeno such as fluoro, bromo and chloro, preferably chloro and bromo, more preferably chloro; and $R^1$, $R^2$, $R^4$, $Q^2$, m, p and q have any of the meanings defined hereinbefore or in this section relating to particular novel compounds of the invention;

(c) $Q^2$ is a heteroaromatic 5- or 6-membered monocyclic ring or a 9- or 10-membered bicyclic ring with up to five ring heteroatoms selected from oxygen, nitrogen and sulphur which bears a basic substituent selected from the substituents for $Q^2$ defined hereinbefore; and $R^1$, $R^2$, $R^3$, $R^4$, m, p and q have any of the meanings defined hereinbefore or in this section relating to particular novel compounds of the invention;

(d) $Q^2$ is a heteroaromatic 5- or 6-membered monocyclic ring or a 9- or 10-membered bicyclic ring with up to five ring heteroatoms selected from oxygen, nitrogen and sulphur which bears a basic substituent selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C)alkanoylamino, heteroaryl, heteroaryl-(1–6C)alkyl, heteroaryl-(1–6C)alkoxy, heterocyclyl, heterocyclyl-(1–6C)alkyl and heterocyclyl-(1–6C)alkoxy, and wherein any heteroaryl or heterocyclyl group in a basic substituent on $Q^2$ may optionally bear 1 or 2 substituents selected from halogeno, (1–6C)alkyl, (2–6C)alkanoyl, amino, (1–6C)alkylamino and di-[(1–6C)alkyl]amino; and $R^1$, $R^2$, $R^3$, $R^4$, m, p and q have any of the meanings defined hereinbefore or in this section relating to particular novel compounds of the invention;

(e) $Q^2$ is a heteroaromatic 5- or 6-membered monocyclic ring or a 9- or 10-membered bicyclic ring with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3C)alkylenedioxy, (1–6C)alkylamino, di-[(1–6C)alkyl]amino, (1–6C)alkoxycarbonyl, (2–6C)alkanoyl, halogeno-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, halogeno-(2–6C)alkoxy, hydroxy2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, amino-(2–6C)alkoxy, (1–6C)alkylamino-(2–6C)alkoxy, di-[(1–6C)alkyl]amino-(2–6C)alkoxy, pyridyl, imidazolyl, pyridyl-(1–6C)alkyl, imidazolyl-(1–6C)alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, 4-(2–6C)alkanoylpiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, 4-(2–6C)alkanoylpiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy, and 4-(2–6C)alkanoylpiperazinyl-(2–6C)alkoxy; and $R^1$, $R^2$, $R^3$, $R^4$, m, p and q have any of the meanings defined hereinbefore or in this section relating to particular novel compounds of the invention;

(f) $Q^2$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from those defined in paragraph (c), (d) or (e) hereinbefore; and $R^1$, $R^2$, $R^3$, $R^4$, m, p and q have any of the meanings defined hereinbefore or in this section relating to particular novel compounds of the invention;

(g) $Q^2$ is 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothiophenyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6 or 7quinolyl, 3-, 6 or 7-isoquinolyl, 2-, 6- or 7-quinazolinyl, 2-, 6- or 7-quinoxalinyl, or 1,8-naphthyridin-2-yl or 1,8-naphthyridin-3-yl which optionally bears 1 or 2 substituents selected from those defined in paragraph (c), (d) or (e) hereinbefore; and $R^1$, $R^2$, $R^3$, $R^4$, m, p and q have any of the meanings defined hereinbefore or in this section relating to particular novel compounds of the invention;

(h) $Q^2$ is a heteroaromatic 5- or 6-membered monocyclic ring, a 9- or 10-membered bicyclic ring or a 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3C)alkylenedioxy, (1–6C)alkylamino, di-[(1–6C)alkyl]amino and (1–6C)alkoxycarbonyl; and $R^1$, $R^2$, $R^3$, $R^4$, m, p and q have any of the meanings defined hereinbefore or in this section relating to particular novel compounds of the invention;

(i) $Q^2$ is a heteroaromatic 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3 C)alkylenedioxy, (1–6C)alkylamino, di-[(1–6C)alkyl]amino and (1–6C)alkoxycarbonyl; and $R^1$, $R^2$, $R^3$, $R^4$, m, p and q have any of the meanings defined hereinbefore or in this section relating to particular novel compounds of the invention;

(j) $Q^2$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl: benzoxazolyl, benzimidazolyl, benzothiazolyl, indazolyl, benzofurazanyl, quinolyl, isoquinolyl, quinazolinyl, quinoxalinyl, naphthyridinyl, carbazolyl, dibenzofuranyl, dibenzothiophenyl or xanthenyl which optionally bears 1 or 2 substituents selected from those defined in paragraph (h) hereinbefore; and $R^1$, $R^2$, $R^3$, $R^4$, m, p and q have any of the meanings defined hereinbefore or in this section relating to particular novel compounds of the invention;

(k) $Q^2$ is 1-, 2- or 3carbazolyl, 1-, 2-, 3- or 4-dibenzofuranyl or 1-, 2-, 3- or 4-dibenzothiophenyl which optionally bears 1 or 2 substituents selected from those defined in paragraph (h) hereinbefore; and $R^1$, $R^2$, $R^3$, $R^1$, m, p and q have any of the meanings defined hereinbefore or in this section relating to particular novel compounds of the invention;

(l) $R^1$ is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino, and m is 1; and $R^2$, $R^3$, $R^4$, $Q^2$, p and q have any of the meanings defined hereinbefore or in this section relating to particular novel compounds of the invention;

(m) m is 0; and $R^2$, $R^3$, $R^4$, $Q^2$, p and q have any of the meanings defined hereinbefore or in this section relating to particular novel compounds of the invention;

(n) p is 0; and $R^1$, $R^3$, $R^4$, $Q^2$, m and q have any of the meanings defined hereinbefore or in this section relating to particular novel compounds of the invention;

(o) q is 0, and $R^1$, $R^2$, $R^3$, $R^1$, $Q^2$, m and p have any of the meanings defined hereinbefore or in this section relating to particular novel compounds of the invention;

(p) $R^4$ is amino, (1–6C)alkylamino, di-[(1–6C)alkyl]amino, amino-(1–6C)alkyl, (1–6C)alkylamino-(1–6C) alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C) alkylamino, (1–6C)alkylamino-(2–6C)alkylamino, di-[(1–6C)alkyl]amino-(2–6C)alkylamino, heteroaryl, heteroaryl-(1–6C)alkyl, heteroaryl-(1–6C)alkoxy, heterocyclyl, heterocyclyl-(1–6C)alkyl, heterocyclyloxy or heterocyclyl-(1–6C)alkoxy, and wherein any heteroaryl or heterocyclyl group in a $R^4$ substituent may optionally bear 1 or 2 substituents selected from hydroxy, halogeno, (1–6C)alkyl, (1–6C)alkoxy, (2–6C) alkanoyl, amino, (1–6C)alkylamino and di-[(1–6C) alkyl]amino; and $R^1$, $R^2$, $R^3$, $Q^2$, m, p and q have any of the meanings defined hereinbefore or in this section relating to particular novel compounds of the invention;

(q) $R^4$ is amino, (1–6C)alkylamino, di-[(1–6C)alkyl] amino, amino-(1–6C)alkyl, (1–6C)alkylamino-(1–6C) alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, pyridyl, imidazolyl, pyridyl-(1–6C)alkyl, imidazolyl-(1–6C) alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, 4-(2–6C) alkanoylpiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, 4-(2–6C)alkanoylpiperazinyl-(1–6C) alkyl, pyrrolidinyloxy, piperidinyloxy, 1-(1–6C) alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy or 4-(2–6C)alkanoylpiperazinyl-(2–6C) alkoxy; and $R^1$, $R^2$, $R^3$, $Q^2$, m, p and q have any of the meanings defined hereinbefore or in this section relating to particular novel compounds of the invention; and (r) $R^4$ is amino, (1–6C)alkylamino, di-[(1–6C)alkyl] amino, amino-(1–6C)alkyl, (1–6C)alkylamino-(1–6C) alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C) alkylamino, (1–6C)alkylamino-(2–6C)alkylamino, di-[(1–6C)alkyl]amino-(2–6C)alkylamino, N-(1–6C) alkyl-amino-(2–6C)alkylamino, N-(1–6C)alkyl-(1–6C) alkylamino-(2–6C)alkylamino, N-(1–6C)alkyl-di-[(1–6C)alkyl]amino-(2–6C)alkylamino, pyridyl, imidazolyl, pyridyl-(1–6C)alkyl, imidazolyl-(1–6C) alkyl, pyridyl-(1–6C)alkoxy, imidazolyl-( 1–6C) alkoxy, pyrrolidinyl, piperidinyl, morpholinyl, piperazinyl, 4-(1–6C)alkylpiperazinyl, homopiperazinyl, 4-(1–6C)alkylhomopiperazinyl, 4-(2–6C)alkanoylpiperazinyl, pyrrolidinyl-(1–6C) alkyl, piperidinyl-(1–6C)alkyl, morpholinyl-(1–6C) alkyl, piperazinyl-(1–6C)alkyl, 4-(1–6C) alkylpiperazinyl-(1–6C)alkyl, homopiperazinyl-(1–6C)alkyl, 4-(1–6C)alkylhomopiperazinyl-(1–6C) alkyl, 4-(2C)alkanoylpiperazinyl-(1–6C)alkyl, pyrrolidinyloxy, piperidinyloxy, 1-(1–6C) alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy or 4-(2–6C)alkanoylpiperazinyl-(2–6C) alkoxy; and $R^1$, $R^2$, $R^3$, $Q^2$, m, p and q have any of the meanings defined hereinbefore or in this section relating to particular novel compounds of the invention.

A preferred compound of the invention is an amide derivative of the Formula I wherein $R^3$ is methyl, ethyl, chloro or bromo;

m is 0 or 1;

$R^1$ is hydroxy, fluoro, chloro, bromo, trifluoromethyl, cyano, amino, methyl, ethyl, methoxy, ethoxy, methylamino, ethylamino, dimethylamino or diethylamino;

p is 0;

$R^4$ is amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, 4-acetylpiperazinyl, pyrrolidinylmethyl, piperidinylmethyl, morpholinylmethyl, piperazinylmethyl, 4methylpiperazinylmethyl, 4-acetylpiperazinylmethyl, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4methylpiperazinyl)propoxy, 2-(4-acetylpiperazinyl)ethoxy or 3-(4acetylpiperazinyl)propoxy;

q is 0; and $Q^2$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, piperidinyloxy, 1-methylpiperidinyloxy, 2-(pyrrolidinyl)ethoxy, 3-(pyrrolidinyl)propoxy, 2(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy;

or a pharmaceutically-acceptable salt thereof.

A further preferred compound of the invention is an amide derivative of the Formula I wherein $R^3$ is methyl or ethyl;

each of m, p and q is 0;

$R^4$ is amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4methylpiperazin-1-yl)propoxy, 2-(4-acetylpiperazin-1-yl)ethoxy or 3-(4-acetylpiperazin-1-yl)propoxy; and $Q^2$ is 2-furyl, 2-thienyl, 4-oxazolyl, 5-isoxazolyl, 4-thiazolyl, 5-isothiazolyl, 2-pyridyl, 3-pyridyl, 4-pyridyl, 2-benzofuranyl, 2-indolyl, 2-benzothiophenyl, 2-benzoxazolyl, 2-benzimidazolyl, 2-benzothiazolyl, 4-benzofurazanyl, 2-quinolyl, 6-quinolyl, 7-quinolyl, 3-isoquinolyl, 6-quinazolinyl, 7-quinazolinyl, 6-quinoxalinyl or 7-quinoxalinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminoethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridyl, 3-pyridyl, 4-pyridyl, 2-pyridylmethyl, 3-pyridylmethyl, 4-pyridylmethyl, 2-pyridylmethoxy, 3-pyridylmethoxy, 4-pyridylmethoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy or a pharmaceutically-acceptable salt thereof A further preferred compound of the invention is an amide derivative of the Formula I wherein $R^3$ is methyl or ethyl;

each of m, p and q is 0;

$R^4$ is 4-diethylaminomethyl, 3-pyrid-2-ylmethoxy, 3-morpholino, 3-(4-methylpiperazin-1-ylmethyl), 3-(2-pyrrolidin-1-ylethoxy or 3-(2-piperidinoethoxy); and $Q^2$ is 2-furyl, 2-thienyl, 5-isoxazolyl, 4-thiazolyl, 3-pyridyl, 4-pyridyl, 2-benzothiophenyl, 4-benzofurazanyl, 2-quinolyl or 6-quinolyl which optionally bears 1 substituent selected from chloro, 2-pyridyl, 4-pyridyl, pyrrolidin-1-yl and morpholino;

or a pharmaceutically-acceptable salt thereof

A further preferred compound of the invention is an amide derivative of the Formula I wherein $R^3$ is methyl;

m is 0 or m is 1 and $R^1$ is hydroxy, fluoro, chloro, amino, methyl, methoxy, methylamino or dimethylamino;

each of p and q is 0;

$R^4$ is located at the 3- or 4-position and is selected from dimethylaminomethyl, diethylaminomethyl, 2-dimethylaminoethoxy, 2-diethylaminoethoxy, 3-dimethylaminopropoxy, 3-diethylaminopropoxy, 3-dimethylamino-2-hydroxypropoxy, 3-diethylamino-2-hydroxypropoxy, 2-aminoethylamino, 3-aminopropylamino, 4-aminobutylamino, 3-methylaminopropylamino, 2-dimethylaminoethylamino, 2-diethylaminoethylamino, 3-dimethylaminopropylamino, 4-dimethylaminobutylamino, 3-amino-2-hydroxypropylamino, 3-dimethylamino-2-hydroxypropylamino, N-(2-dimethylaminoethyl)-N-methylamino, N-(3 dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, piperidin-4-yloxy, 1-methylpiperidin-4-yloxy, 1-benzylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-hydroxy-3-pyrrolidin-1-ylpropoxy, 2-hydroxy-3-piperidinopropoxy, 2-hydroxy-3-morpholinopropoxy, piperidin-4-ylamino, 1-methylpiperidin-4-ylamino, 1-benzylpiperidin-4-ylamino, 2-pyrrolidin-1-ylethylamino, 3-pyrrolidin-1ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 2-dimethylaminoethylaminomethyl, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy; and $Q^2$ is 2-pyridyl, 3-pyridyl or 4-pyridyl which bears a substituent selected from pyrrolidin-1-yl, 3-hydroxypyrrolidin-1-yl, 2-hydroxymethylpyrrolidin-1-yl, morpholino, piperidino, 4-hydroxypiperidin-1-yl and piperazin-1-yl;

or a pharmaceutically-acceptable salt thereof.

An especially preferred compound of the invention is an amide derivative of the Formula I wherein $R^3$ is methyl;

each of m, p and q is 0;

$R^4$ is located at the 3- or 4-position and is selected from diethylaminomethyl, N-(3-dimethylaminopropyl)-N-methylamino, morpholino, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, piperidin-4-yloxy, 2-pyrrolidin-1-ylethoxy, 2-piperidinoethoxy, 2-morpholinoethoxy, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy; and $Q^2$ is 2-pyridyl, 3-pyridyl or 4-pyridyl which bears a substituent selected from pyrrolidin-1-yl, 2-hydroxymethylpyrrolidin-1-yl, morpholino and piperidino;

or a pharmaceutically-acceptable salt thereof.

A further especially preferred compound of the invention is an amide derivative of the Formula I wherein $R^3$ is methyl;

each of m, p and q is 0;

$R^4$ is 4-diethylaminomethyl, 3-piperazin-1-ylmethyl, 3-(4-methylpiperazin-1-ylmethyl), 3-(4-methylhomopiperazin-1-ylmethyl), 4-(4-methylhomopiperazin-1-ylmethyl), 4-morpholinomethyl, 3-(3-aminopyrrolidin-1-ylmethyl), 3-(3-hydroxypyrrolidin-1-ylmethyl), 4-(3-hydroxypyrrolidin-1-ylmethyl), 3-[4-(2-hydroxyethyl)piperazin-1-ylmethyl], 4-[4-(2-hydroxyethyl)piperazin-1-ylmethyl], 3-(3-pyrrolidin-1-ylpropylaminomethyl), 4-(3-pyrrolidin-1-ylpropylaminomethyl), 3-[2-(1-methylpyrrolidin-2-ylethyl)aminomethyl], 4-[2-(1-methylpyrrolidin-2-ylethyl)aminomethyl], 4-(2-morpholinoethylaminomethyl), 4-(3-morpholinopropylaminomethyl), 4-[3-(4-methylpiperazin-1-ylpropyl)aminomethyl] or 4-pyrid-2-ylmethoxy; and $Q^2$ is 4-morpholinopyrid-2-yl, 5-morpholinopyrid-3-yl, 2-morpholinopyrid-4-yl, 2-piperidinopyrid-4-yl, 2-pyrrolidin-1-ylpyrid-4-yl or 2-[(R)-(−)-2-hydroxymethylpyrrolidin-1-yl]pyrid-4-yl;

or a pharmaceutically-acceptable salt thereof.

A further preferred compound of the invention is an amide derivative of the Formula I wherein $R^3$ is methyl;

m is 0 or m is 1 and $R^1$ is nitro or amino;

each of p and q is 0;

R⁴ is located at the 3- or 4-position and is selected from diethylaminomethyl, N-(3-dimethylaminopropyl)-N-methylamino, pyrrolidin-1-yl, morpholino, piperidino, piperazin-1-yl, 4-methylpiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, homopiperazin-1-ylmethyl, 4-methylhomopiperazin-1-ylmethyl, 3-aminopyrrolidin-1-ylmethyl, 3-hydroxypyrrolidin-1-ylmethyl, 4-(2-hydroxyethyl) piperazin-1-ylmethyl, pyrrolidin-3-yloxy, N-methylpyrrolidin-3-yloxy, piperidin-4-yloxy, N-methylpiperidin-4-yloxy, N-ethylpiperidin-4-yloxy, N-isopropylpiperidin-4-yloxy, homopiperidin-4-yloxy, N-methylhomopiperidin-4-yloxy, 3-pyrrolidin-1-ylpropylaminomethyl, 2-(1-methylpyrrolidin-2-ylethyl)aminomethyl, 2-morpholinoethylaminomethyl, 3-morpholinopropylaminomethyl, 3-(4-methylpiperazin-1-ylpropyl)aminomethyl, pyrid-2-ylmethoxy, thiazol-4-ylmethoxy and 2-methylthiazol-4-ylmethoxy; and $Q^2$ is 2-pyridyl, 3-pyridyl or 4-pyridyl which bears a substituent selected from pyrrolidin-1-yl, 2-hydroxymethylpyrrolidin-1-yl, morpholino and piperidino, and wherein any of the 4 last-named substituents may optionally bear 1 or 2 methyl groups, or $Q^2$ is 2- or 4-dibenzofuranyl;

or a pharmaceutically-acceptable salt thereof.

A further preferred compound of the invention is an amide derivative of the Formula I wherein $R^3$ is methyl;

m is 0 or m is 1 and $R^1$ is nitro or amino;

each of p and q is 0;

R⁴ is located at the 3- or 4-position and is selected from diethylaminomethyl, N-(3-dimethylaminopropyl)-N-methylamino, pyrrolidin-1-yl, morpholino, piperidino, piperazin-1-yl, 4-methylpiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, homopiperazin-1-ylmethyl, 4-methylhomopiperazin-1-ylmethyl, 3-aminopyrrolidin-1-ylmethyl, 3-hydroxypyrrolidin-1-ylmethyl, 4-(2-hydroxyethyl) piperazin-1-ylmethyl, pyrrolidin-3-yloxy, piperidin-4-yloxy, 3-pyrrolidin-1-ylpropylaminomethyl, 2-(1-methylpyrrolidin-2-ylethyl)aminomethyl, 2-morpholinoethylaminomethyl, 3-morpholinopropylaminomethyl, 3-(4-methylpiperazin-1-ylpropyl)aminomethyl or pyrid-2-ylmethoxy; and $Q^2$ is 2-pyridyl, 3-pyridyl or 4-pyridyl which bears a substituent selected from pyrrolidin-1-yl, 2-hydroxymethylpyrrolidin-1-yl, morpholino and piperidino;

or a pharmaceutically-acceptable salt thereof.

A further preferred compound of the invention is an amide derivative of the Formula I wherein $R^3$ is methyl;

each of m, p and q is 0;

R⁴ is located at the 3- or 4-position and is selected from diethylaminomethyl, 4-methylpiperazin-1-yl, morpholinomethyl, piperazin-1-ylmethyl, 4-methylpiperazin-1-ylmethyl, 4-methylhomopiperazin-1-ylmethyl, 3-hydroxypyrrolidin-1-ylmethyl, pyrrolidin-3-yloxy, piperidin-4-yloxy, N-methylpiperidin-4-yloxy, N-isopropylpiperidin-4-yloxy, N-methylhomopiperidin-4-yloxy, 2-(N-methylpyrrolidin-2-yl)ethoxy, 3-dimethylamino-2,2-dimethylpropylaminomethyl N-(3-dimethylaminopropyl) -N-methylaminomethyl, 3-morpholinopropylaminomethyl and 2-methylthiazol4-ylmethoxy; and $Q^2$ is 4-pyridyl which bears a substituent selected from morpholino, piperidino, 3-methylpiperidin-1-yl and homopiperidin-1-yl, or $Q^2$ is 4-dibenzofuranyl;

or a pharmaceutically-acceptable salt thereof.

A particular preferred compound of the invention is, for example:

N-{4-methyl-3-[3-(4-methylpiperazin-1-ylmethyl) benzamido]phenyl}furan-2-carboxamide, N-{4-methyl -3-[3-(4-methylpiperazin-1-ylmethyl) benzamido]phenyl}isoxazole-5-carboxamide, N-[3-(4-diethylaminomethylbenzamido)-4-methylphenyl]-2-morpholinopyridine-4-carboxamide, N-{3-[3-(4-methylpiperazin-1-ylmethyl)benzamido]-4-methylphenyl}-2-pyrrolidin-1-ylpyridine4-carboxamide or N-{3-[3-(4-methylpiperazin-1-ylmethyl)benzamido]-4-methylphenyl}-2-morpholinopyridine-4-carboxamide;

or a pharmaceutically-acceptable salt thereof.

A further particular preferred compound of the invention is, for example:

N-{3-[3-(4-methylhomopiperazin-1-ylmethyl)benzamido]-4-methylphenyl}-2-morpholinopyridine-4-carboxamide, N-{3-[4-(4-methylhomopiperazin-1-ylmethyl)benzamido]-4-methylphenyl}-2-morpholinopyridine-4-carboxamide, N-[3-(3-piperazin-1-ylmethylbenzamido)-4-methylphenyl]-2-morpholinopyridine-4-carboxamide, N-{3-[4-(3-hydroxypyrrolidin-1-ylmethyl)benzamido]-4-methylphenyl}-2-morpholinopyridine-4-carboxamide, N-{3-[3-(3-pyrrolidin-1-ylpropylaminomethyl)benzamido]-4-methylphenyl}-2-morpholinopyridine-4-carboxamide or N-{3-[4-(3-morpholinopropylaminomethyl)benzamido]-4-methylphenyl}-2-morpholinopyridine4-carboxamide;

or a pharmaceutically-acceptable salt thereof.

A further particular preferred compound of the invention is, for example:

N-[3-(3-diethylaminomethylbenzamido)-4methylphenyl]-2-morpholinopyridine-4-carboxamide, N-[3-(4-diethylaminomethylbenzamido)-4-methylphenyl]-5-morpholinopyridine-3-carboxamide, N-[3-(4-diethylaminomethylbenzamido)-4-methylphenyl]-2-piperidinopyridine-4-carboxamide, N-{3-[3-(4-methylpiperazin-1-ylmethyl)benzamido]-4-methylphenyl}-2-(3-methylpiperidin-1-yl)pyridine-4-carboxamide, N-{3-[3-(4-methylpiperazin-1-ylmethyl)benzamido]-4-methylphenyl}-2-homopiperidin-1-ylpyridine4-carboxamide, N-[4-methyl-3-(4-morpholinomethylbenzamido)phenyl]-2-morpholinopyridine-4-carboxamide, N-{3-[3-(3-dimethylamino-2,2-dimethylpropylaminomethyl)benzamido]-4-methylphenyl}-2-morpholinopyridine-4-carboxamide, N-{3-[4-(3-dimethylamino-2,2-dimethylpropylaminomethyl)benzamido]-4-methylphenyl}-2-morpholinopyridine-4-carboxamide, N-(3-{4-[N-(3-dimethylaminopropyl)-N-methylaminomethyl]benzamido}-4-methylphenyl)-2-morpholinopyridine-4-carboxamide, N-[4-methyl-3-(3-piperidin-4-yloxybenzamido)phenyl]-2-morpholinopyridine-4-carboxamide, N-[4-methyl-3-(3-pyrrolidin-3-yloxybenzamido)phenyl]-2-morpholinopyridine-4-carboxamide, N-{3-[3-methylhomopiperidin-4-yloxy)benzamido]-4-methylpenyl}-2-morpholinopyridine-4-carboxamide, N-(3-{3-[2-(N-methylpyrrolidin-2-yl)ethoxy]benzamido}-4-methylphenyl)-2-morpholinopyridine-4-carboxamide, N-{4-methyl-3-[4-(2-methylthiazol-4-ylmethoxy)benzamido]phenyl}-2-morpholinopyridine-4-carboxamide or N-{3-[3-(4-methylpiperazin-1-ylmethyl)benzamido]-4-methylphenyl}dibenzofuran-4-carboxamide;

or a pharmaceutically-acceptable salt thereof.

An amide derivative of the Formula I, or a pharmaceutically-acceptable salt or in-vivo-cleavable ester thereof, may be prepared by any process known to be applicable to the preparation of chemically-related compounds. Such processes, when used to prepare a novel amide derivative of the Formula I are provided as a further feature of the invention and are illustrated by the following representative process variants in which, unless otherwise stated, $R^1$, $R^2$, $R^3$, $R^4$, m, p, q and $Q^2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in-vivo-cleavable ester thereof, may be prepared by reacting an aniline of the Formula II

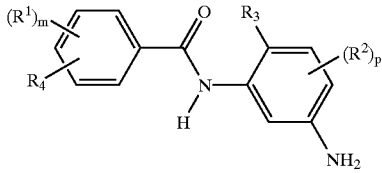

with an acid of the Formula III, or a reactive derivative thereof,

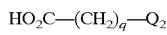

under standard amide bond forming conditions, wherein variable groups are as defined hereinbefore and wherein any functional group is protected if necessary, and:

(i) removing any protecting groups; and (ii) optionally forming a pharmaceutically-acceptable salt or in-vivo-cleavable ester.

A suitable activated derivative of an acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and (2–6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; tri-alkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The aniline of Formula II may be prepared by reduction of the corresponding nitro compound of Formula IV.

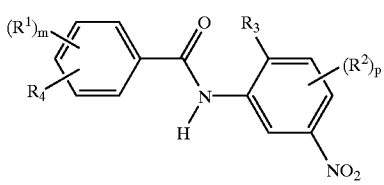

IV

Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

The nitrobenzene of Formula IV may be prepared by the reaction of a benzoic acid of Formula V, or an activated derivative thereof as defined hereinbefore,

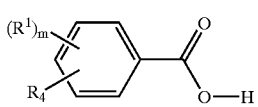

V with an aniline of Formula VI

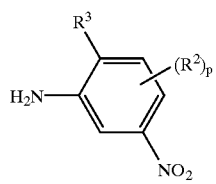

VI under suitable amide bond forming conditions as defined hereinbefore.

Typical conditions include activating the carboxy group of the compound of Formula V, for example by treatment with a halo reagent (for example oxalyl chloride) to form an acyl halide in an organic solvent at ambient temperature and then reacting the activated compound with the aniline of Formula VI. Any functional groups are protected and deprotected as necessary.

(b) A compound of the Formula I, or a pharmaceutically-acceptable salt or in-vivo-cleavable ester thereof, may be prepared by reacting an acid of the Formula V, or an activated derivative thereof as defined hereinbefore,

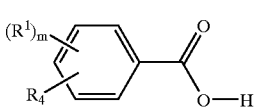

V with an aniline of the Formula VII

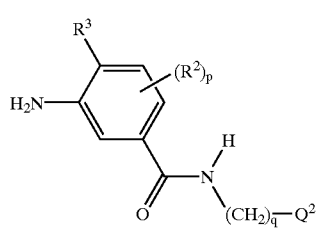

VII under standard amide bond forming conditions as defined hereinbefore, wherein variable groups are as defined hereinbefore and wherein any functional group is protected, if necessary, and:
(i) removing any protecting groups; and
(ii) optionally forming a pharmaceutically-acceptable salt or in-vivo-cleavable ester.

The aniline of Formula VII may be prepared by reduction of the corresponding nitro compound using convention procedures as defined hereinbefore or as illustrated in the Examples.

(c) A compound of the Formula I wherein $R^1$, $R^4$ or a substituent on $Q^2$ is (1–6C)alkoxy or substituted (1–6C) alkoxy, (1–6C)alkylthio, (1–6C)alkylamino, di-[(1–6C) alkyl]amino or substituted (1–6C)alkylamino may be prepared by the alkylation, conveniently in the presence of a suitable base as defined hereinbefore, of an amide derivative of the Formula I wherein $R^1$, $R^4$ or a substituent on $Q^2$ is hydroxy, mercapto or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, in the presence of a suitable base as defined hereinbefore, in a suitable inert solvent or diluent as defined hereinbefore and at a temperature in the range, for example, 10 to 140° C., conveniently at or near ambient temperature.

(d) A compound of the Formula I wherein a substituent on $Q^2$ is amino, (1–6C)alkylamino, di-[(1–6C)alkyl]amino, substituted (1–6C)alkylamino, substituted N-(1–6C)alkyl-(2–6C)alkylamino or a N-linked heterocyclyl group may be prepared by the reaction, conveniently in the presence of a suitable base as defined hereinbefore, of an amide derivative of the Formula I wherein a substituent on $Q^2$ is a suitable leaving group with an appropriate amine.

A suitable leaving group is, for example, a halogeno group such as fluoro, chloro or bromo, a (1–6) alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 75 to 150° C.

(e) A compound of the Formula I wherein $R^1$, $R^4$ or a substituent on $Q^2$ is (1–6C)alkanoylamino or substituted (2–6C)alkanoylamino may be prepared by the acylation of a compound of the Formula I wherein $R^1$, $R^4$ or a substituent on $Q^2$ is amino.

A suitable acylating agent is, for example, any agent known in the art for the acylation of amino to acylamino, for example an acyl halide, for example a (1–6C)alkanoyl chloride or bromide, conveniently in the presence of a suitable base, as defined hereinbefore, an alkanoic acid anhydride or mixed anhydride, for example a (1–6C) alkanoic acid anhydride such as acetic anrhydride or the mixed anhydride formed by the reaction of an alkanoic acid and a (1–6C)alkoxycarbonyl halide, for example a (1–6C) alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

(f) A compound of the Formula I wherein $R^1$ or a substituent on $Q^2$ is (1–6C)alkanesulphonylamino may be prepared by the reaction of a compound of the Formula I wherein $R^1$ or a substituent on $Q^2$ is amino with a (1–6C) alkanesulphonic acid, or an activated derivative thereof.

A suitable activated derivative of a (1–6C) alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(g) A compound of the Formula I wherein $R^1$ or a substituent on $Q^2$ is carboxy, carboxy-(1–6C)alkyl, carboxy-(1–6C) alkoxy, carboxy-(1–6C)alkylamino, N-(1–6C)alkyl-carboxy-(1–6C)alkylamino or carboxy-(2–6C) alkanoylamino may be prepared by the cleavage of a compound of the Formula I wherein $R^1$ or a substituent on $Q^2$ is (1–6C)alkoxycarbonyl, (1–6C)alkoxycarbonyl-(1–6C)alkyl, (1–6C)alkoxycarbonyl-(1–6C)alkoxy, (1–6C)alkoxycarbonyl-(1–6C)alkylamino, N-(1–6C) alkyl-(1–6C)alkoxycarbonyl-(1–6C)alkylamino or (1–6C)alkoxycarbonyl-(2–6C)alkanoylamino as appropriate.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(h) A compound of the Formula I wherein $R^4$ is amino-(1–6C)alkyl, (1–6C)alkylamino-(1–6C)alkyl, di-[(1–6C) alkyl]amino-(1–6C)alkyl or a heterocyclyl-(1–6C)alkyl group maybe prepared by the reaction, conveniently in the presence of a suitable base as defined hereinbefore, of a compound of the Formula VIII

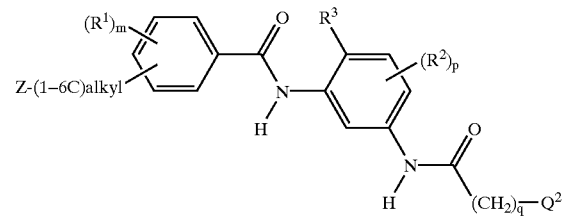

VIII wherein $R^1$, $R^2$, $R^3$, m, p, q and $Q^2$ have any of the meanings defined hereinbefore and Z is a suitable leaving group with an appropriate amine or heterocycle.

A suitable leaving group Z is, for example, a halogeno group such as fluoro, chloro or bromo, a (1–6C) alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 50 to 150° C.

(i) A compound of the Formula I wherein $R^1$, $R^2$, $R^4$ or a substituent on $Q^2$ is an amino group may be prepared by the reduction of a compound of the Formula I wherein $R^1$, $R^2$, $R^4$ or a substituent on $Q^2$ iS a nitro group.

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent preferably a polar protic solvent) and preferably with heating, for example to about 60° C. Any functional groups are protected and deprotected as necessary.

The following biological assays and Examples serve to illustrate the present invention.

Biological Assays

The following assays can be used to measure the p38 kinase-inhibitory, the TNF-inhibitory and anti-arthritic effects of the compounds of the present invention:

In vitro Enzyme Assay

The ability of compounds of the invention to inhibit the enzyme p38 kinase was assessed. Activity of test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224–227 and Y. Jiang et al., *Journal of Biological Chemistry*, 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 µl of 10 mg/ml) or p38β (10 µl of 5 mg/ml) together with MKK6 (10 µl of 1 mg/ml), 'Kinase buffer' [100 µl; pH 7.4 buffer comprising Tris (50 mM), EGTA (0.1 mM), sodium orthovanadate (0.1 mM) and β-mercaptoethanol (0.1%)] and MgATP (30 µl of 50 mM Mg(OCOCH$_3$)$_2$ and 0.5 mM ATP). This produced enough activated p38 enzyme for 3 Microtiter plates.

Test compounds were solubilised in DMSO and 10 µl of a 1:10 diluted sample in 'Kinase Buffer' was added to a well in a Microtiter plate. For single dose testing, the compounds were tested at 10 µM. 'Kinase Assay Mix' [30 µl; comprising Myelin Basic Protein (Gibco BRL cat. no. 1322B-010; 1 ml of a 3.33 mg/ml solution in water), activated p38 enzyme (50 µl) and 'Kinase Buffer' (2 ml)] was then added followed by 'Labelled ATP' [10 µl; comprising 50 µM ATP, 0.1 µCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β P were incubated for 45 min. Incubation was stopped by the addition of 50 µl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In vitro Cell-based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 µg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 µl culture medium) were incubated with 20 µl of varying concentrations of test compound (triplicate cultures) or 20 µl culture medium containing 1% DMSO (control wells) for 30 minutes at 37° C. in a humidified (5%CO$_2$/95% air) incubator (Falcon 3072; 96 well flat-bottom tissue culture plates). 20 µl lipopolysaccharide [LPS *E.Coli* 0111:B4 (Sigma L-4130), final concentration 10 µg/ml] solubilised in culture medium was added to appropriate wells. 20 µl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409–413) or an inhibitor of pro TNFα convertase (for example, see McGeehan, G. M. et al. *Nature* (1994) 370, 558–561). Plates were incubated for 7 hours at 37° C. (humidified incubator) after which 100 µl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

% inhibition=(*LPS* alone−medium alone)−(test concentration−medium alone)/(*LPS* alone−medium alone)×100

(ii) Human Whole Blood

The ability of compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 µl whole blood were added to 96 well round-bottom plates (Corning 25850). Compounds were solubilised and serially diluted in RPMI 1640 medium (Gibco) supplemented with 50 units/ml penicillin, 50 µg/ml streptomycin and 2 mM glutamine, as detailed above. 20 µl of each test concentration was added to appropriate wells (triplicate cultures). 20 µl of RPMI 1640 medium supplemented with antibiotics and glutamine was added to control wells. Plates were incubated for 30 minutes at 37° C. (humidified incubator), prior to addition of 20 µl LPS (final concentration 10 µg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 µl plasma removed and stored at −70° C. (Corning 25850 plates). TNFα levels were measured by ELISA (see WO92/10190 and *Current Protocols in Molecular Biology*, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex vivo/In vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 µl of each sample was added to a set format pattern in a 96 well round bottom plate (Corning 25850). 50 µl of heparinized human blood was then added to each well, mixed and the plate was incubated for 30 min at 37° C. (humidified incubator). LPS (25 µl; final concentration 10 µg/ml) was added to the wells and incubation continued for a further 5.5 hours. Control wells were incubated with 25 µl of medium alone. Plates were then centrifuged for 10 min at 2000 rpm and 200 µl of the supernatants were transferred to a 96 well plate and frozen at −20° C. for subsequent analysis of TNF concentration by ELISA.

Data analysis by dedicated software calculates for each compound/dose:

$$\% \text{ inhibition of TNF}\alpha = \frac{\text{Mean TNF}\alpha \text{ (Controls)} - \text{Mean TNF}\alpha \text{ (Treated)}}{\text{Mean TNF}\alpha \text{ (Controls)}} \times 100$$

Alternatively, mice could be used instead of rats in the above procedure.

Test as Anti-arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.,* 146, 857.
2. Williams, R. O. et al., (1 992) *Proc. Natl. Acad. Sci.,* 89, 9784.
3. Williams. R. O. et al., (1995) *Immunology,* 84, 433.
4. Badger, M. B. et al., (1996) *The Journal of Pharmacology and Experimental Therapeutics,* 279, 1453–1461.

Although the pharmacological properties of the compounds of the Formula I vary with structural change as expected, in general a compound of the Formula I gives over 30% inhibition of p38α and/or p38β at concentrations up to 10 µM and over 30% inhibition in the PBMC test at concentrations up to 50 µM. No physiologically unacceptable toxicity was observed at the effective dose for compounds tested of the present invention.

By way of example:

N-{4-methyl-3-[3-(4-methylpiperazin-1-ylmethyl) benzamido]phenyl}furan-2-carboxamide has an $IC_{50}$ of approximately 1 µM against p38α and an $IC_{50}$ of approximately 4 µM in the PBMC test;

N-{4-methyl-3-[3-(4-methylpiperazin-1-ylmethyl) benzamido]phenyl}isoxazole-5-carboxamide has an $IC_{50}$ of approximately 0.8 µM against p38α and an $IC_{50}$ of approximately 1 µM in the PBMC test;

N-[3-(4-diethylaminomethylbenzamido)-4-methylphenyl]-2-morpholinopyridine-4-carboxamide has an $IC_{50}$ of approximately 0.2 µM against p38α, an $IC_{50}$ of less than 0.5 µM in the PBMC test and an $IC_{50}$ of approximately 10 µM in the Human Whole Blood test;

N-{3-[3-(4-methylpiperazin-1-ylmethyl)benzamido]-4-methylphenyl}-2-pyrrolidin-1-ylpyridine4-carboxamide has an $IC_{50}$ of approximately 0.1 µM against p38α and an $IC_{50}$ of less than 0.5 µM in the PBMC test; and N-{3-[3-(4-methylpiperazin-1-ylmethyl)benzamido]-4-methylphenyl}-2-morpholinopyridine-4-carboxamide has an $IC_{50}$ of approximately 0.1 µM against p38α, an $IC_{50}$ of less than 0.5 µM in the PBMC test and an $IC_{50}$ of approximately 7 µM in the Human Whole Blood test.

According to a further aspect of the invention there is provided a pharmaceutical composition which comprises an amide derivative of the Formula I or a pharmaceutically-acceptable or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula I, or a pharmaceutically-acceptable salt or in-vivo-cleavable ester thereof, as defined hereinbefore in the manufacture of a medicament for use in the treatment or medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in vivo-cleavable ester thereof In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, congestive heart failure, ischaemic heart disease or psoriasis.

In a further aspect the present invention provides a method of treating rheumatoid arthritis, asthma, irritable bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, congestive heart failure, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt or in-vivo-cleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulphoxide
DMA N,N-dimethylacetamide.

EXAMPLE 1

N-{3-[3-(4methylpiperazin-1-ylmethyl)benzamido]-4-methylphenyl}pyridine-3-carboxamide Pyridine-3-carbonyl chloride (0.09 g) was added to a stirred mixture of N-(5-amino-2-methylphenyl)-3-(4-methylpiperazin-1-ylmethyl)benzamide (0.15 g), triethylamine (0.1 g) and methylene chloride (5 ml) and the mixture was stirred at ambient temperature for 16 hours. The mixture was washed with a saturated aqueous solution of sodium bicarbonate. The organic phase was evaporated and the residue was triturated under a mixture of ethyl acetate and diethyl ether. There was thus obtained the title compound (0.056 g); Mass Spectrum: M+H$^+$444.

The N-(5-amino-2-methylphenyl)-3-(4-methylpiperazin-1-ylmethyl)benzamide used as a starting material was prepared as follows:

3-Chloromethylbenzoyl chloride (24.8 ml) was added to a stirred mixture of 2-methyl-5-nitroaniline (26.6 g), triethylamine (49 ml) and methylene chloride (800 ml) and the mixture was stirred at ambient temperature for 16 hours. The precipitate was isolated, washed with 1N aqueous hydrochloric acid solution and with diethyl ether and dried under vacuum at 40° C. There was thus obtained 3-chloromethyl-N-(2-methyl-5-nitrophenyl)-benzamide (43.5 g); NMR Spectrum: (DMSOd$_6$) 2.38 (s, 3H), 2.85 (s, 2H), 7.53–7.58 (m, 2H), 7.67 (d, 1H), 7.95(d, 1H), 8.01–8.04 (m, 2H), 8.32 (s, 1H), 10.19 (s, 1H); Mass Spectrum: M+H$^+$305.

1-Methylpiperazine (8.03 ml) was added to a stirred mixture of a portion (20 g) of the material so obtained, potassium carbonate (18.2 g) and acetone (750 ml) and the mixture was heated to 54° C. and stirred for 16 hours. The resultant solution was evaporated and the residue was dissolved in methylene chloride. The organic solution was washed with water and evaporated. There was thus obtained N-(2-methyl-5-nitrophenyl)-3-(4methylpiperazin-1-ylmethyl)benzamide (26.4 g); NMR Spectrum: (DMSOd$_6$) 2.06 (s, 3H), 2.12 (s, 3H), 2.31–2.37 (m, 8H), 3.52 (s, 2H), 7.48–7.57 (m, 3H), 7.87 (d, 2H), 8.01 (m, 1H), 8.33 (s, 1H); Mass Spectrum: M+H$^+$369.

Iron powder was added to a stirred mixture of a portion (18.0 g) of the material so obtained, ethanol (500 ml), water (50 ml) and acetic acid (10 ml). The resultant mixture was stirred and heated to reflux for 5 hours. Water (50 ml) was added and the mixture was basified by the addition of sodium carbonate. The mixture was filtered and the filtrate was evaporated to dryness. The residue was triturated under water and the resultant solid was isolated and dried under vacuum at 40° C. There was thus obtained N-(5-amino-2-methylphenyl)-3-(4-methylpiperazin-1-ylmethyl)benzamide (11.1 g); NMR Spectrum: (DMSOd$_6$) 2.03 (s, 3H), 2.13 (s, 3H), 2.24–2.4 (m, 8H), 3.5 (s, 2H), 4.86 (s, 2H) 6.35 (d, 1H), 6.57 (s, 1H), 6.86 (d, 1H), 7.40–7.48 (m, 2H), 7.78–7.83 (m, 2H), 9.57 (s, 1H); Mass Spectrum: 339.

EXAMPLE 2

Using an analogous procedure to that described in Example 1, the appropriate heteroarylcarbonyl chloride (obtained by the reaction of the corresponding heteroarylcarboxylic acid with oxalyl chloride using a conventional procedure) was reacted with the appropriate aniline to give the compounds described in Table I.

TABLE I

| No. | $R^4$ | $Q^2$ | Note |
|---|---|---|---|
| 1 | 3-(4-methylpiperazin-1-ylmethyl) | 2-furyl | a |
| 2 | 3-(4-methylpiperazin-1-ylmethyl) | 2-thienyl | b |
| 3 | 4-diethylaminomethyl | 2-thienyl | c |
| 4 | 3-morpholino | 2-thienyl | d |
| 5 | 3-(4-methylpiperazin-1-ylmethyl) | 5-(2-pyridyl)thien-2-yl | e |
| 6 | 3-(4-methylpiperazin-1-ylmethyl) | 5-isoxazolyl | f |
| 7 | 3-(4-methylpiperazin-1-ylmethyl) | 2-(4-pyridyl)thiazol-4-yl | g |
| 8 | 4-diethylaminomethyl | 2-(4-pyridyl)thiazol-4-yl | h |
| 9 | 4-diethylaminomethyl | 2-chloropyrid-4-yl | i |
| 10 | 3-morpholino | 3-pyridyl | j |
| 11 | 3-(4-methylpiperazin-1-ylmethyl) | 2-chloropyrid-4-yl | k |
| 12 | 3-(4-methylpiperazin-1-ylmethyl) | 2-benzo[b]thiophenyl | l |
| 13 | 3-(4-methylpiperazin-1-ylmethyl) | 5-benzofurazanyl | m |
| 14 | 3-(4-methylpiperazin-1-ylmethyl) | 2-quinolyl | n |
| 15 | 4-diethylaminomethyl | 2-furyl | o |
| 16 | 3-(4-methylpiperazin-1-ylmethyl) | 5-chlorothien-2-yl | p |
| 17 | 3-(4-methylpiperazin-1-ylmethyl) | 2-(3-pyridyl)thiazol-4-yl | q |
| 18 | 3-(4-methylpiperazin-1-ylmethyl) | 3-methyl-2-phenylpyrazol-4-yl | r |
| 19 | 4-diethylaminomethyl | 3-pyridyl | s |
| 20 | 3-(4-methylpiperazin-1-ylmethyl) | 2-methoxypyrid-3-yl | t |
| 21 | 3-(4-methylpiperazin-1-ylmethyl) | 5-morpholinopyrid-3-yl | u |
| 22 | 4-diethylaminomethyl | 5-morpholinopyrid-3-yl | v |
| 23 | 4-diethylaminomethyl | 2-quinolyl | w |
| 24 | 3-(4-methylpiperazin-1-ylmethyl) | 2-quinoxalinyl | x |
| 25 | 3-(4-methylpiperazin-1-ylmethyl) | 4-methyl-2-phenyl-1,2,3-triazol-5-yl | y |
| 26 | 3-(4-methylpiperazin-1-ylmethyl) | 4-dibenzofuranyl | z |
| 27 | 3-(4-methylpiperazin-1-ylmethyl) | 2-dibenzofuranyl | aa |

Notes
a The product gave the following data: Mass M+H 433.
b The product gave the following data: NMR(DMSOd$_6$)2.13(s, 3H), 2.19(s, 3H), 2.31–2.38(m, 8H), 3.52(s, 2H), 7.18–7.23(m, 2H). 7.42–7.56(m, 3H). 7.76(s, 1H), 7.82–7.78(m, 3H). 8.01(s, 1H), 9.84(s, 1H)10.2(s, 1H); Mass M+H 449.
c The product gave the following data: NMR(DMSOd$_6$)1.0(t, 6H), 2.19(s, 3H), 2.44–2.49 (m, 4H), 3.58(s, 2H), 7.19–7.24(m, 2H), 7.44(d, 2H), 7.62(d, 1H), 7.76(s, 1H), 7.82(d, 1H), 7.92(d, 2H), 8.01(d, 1H), 9.82(s, 1H), 10.11(s, 1H); Mass_M+H422.
The N-(5-amino-2-methylphenyl)-4-diethylaminomethylbenzamide used as a starting material was prepared as follows:-
4-Chloromethylbenzoyl chloride (21.4 g) was added to a stirred mixture of 2-methyl-5-nitroaniline (26.6 g), triethylamine (31.5 ml) and methylene chloride (600 ml) and the resultant mixture was stirred at ambient temperature for 16 hours. The precipitate was isolated, washed in turn with 1N aqueous hydrochloric acid solution and with diethyl ether and dried under vacuum at 40° C. There was thus obtained
N-(2-methyl-5-nitrophenyl)-4-chloromethylbenzamide (18 g); NMR(DMSOd$_6$)2.38(s, 3H), 4.83(s, 2H), 7.54–7.61(m, 3H), 7.98–8.02(m, 3H), 8.34(s, 1H), 10.15(s, 1H); MassM+ H305.
Diethylammonium chloride (64.2 g) was added to a stirred suspension of the material so obtained and potassium carbonate (18.2 g) in acetone (750 ml). The mixture was stirred and heated to 54° C. for 16 hours. The resultant mixture was evaporated and the residue was dissolved in methylene chloride. The organic solution was washed with water and evaporated. The resultant solid was isolated and dried under vacuum at 40° C. There was thus obtained N-(2- methyl-5-nitrophenyl)-4-diethylaminomethylbenzamide (18.1 g); NMR(DMSOd$_6$)0.97(t, 6H), 2.36(s, 3H), 2.44–2.49(m, 4H), 3.58(s, 2H), 7.43(d, 2H), 7.51(d, 1H), 7.94(s, 3H), 8.38(s, 1H); MassM+H342.

TABLE I-continued

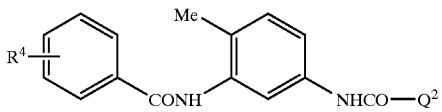

| No. | R⁴ | Q² | Note |
|-----|----|----|------|

Iron powder (29.5 g) was added to a stirred suspension of the material so obtained in ethanol (500 ml), water (50 ml) and acetic acid (10 ml). The mixture was heated to reflux and stirred for 5 hours. Water (50 ml) was added and the mixture was basified by the addition of sodium carbonate. The mixture was filtered and the filtrate was evaporated. The residue was triturated under water. The resultant solid was isolated, washed with diethyl ether and dried under vacuum at 40° C. There was thus obtained the required starting material (18 g); NMR(DMSOd₆)0.97(t, 6H), 2.02(s, 3H), 2.44–2.49(m, 4H), 3.56(s, 2H), 6.37(d, 1H), 7.59(s, 1H), 6.85(d, 1H), 7.41(d, 2H), 7.87(d, 2H), 9.53(s, 1H); Mass M+H 312.

d The product gave the following data: m.p.213–215° C.; NMR(DMSOd₆)2.18(s, 3H), 3.18(t, 4H), 3.76(t, 4H), 7.12(m, 1H), 7.18(m, 2H), 7.36(t, 1H), 7.4(d, 1H), 7.50(s, 1H), 7.55(m, 1H), 7.77(s, 1H), 7.82(d, 1H), 8.01(d, 1H), 9.81(s, 1H), 10.2(s, 1H); Mass M+H 422.

The N-(5-amino-2-methylphenyl)-3-morpholinobenzamide used as a starting material was prepared as follows:-
A mixture of ethyl 3-bromobenzoate (1.92 ml), morpholine (1.25 ml), 2,2'-bis (diphenylphosphino)-1,1'-binaphthyl (0.336 g), sodium tert-butoxide (1.615 g) and tris (dibenzylideneacetone)dipalladium(0) (0.33 g) and toluene (25 ml) was stirred and heated to 90° C. for 18 hours under argon. The reaction mixture was allowed to cool to ambient temperature and extracted with 1N aqueous hydrochloric acid. The aqueous phase was basified with concentrated sodium hydroxide solution and extracted with ethyl acetate. The organic phase was dried over magnesium sulphate and evaporated. The residual oil was purified by column chromatography on silica gel using a 47:3 mixture of methylene chloride and methanol as eluent. There was thus obtained N-(3-morpholinobenzoyl)morpholine (0.45 g).

A mixture of the material so obtained, 5M sodium hydroxide solution (2.5 ml) and butanol (2 ml) was stirred and heated to 115° C. for 18 hours. The mixture was evaporated and the residue was acidified by the addition of 1N aqueous hydrochloric acid solution (12.5 ml). The resultant precipitate was isolated, washed with water and dried to give 3-morpholinobenzoic acid (0.15 g); NMR(DMSOd₆)3.1(t, 4H), 3.73(t, 4H), 7.19(d, 1H), 7.32(d, 1H), 7.38(t, 1H), 7.42(s, 1H).

Oxalyl chloride (0.14 ml) was added to a solution of 3-morpholinobenzoic acid (0.28 g) in methylene chloride (10 ml) which contained DMF (2 drops). The reaction mixture was stirred for 18 hours at ambient temperature. The mixture was evaporated and azeotroped with toluene to give 3-morpholinobenzoyl chloride (0.3 g); MassM+H222.

After repetition of the previous reactions, 3-morpholinobenzoyl chloride (1.23 g) was added to a stirred mixture of 2-methyl-5-nitroaniline (0.7 g), triethylamine (1.8 ml) and methylene chloride (15 ml) and the reaction mixture was stirred at ambient temperature for 16 hours. The mixture was diluted with methylene chloride and washed in turn with water and with a saturated aqueous sodium bicarbonate solution. The organic phase was dried over magnesium sulphate and evaporated. The residue was stirred under diethyl ether (40 ml) for 2 hours and the resultant solid was isolated and dried to give N-(2-methyl-5-nitrophenyl)-3-morpholinobenzamide (1.21 g); m.p.155–156° C; NMR (DMSOd₆)1.97(s, 3H), 3.18(t, 4H), 3.76(t, 3H), 7.16(d, 1H), 7.38(m, 2H); 7.5(s, 1H), 7.54(d, 1H), 8.0(m, 1H), 8.3(d, 1H), 10.02(s, 1H); MassM−H340.

The material so obtained was dissolved in a mixture of ethanol (50 ml) and methanol (50 ml) and hydrogenated under an atmosphere of hydrogen at ambient temperature using 10% palladium-on-carbon (0.15 g) as catalyst. After the cessation of hydrogen uptake, the catalyst was filtered off and the residue was washed with methylene chloride. The combined filtrates were evaporated to give the required starting amine as a solid (0.89 g); NMR(DMSOd₆)2.0(s, 3H), 3.22(t, 4H), 3.62(s, 2H), 3.86(t, 4H), 6.42(m, 1H), 6.97(d, 1H), 7.08(m, 1H), 7.22(m, 1H), 7.38(t, 1H), 7.46(d, 1H), 7.56(d, 1H), 7.62(s, 1H), MassM+H312.

e The product gave the following data: Mass M+H 526.

The 5-(2-pyridyl)thiophene-2-carbonyl chloride used as a starting material was prepared by the reaction of 5-(2-pyridyl)thiophene-2-carboxylic acid with oxalyl chloride using a conventional procedure.

f The reaction mixture was heated to 70° C. for 16 hours. The product gave the following data: NMR(DMSOd₆)2.19(s, 3H), 2.21(s, 3H), 2.25–2.37(m, 8H), 3.53(s, 2H), 7.23–7.27(d, 3H), 7.44–7.58(m, 3H), 7.81(s, 1H), 7.85–7.87(m, 2H), 8.79(s, 1H), 9.91(s, 1H), 10.71(s, 1H); Mass M+H 434.

g The product gave the following data: Mass M +H 527.

The 2-(4-pyridyl)thiazole-4-carbonyl chloride used as a starting material was prepared by the reaction of 2-(4-pyridyl)thiazole-4-carboxylic acid with oxalyl chloride using a conventional procedure.

h The product gave the following data: Mass M+H 500.

TABLE I-continued

[Structure: R⁴-substituted phenyl-CONH-(Me-substituted phenyl)-NHCO-Q²]

| No. | R⁴ | Q² | Note |
| --- | --- | --- | --- | i After the conventional work-up, the reaction mixture residue was purified by column chromatography on an ion exchange column (isolate SCX column from International Sorbent Technology Limited, Hengoed, Mid-Glamorgan, UK) using a 99:1 mixture of methanol and a saturated aqueous ammonium hydroxide solution as eluent. The product so obtained gave the following data: NMR(DMSOd$_6$)1.0(t, 6H), 2.2(s, 3H), 2.44–2.49(m, 4H), 3.6(s, 2H), 7.24(d, 1H), 7.44(d, 2H), 7.58(d, 1H), 7.82 (s, 1H), 7.85(d, 1H), 7.92(d, 2H), 7.98(s, 1H), 8.59(d, 1H), 9.83(s, 1H), 10.54(s, 1H); Mass M+H 451.

j The product gave the following data: m.p.223–227° C.; NMR(DMSOd$_6$)2.19(s, 3H), 3.18(t, 4H), 3.76(t, 4H), 7.12(d, 2H), 7.22(d, 1H), 7.37(m, 1H), 7.44(s, 1H), 7.52(t, 2H), 7.8(s, 1H), 8.28(d, 1H), 8.75(d, 1H), 9.1(s, 1H), 10.4(s, 1H).

k After the conventional work-up, the reaction mixture was purified by column chromatography on an isolute SCX ion exchange column using a 99:1 mixture of methanol and a saturated aqueous ammonium hydroxide solution as eluent. The product so obtained gave the following data: NMR(DMSOd$_6$)2.13(s, 3H), 2.23(s, 3H), 2.32–2.38(m, 8H), 3.52 (s, 2H), 7.25(d, 1H). 7.45–7.60(m, 3H). 7.81–7.86(m, 4H), 7.99(s, 1H). 8.6(d, 1H), 9.89 (s, 1H)10.54(s, 1H); Mass M+H 478.

l The product so obtained gave the following data: Mass M+H 499.

m The product so obtained gave the following data: Mass M+H 485.

n The product so obtained gave the following data: Mass M+H 494.

o The product so obtained gave the following data: Mass M+H 406.

p The product so obtained gave the following data: Mass M+H 483.

The 5-chlorothiophene-2-carbonyl chloride used as a starting material was prepared by the reaction of 5-chlorothiophene-2-carboxylic acid with oxalyl chloride using a conventional procedure.

q After the conventional work-up, the reaction mixture residue was purified by column chromatography on silica using increasingly polar mixtures of methylene chloride and methanol as eluent. The product so obtained gave the following data: Mass M+H 527. The 2-(3-pyridyl)thiazole-4-carbonyl chloride used as a starting material was prepared by the reaction of 2-(3-pyridyl)thiazole-4-carboxylic acid with oxalyl chloride using a conventional procedure.

r After the conventional work-up, the reaction mixture residue was purified by column chromatography on silica using increasingly polar mixtures of methylene chloride and methanol as eluent. The product so obtained gave the following data: Mass M+H 523. The 3-methyl-2-phenylpyrazole-4-carbonyl chloride used as a starting material was prepared by the reaction of 3-methyl-2-phenylpyrazole-4-carboxylic acid with oxalyl chloride using a conventional procedure.

s The product so obtained gave the following data: Mass M+H 417.

t The product was obtained as an oil and gave the following data: Mass M+H 474. The 2-methoxypyridine-3-carbonyl chloride used as a starting material was prepared by the reaction of 2-methoxypyridine-3-carboxylic acid with oxalyl chloride using a conventional procedure.

u After the conventional work-up, the reaction mixture residue was purified by column chromatography on an isolute SCX ion exchange column using a 99:1 mixture of methanol and a saturated aqueous ammonium hydroxide solution as eluent. The product so obtained gave the following data: NMR(DMSOd$_6$)2.2(s, 6H), 2.31–2.42(m, 8H), 3.2–3.27 (m, 4H), 3.54(s, 2H), 3.76(m, 4H), 7.22(m, 1H), 7.46(m, 1H), 7.58(d, 1H), 7.68–7.9(m, 4H), 8.53(m, 3H), 9.88(s, 1H), 10.28(s, 1H); Mass M+ H 529. The 5-morpholinopyridine-3-carbonyl chloride used as a starting material was prepared by the reaction of 5-morpholinopyridine-3-carboxylic acid with oxalyl chloride using a conventional procedure.

The 5-morpholinopyridine-3-carboxylic acid used as a starting material was obtained as follows:-
N,N-Dimethylformamide di-tert-butyl acetal (14.3 ml) was added dropwise to a stirred solution of 5-bromopyridine-3-carboxylic acid (3.0 g) in toluene (30 ml) which had been heated to reflux. The mixture was heated to reflux for 2 hours. The mixture was allowed to cool to ambient temperature and was washed in turn with water and with a saturated aqueous solution of sodium bicarbonate. The organic phase was evaporated and the residue was triturated under a mixture of isohexane and ethyl acetate. There was thus obtained tert-butyl 5-bromopyridine-3-carboxylate (1.31 g). The filtrate was evaporated and the residue was purified by column chromatography on silica using a 5:1 mixture of isohexane and ethyl acetate as eluent. There was thus obtained a second portion of tert-butyl 5-bromopyridine-3-carboxylate (1.71 g).

Morpholine (0.55 ml) was added to a stirred mixture of tert-butyl 5-bromopyridine-3-carboxylate (0.8 g), tris(dibenzylideneacetone)dipalladium(0) (0.13 g), (S)-(−)-2,2'-bis (diphenylphosphino)-1,1'-binaphthyl (0.08 g), sodium tert-butoxide (0.36 g) and toluene (10 ml). The mixture was stirred and heated to 90° C. for 16 hours. The mixture was evaporated and the residue was purified by column chromatography using increasingly polar mixtures of isohexane and ethyl acetate (a solvent gradient from 5:1 to 2:1 mixtures) as eluent. There was thus obtained tert-butyl 5-morpholinopyridine-3-carboxylate (0.5 g); NMR(DMSOd$_6$)1.54(s, 9H), 3.21(m, 4H), 3.75(m, 4H), 7.61(s, 1H), 8.45(s, 1H), 8.49(s, 1H)

TABLE I-continued

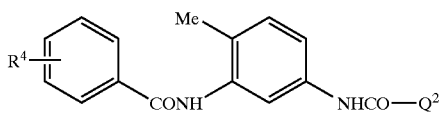

| No. | R⁴ | Q² | Note |
|---|---|---|---|

A mixture of tert-butyl 5-morpholinopyridine-3-carboxylate (0.49 g), water (0.5 ml) and trifluoroacetic acid (5 ml) was stirred at ambient temperature for 3 hours. The solvent was evaporated and the residue was triturated under a mixture of diethyl ether and ethyl acetate. There was thus obtained 5-morpholinopyridine-3-carboxylic acid (0.37 g); NMR (DMSOd$_6$)3.27(m, 4H), 3.75(m, 4H), 7.82(s, 1H), 8.52(s, 2H).

v After the conventional work-up, the reaction mixture residue was purified by column chromatography on an isolate SCX ion exchange using a 99:1 mixture of methanol and a saturated aqueous ammonium hydroxide solution as eluent. The product so obtained gave the following data: NMR(DMSO$_6$)0.99(t, 3H), 2.49(m, 2H), 3.26(m, 4H), 3.61(s, 2H), 3.76(m, 4H), 7.02(d, 1H), 7.45(d, 2H), 7.58(d, 1H), 7.77(s, 1H), 7.8(s, 1H), 7.91(m, 2H), 8.46(s, 1H), 8.52(s, 1H), 9.83(s, 1H), 10.28(s, 1H); Mass M+H 502.

w The product so obtained gave the following data: Mass M+H 467.

x The product so obtained gave the following data: NMR(DMSOd$_6$)2.13(s, 3H), 2.22(s, 3H), 2.35(m, 8H), 3.52(s, 2H), 7.29(d, 1H), 7.48(m, 2H), 7.74(d, 1H), 7.87(m, 2H), 7.98 (m, 3H), 8.3(m, 2H), 9.53(s, 1H), 9.92(s, 1H), 10.2(s, 1H); Mass M+H 495.

y The product so obtained gave the following data: Mass M+H 524.

z The product so obtained gave the following data: NMR(DMSOd$_6$)2.15(s, 3H), 2.22(s, 3H), 2.3–2.5(m, 8H), 3.55(s, 2H), 7.3(d, 1H), 7.4–7.65(m, 6H), 7.8–7.95(m, 5H), 8.2(d, 1H), 8.35(d, 1H), 9.95(s, 1H), 10.42(s, 1H); Mass M+H 533.

The dibenzofuran-4-carbonyl chloride used as a starting material was obtained by the reaction of dibenzofuran-4-carboxylic acid (prepared by the procedure disclosed in J. Chem. Soc. Perkin I, 1998, 457–465) and oxalyl chloride using a conventional procedure.

aa The product so obtained gave the following data: NMR(DMSOd$_6$)2.2(s, 3H), 2.4–2.6 (m, 11H), 3.6(s, 2H), 7.25(d, 1H), 7.4–7.65(m, 5H), 7.7–7.85(m, 2H), 7.85–7.95(m, 3H), 8.15(d, 1H), 8.25(d, 1H), 8.8(s, 1H), 9.9(s, 1H), 10.37(s, 1H); Mass M+H 533.

EXAMPLE 3

N-{3-[3-(4-methylpiperazin-1-ylmethyl)benzamido]-4-methylphenyl}-2-pyrrolidin-1-ylpyridine-4-carboxamide Pyrrolidine (0.3 g) was added to a stirred mixture of N-{3-[3-(4-methylpiperazin-1-ylmethyl)benzamido]-4-methylphenyl}-2-chloropyridine-4-carboxamide (0.5 g) and DMSO (5 ml) and the mixture was stirred and heated to 120° C. for 16 hours. The resultant solution was cooled to ambient temperature and poured into water and extracted with methylene chloride. The organic phase was evaporated and the residue was purified by column chromatography on an isolate SCX ion exchange column using a 99:1 mixture of methanol and a saturated aqueous ammonium hydroxide solution as eluent. There was thus obtained the title compound (0.014 g); Mass Spectrum: M+H⁺513.

EXAMPLE 4

N-{3-[3-(4-methylpiperazin-1-ylmethyl)benzamido]-4-methylphenyl}-2-morpholinopyridine-4-carboxamide Using an analogous procedure to that described in Example 3, a mixture of N-{3-[3-(4-methylpiperazin-1-ylmethyl)benzamido]-4-methylphenyl}-2-chloropyridine-4-carboxamide (0.5 g) and morpholine (5 ml) was stirred and heated to 110° C. for 16 hours. The resultant solution was cooled to ambient temperature and poured into water and extracted with methylene chloride. The organic phase was evaporated and the residue was purified by column chromatography on an isolate SCX ion exchange column using a 99:1 mixture of methanol and a saturated aqueous ammonium hydroxide solution as eluent. There was thus obtained the title compound (0.023 g); Mass Spectrum: M+H⁺529.

EXAMPLE 5

N-[3-(4diethylaminomethylbenzamido)-4-methylphenyl]-2-pyrrolidin-1-ylpyridine-4-carboxamide Using an analogous procedure to that described in Example 3, a mixture of N-[3-(4-diethylaminomethylbenzamido)-4-methylphenyl]-2-chloropyridine-4-carboxamide (0.5 g) and pyrrolidine (5 ml) was stirred and heated to 80° C. for 16 hours. The resultant solution was cooled to ambient temperature and poured into water. The resultant solid was isolated, washed with diethyl ether and dried under vacuum at 40° C. There was thus obtained the title compound (0.021 g); NMR Spectrum: (DMSOd$_6$) 1.0 (t, 6H), 1.95 (m, 4H), 2.2 (s, 3H), 2.44–2.49 (m, 4H), 3.42–3.5 (m, 4H), 3.6 (s, 2H), 6.86 (s, 1H), 6.96 (d, 1H), 7.22 (d, 1H), 7.58 (d, 1H), 7.79 (s, 1H), 7.92 (d, 2H), 8.18 (d, 1H), 9.83 (s, 1H), 10.28 (s, 1H); Mass Spectrum: M+H⁺ 486.

EXAMPLE 6

N-[3-(4-diethylaminomethylbenzamido)-4-methylphenyl]-2-morpholinopyridine-4-carboxamide Using an analogous procedure to that described in Example 3, a mixture of N-[3-(4diethylaminomethylbenzamido)-4-methylphenyl]-2-chloropyridine-4-carboxamide (0.5 g) and morpholine (5 ml) was stirred and heated to 110° C. for 16 hours. The resultant solution was cooled to ambient temperature and poured into water. The resultant solid was isolated, washed with diethyl ether and dried under vacuum at 40° C. There was thus obtained the title compound (0.021 g); NMR Spectrum: (DMSOd$_6$) 1.0 (t, 6H), 2.2 (s, 3H), 2.44–2.49 (m, 4H), 3.42–3.57 (m. 4H), 3.6 (s, 2H), 3.65–3.63 (m, 4H), 7.08 (d, 1H), 7.2–7.25 (m, 2H), 7.45 (d, 2H), 7.58 (d, 1H), 7.79 (s, 1H), 7.92 (d, 2H), 8.26 (d, 1H), 9.83 (s, 1H), 10.28 (s, 1H); Mass Spectrum: M+H⁻ 502.

EXAMPLE 7

N-{3-[3-(2-pyrrolidin-1-ylethoxy)benzamido]-4-methylphenyl}quinoline-6-carboxamide A mixture of N-[3-(3-hydroxybenzamido)-4-methylphenyl]quinoline-6-carboxamide (0.168 g), 2-pyrrolidin-1-ylethyl chloride hydrochloride salt (0.086 g), potassium carbonate (0.233 g) and DMA (6 ml) was stirred and heated to 40° C. for 18 hours. The mixture was allowed to cool to ambient temperature and poured into water (100 ml). The resultant precipitate was isolated, washed in turn with water and with diethyl ether and dried under vacuum at 60° C. There was thus obtained the title compound (0.127 g); m.p. 183–1840° C.; NMR Spectrum: ($DMSOd_6$) 1.65 (t, 4H), 2.2 (s, 3H), 2.5 (m, 4H), 2.8 (t, 2H), 4.17 (t, 2H), 7.16 (m, 1H), 7.25 (d, 1H), 7.41 (t, 1H), 7.56 (m, 2H), 7.62 (m, 2H), 7.87 (d, 1H), 8.11 (d, 1H), 8.24 (m, 1H), 8.51 (m, 1H), 8.61 (d, 1H), 8.99 (s, 1H), 9.9 (s, 1H), 10.48 (s, 1H); Mass Spectrum: M+H$^+$ 495.

The N-[3-(3-hydroxybenzamido)-4-methylphenyl]quinoline-6-carboxamide used as a starting material was prepared as follows:

Oxalyl chloride (1.76 g) was added to a stirred mixture of quinoline-6-carboxylic acid (2 g), DMF (3 drops) and methylene chloride (60 ml) and the mixture was stirred at ambient temperature for 4 hours. The solvent was evaporated and the residue was dissolved in methylene chloride (60 ml) and added dropwise to a stirred mixture of 4-methyl-3-nitroaniline (1.46 g), triethylamine (2.82 ml) and methylene chloride (60 ml). The mixture was stirred at ambient temperature for 18 hours. The reaction mixture was washed in turn with water and with a saturated aqueous sodium bicarbonate solution. The organic phase was dried over magnesium sulphate and evaporated and the residue was triturated under diethyl ether. The resultant solid was dried under vacuum at 60° C. There was thus obtained N-(4-methyl-3-nitrophenyl)quinoline-6-carboxamide (1.59 g); m.p. 215–216° C.; NMR Spectrum: ($DMSOd_6$) 7.48 (s, 6H), 7.64 (m, 1H), 8.03 (m, 1H), 8.15 (d, 1H), 8.29 (m, 1H), 8.56 (m, 2H), 8.68 (s, 1H); 9.02 (m, 1H), 10.84 (s, 1H); Mass Spectrum: M–H$^-$ 306.

Iron powder (1.98 g) was added to a stirred mixture of a portion (0.75 g) of the material so obtained, acetic acid (0.67 ml), water (3.33 ml) and ethanol (21.7 ml) and the resultant mixture was stirred and heated to reflux for one hour. The mixture was poured onto an excess sodium carbonate and filtered. The filtrate was evaporated and the residue was dissolved in methylene chloride. The solution was washed with water, dried over magnesium sulphate and evaporated. The resultant solid was dried under vacuum at 60° C. There was thus obtained N-(3-amino-4-methylphenyl)quinoline-6-carboxamide (0.45 g); m.p. 166–167° C.; NMR Spectrum: ($DMSOd_6$) 2.02 (s, 3H), 4.85 (s, 2H), 6.87 (m, 2H), 7.17 (s, 1H); 7.61 (m, 1H), 8.09 (d, 1H), 8.22 (m, 1H), 8.49 (d, 1H), 8.57 (d, 1H). 8.97 (m, 1H), 10,15 (s, 1H); Mass Spectrum: M+H$^+$ 278.

Oxalyl chloride (1.81 g) was added to a stirred solution of 3-benzyloxybenzoic acid (2.72 g) in methylene chloride (100 ml) containing DMF (3 drops) and the resultant solution was stirred at ambient temperature for 3 hours. The solvent was evaporated and the residue was dissolved in methylene chloride (40 ml). The solution was added dropwise to a stirred mixture of N-(3-amino-4-methylphenyl)quinoline-6-carboxamide (2.75 g), triethylamine (1.8 ml) and methylene chloride (60 ml). The mixture was stirred at ambient temperature for 18 hours. The reaction mixture was washed in turn with water and with a dilute aqueous sodium hydroxide solution. The organic phase was dried over magnesium sulphate and evaporated and the residue was triturated under diethyl ether. The resultant solid was dried under vacuum at 60° C. There was thus obtained N-[3-(3-benzyloxybenzamido)-4-methylphenyl]quinoline-6-carboxamide (3.56 g); m.p. 185–186° C.; NMR Spectrum: ($DMSOd_6$) 2.2 (s, 3H), 5.19 (s, 2H), 7.23 (m, 2H), 7.38 (m, 6H), 7.6 (m, 4H),7.87 (d, 1H), 8.13 (d, 1H), 8.24 (m, 1H), 8.52 (m, 2H), 8.61 (d, 1H); 8.99 (m, 1H), 9.9 (s, 1H), 10.84 (s, 1H); Mass Spectrum: M+H$^+$ 488.

Ammonium formate (1.52 g) was added to a stirred mixture of a portion (2.35 g) of the material so obtained, 10% palladium-on-carbon catalyst (0.47 g) and methanol (470 ml). The mixture was stirred and heated to reflux for one hour. The reaction mixture was allowed to cool to ambient temperature and was filtered. The filtrate was evaporated. The residual solid was stirred in water for one hour, reisolated, washed in turn with water and with diethyl ether and dried under vacuum at 60° C. There was thus obtained the required starting material; NMR Spectrum: ($DMSOd_6$) 2.2 (s, 3H), 6.95 (m, 2H), 7.32 (m, 4H), 7.61 (m, 2H), 7.85 (d, 1H), 8.12 (d, 1H), 8.23 (d, 1H), 8.51 (m, 1H), 8.61 (d, 1H), 8.99 (m, 1H), 9.79 (s, 1H), 10.48 (s, 1H); Mass Spectrum: M–H$^-$ 396.

EXAMPLE 8

N-{3-[3-(2-piperidinoethoxy)benzamido]-4-methylphenyl}quinoline-6-carboxamide

Using an analogous procedure to that described in Example 7, N-[3-(3-hydroxybenzamido)-4-methylphenyl]quinoline-6-carboxamide was reacted with 2-piperidinoethyl chloride to give the title compound in 55% yield; NMR Spectrum: ($DMSOd_6$) 1.39 (m, 2H), 1.49 (s, 4H), 2.2 (s, 3H), 2.42 (s, 4H), 2.65 (t, 2H), 4.15 (t, 2H), 7.15 (m, 1H), 7.26 (d, 1H), 7.41 (t, 1H), 7.55 (m, 2H), 7.62 (m,2H),7.86 (s, 1H), 8.12 (d, 1H), 8.24 (m, 1H), 8.52 (m, 1H), 8.61 (s, 1H), 8.99 (d, 1H), 9.89 (s, 1H), 10.48 (s, 1H); Mass Spectrum: M+H$^+$ 509.

EXAMPLE 9

N-{3-[3-(2-pyridylmethoxy)benzamido]-4-methylphenyl}quinoline-6-carboxamide

Using an analogous procedure to that described in Example 7, N-[3-(3-hydroxybenzamido)-4-methylphenyl]quinoline-6-carboxamide was reacted with 2-chloromethylpyridine to give the title compound in 58% yield; NMR Spectrum: ($DMSOd_6$) 2.2 (s, 3H), 5.26 (s, 2H), 7.23 (m, 2H), 7.33 (t, 1H), 7.43 (t, 1H), 7.57 (t, 1H), 7.61 (m, 4H), 7.82 (m, 1H), 7.85 (d, 1H), 8.12 (d, 1H), 8.25 (d, 1H), 8.51 (d, 1H), 8.58 (d, 1H), 8.61 (s, 1H), 8.99 (d, 1H), 9.9 (s, 1H), 10.48 (s, 1H); Mass Spectrum: M+H$^+$ 489.

EXAMPLE 10

Using an analogous procedure to that described in Example 3, the appropriate chloropyridinecarboxamide was reacted with the appropriate heterocycle to give the compounds described in Table II.

TABLE II

[Structure: R⁴-substituted phenyl-CONH-(methyl)phenyl-NHCO-Q²]

| No. | R⁴ | Q² | Note |
|---|---|---|---|
| 1 | 3-(4-methylpiperazin-1-ylmethyl) | 4-morpholinopyrid-2-yl | a |
| 2 | 4-diethylaminomethyl | 4-morpholinopyrid-2-yl | b |
| 3 | 3-(4-methylpiperazin-1-ylmethyl) | 2-piperazin-1-ylpyrid-4-yl | c |
| 4 | 3-(4-methylpiperazin-1-ylmethyl) | 2-piperidinopyrid-4-yl | d |
| 5 | 3-(4-methylpiperazin-1-ylmethyl) | 2-[(S)-(+)-2-hydroxymethyl-pyrrolidin-1-yl]pyrid-4-yl | e |
| 6 | 3-(4-methylpiperazin-1-ylmethyl) | 2-[(R)-(−)-2-hydroxymethyl-pyrrolidin-1-yl]pyrid-4-yl | f |
| 7 | 3-(4-methylpiperazin-1-ylmethyl) | 2-(3-hydroxypyrrolidin-1-yl)pyrid-4-yl | g |
| 8 | 4-diethylaminomethyl | 2-[(S)-(+)-2-hydroxymethyl-pyrrolidin-1-yl]pyrid-4-yl | h |
| 9 | 4-diethylaminomethyl | 2-[(R)-(−)-2-hydroxymethyl-pyrrolidin-1-yl]pyrid-4-yl | i |
| 10 | 3-(4-methylpiperazin-1-ylmethyl) | 2-(4-hydroxypiperidin-1-yl)pyrid-4-yl | j |

Notes a The reactants, N-{3-[3-(4-methylpiperazin-1-ylmethyl)benzamido]-4-methylphenyl}-4-chloropyridine-2-carboxamide (0.05 g) and morpholine (3 ml), were stirred and heated to 100° C. for 16 hours. The resultant solution was cooled to ambient temperature and poured into water and extracted with methylene chloride. The organic phase was evaporated and the residue was purified by reversed-phase column chromatography using decreasingly polar mixtures of water and methanol as eluent. There was thus obtained the required product (0.016 g); NMR(DMSOd$_6$)2.19(s, 3H), 2.2(s, 3H), 2.31–2.5(m, 8H), 3.36(m, 4H), 3.53(s, 2H), 3.73(m, 4H), 7.07(d, 1H), 7.07(d, 1H), 7.22(d, 1H), 7.42–7.58(m, 3H), 7.62(d, 1H), 7.86(m, 2H), 7.94(s, 1H), 8.3(d, 1H), 9.9(s, 1H), 10.47(s, 1H); Mass M+H 529.
The N-{3-[3-(4-methylpiperazin-1-ylmethyl)benzamido]-4-methylphenyl}-4-chloropyridine-2-carboxamide used as a starting material was obtained as follows:-
Using an analogous procedure to that described in Example 1, 4-chloropyridine-2-carbonyl chloride (prepared by the reaction of 4-chloropyridine-2-carboxylic acid and oxalyl chloride) was reacted with N-(5-amino-2-methylphenyl-3-(4-methylpiperazin-1-ylmethyl)benzamide. The organic phase was evaporated and the residue was purified using an isolute SCX ion exchange column and a 99:1 mixture of methanol and a saturated aqueous ammonium hydroxide solution as eluent. The product so obtained was triturated under a mixture of diethyl ether and ethyl acetate. There was thus obtained the required starting material in 25% yield; NMR(DMSOd$_6$)2.15(s, 3H), 2.2(s, 3H), 2.31–2.4(m, 8H), 3.52(s, 2H), 7.23(d, 1H), 7.47(m, 2H), 7.65(d, 1H), 7.84(m, 4H), 7.96(s, 1H), 8.12(s, 1H), 8.7(d, 1H), 9.92(s, 1H), 10.64(s, 1H); Mass M+H 478 and 480.
b The reactants, N-[3-(4-diethylaminomethylbenzamido)-4-methylphenyl]-4-chloropyridine-2-carboxamide (0.05 g) and morpholine (3 ml), were stirred and heated to 100° C. for 16 hours. The resultant solution was cooled to ambient temperature and poured into water and extracted with methylene chloride. The organic phase was evaporated and the residue was purified by reversed-phase column chromatography using decreasingly polar mixtures of water and methanol as eluent.
The product so obtained was triturated under a mixture of diethyl ether and ethyl acetate. There was thus obtained the required product (0.035 g); NMR(DMSOd$_6$) 0.98(t, 3H), 2.19(s, 3H), 2.43–2.88(m, 2H), 3.37(m, 4H), 3.59(s, 2H), 3.72(m, 4H), 7.04(m, 1H), 7.22(d, 1H), 7.45(d, 2H), 7.53(s, 1H), 7.62(d, 1H), 7.93(m, 3H), 8.3(d, 1H), 9.84(s, 1H), 10.47(s, 1H); Mass M+H 502.
The N-[3-(4-diethylaminomethylbenzamido)-4-methylphenyl]-4-chloropyridine-2-carboxamide used as a starting material was prepared as follows:-
Using the analogous procedure to that described in Example 1, N-(5-amino-2-methylphenyl)-4-diethylaminomethylbenzamide was reacted with 4-chloropyridine-2-carbonyl chloride and the reaction mixture was worked-up using an analogous procedure to that described in the portion of Note a) above which is concerned with the preparation of starting materials.
c The reactants, N-{3-[3-(4-methylpiperazin-1-ylmethyl)benzamido]-4-methylphenyl}-2-chloropyridine-4-carboxamide (0.05 g) and piperazine (1 g), were stirred and heated to 100° C. for 16 hours. The resultant solution was cooled to ambient temperature and poured into water and extracted with methylene chloride. The organic phase was evaporated and the residue was purified using an isolute SCX ion exchange column and a 99:1 mixture of methanol and a saturated aqueous ammonium hydroxide solution as eluent. There was thus obtained the required product (0.014 g); Mass M+H 528.
d The reactants, N-{3-[3-(4-methylpiperazin-1-ylmethyl)benzamido]-4-methylphenyl}-2-chloropyridine-4-carboxamide (0.05 g) and piperidine (3 ml), were stirred and heated to 100° C. for 16 hours. The resultant solution was cooled to

TABLE II-continued $$R^4 \overset{}{\underset{}{\bigcirc}} \text{CONH} \overset{Me}{\underset{}{\bigcirc}} \text{NHCO—}Q^2$$

| No. | R⁴ | Q² | Note |
|-----|----|----|------| ambient temperature and poured into water and extracted with methylene chloride. The organic phase was evaporated and the residue was purified using an isolute SCX ion exchange column and a 99:1 mixture of methanol and a saturated aqueous ammonium hydroxide solution as eluent. There was thus obtained the required product (0.013 g); Mass M+H 527.

e The reactants, N-{3-[3-(4-methylpiperazin-1-ylmethyl)benzamido]-4-methylphenyl}-2-chloropyridine-4-carboxamide (0.2 g) and (S)-(+)-2-pyrrolidine-methanol (0.6 g), were stirred and heated to 105° C. for 16 hours. The resultant solution was cooled to ambient temperature and poured into water and extracted with methylene chloride. The organic phase was evaporated and the residue was purified by reversed-phase column chromatography using decreasingly polar mixtures of water and methanol as eluent. The product so obtained was triturated under a mixture of diethyl ether and ethyl acetate. There was thus obtained the required product (0.053 g); NMR(CDCl₃)1.9–2.2(m, 4H), 2.2–2.4(d, 6H), 2.4–2.6(m, 8H), 3.3–3.8(m, 6H), 4.2–4.4(m, 1H), 6.9(m, 2H), 7.22(m, 1H), 7.48(m, 2H), 7.65–7.8(m, 2H), 7.85(m, 2H), 8.05(s, 1H); Mass M+H 543.

f The reactants, N-{3-[3-(4-methylpiperazin-1-ylmethyl)benzamido]-4-methylphenyl}-2-chloropyridine-4-carboxamide (0.2 g) and (R)-(–)-2-pyrrolidine-methanol (0.5 ml), were stirred and heated to 105° C. for 16 hours and the work-up was as described in Note e). There was thus obtained the required product (0.04 g); NMR(CDCl₃)1.95–2.15(m, 4H), 2.3(d, 6H), 2.4–2.6(m, 8H), 3.4–3.8(m, 6H), 4.25–4.35(m, 1H), 6.85–6.9(m, 2H), 7.22(m, 1H), 7.48(m, 2H), 7.65–7.8(m, 3H), 7.85(s, 1H), 8.15(m, 2H); Mass M+H 543.

g The reactants, N-{3-[3-(4-methylpiperazin-1-ylmethyl)benzamido]-4-methylphenyl}-2-chloropyridine-4-carboxamide (0.2 g) and 3-hydroxypyrrolidine (0.5 ml), were stirred and heated to 105° C. for 16 hours and the work-up was as described in Note e). There was thus obtained the required product (0.078 g); NMR(CDCl₃)2.0–2.2(m, 2H), 2.3(s, 6H), 2.4–2.6(m, 8H), 2.8–3.0(m, 1H), 3.4–3.7(m, 7H), 4.58(m, 1H), 6.75(s, 1H), 6.8(m, 1H), 7.4(m, 1H), 7.53(m, 1H), 7.65(m, 1H), 7.75(m, 1H), 7.85(m, 2H), 8.1(s, 1H), 8.2(d, 1H), 8.35(s, 1H); Mass M+H 529.

h The reactants, N-[3-(4-diethylaminomethylbenzamido)-4-methylphenyl]-4-chloropyridine-2-carboxamide (0.2 g) and (S)-(+)-2-pyrrolidinemethanol (0.6 g), were stirred and heated to 105° C. for 16 hours and the work-up was as described in Note e). There was thus obtained the required product (0.086 g); NMR(CDCl₃)1.05(t, 6H), 2.0–2.2(m, 4H), 2.3(s, 3H), 2.5–2.6(m, 4H), 3.3–3.45(m, 1H), 3.55(m, 1H), 3.6–3.7(m, 3H), 3.75(m, 2H), 4.3(m, 1H), 6.95(m, 2H), 7.22(d, 2H), 7.45(m, 2H), 7.75(m, 2H), 7.85(m, 3H), 8.0–8.2(m, 3H); Mass M+H 516.

i The reactants, N-[3-(4-diethylaminomethylbenzamido)-4-methylphenyl]-4-chloropyridine-2-carboxamide (0.2 g) and (R)-(–)-2-pyrrolidinemethanol (0.5 ml), were stirred and heated to 105° C. for 16 hours and the work-up was as described in Note e). There was thus obtained the required product (0.089 g); NMR(CDCl₃)1.05(t, 6H), 1.95–2.2(m, 4H), 2.3(s, 3H), 2.55(m, 4H), 2.95(m, 1H), 3.4(m, 1H), 3.45–3.6(m, 1H), 3.6–3.7 (m, 3H), 3.75(m, 2H), 4.3(m, 1H), 6.85 (m, 2H), 7.22(m, 1H), 7.45(m, 2H), 7.7–7.85(m, 4H), 8.15(m, 3H); Mass M+H 516.

j The reactants, N-{3-[3-(4-methylpiperazin-1-ylmethyl)benzamido]-4-methylphenyl}-2-chloropyridine-4-carboxamide (0.2 g) and 3-hydroxypiperidine (1 g), were stirred and heated to 105° C. for 16 hours and the work-up was as described in Note e). There was thus obtained the required product (0.066 g); NMR(CDCl₃) 1.5–1.8(m, 2H), 1.98(m, 2H), 2.2–2.4(m, 6H), 2.4–2.6(m, 8H), 3.25(m, 2H), 3.45(m, 1H), 3.6(s, 2H), 3.95(m, 1H), 4.1(m, 2H), 6.9(d, 1H), 7.1(s, 1H), 7.25(m, 1H), 7.5(m, 2H), 7.7–7.8(m, 3H), 7.85(s, 1H), 8.05(s, 1H), 8.1(s, 1H), 8.3(d, 1H); Mass M+H 543.

EXAMPLE 11

N-{3-[3-(4-methylhomopiperazin-1-ylmethyl)benzamido]-4-methylphenyl}-2-morpholinopyridine-4-carboxamide Potassium carbonate (0.138 g) was added to a mixture of N-[3-(3-chloromethylbenzamido)-4-methylphenyl]-2-morpholinopyridine-4-carboxamide (0.232 g) and 1-methylhomopiperazine (1 ml) and the mixture was stirred and heated to 80° C. for 16 hours. The reaction mixture was allowed to cool to ambient temperature and water (25 ml) was added. The resultant solid was isolated, washed with water and dried under vacuum at 55° C. There was thus obtained the title compound (0.176 g); NMR Spectrum: (DMSOd₆) 1.72 (m, 2H), 2.21 (s, 3H), 2.24 (s, 3H), 2.6 (m, 8H), 3.53 (m, 4H), 3.67 (s, 2H), 3.74 (m, 4H), 7.1 (d, 1H), 7.23 (m, 2H), 7.51 (m, 3H), 7.8 (s, 1H), 7.84 (d, 1H), 7.9 (s, 1H), 8.25 (d, 1H), 9.86 (s, 1H), 10.28 (s, 1H): Mass Spectrum: M+H 543.

The N-[3-(3-chloromethylbenzamido)-4-methylphenyl]-2-morpholinopyridine-4-carboxamide used as a starting material was prepared as follows:

Triethylamine (31.8 ml) was added to a stirred mixture of 4-methyl-3-nitroaniline (15.8 g), 2-chloropyridine-4- carbonyl chloride (20 g) and methylene chloride (1 liter) and the resultant mixture was stirred at ambient temperature for 16 hours. The precipitate was isolated, washed with a saturated aqueous sodium bicarbonate solution and with methylene chloride and dried under vacuum at 40° C. There was thus obtained 2-chloro-N-(4-methyl-3-nitrophenyl) pyridine-4-carboxamide (10.2 g). The organic filtrate was washed with a saturated aqueous sodium bicarbonate solution, dried over magnesium sulphate and evaporated. The residue was triturated under methylene chloride and the resultant solid was isolated and dried under vacuum at 40° C. There was thus obtained a second crop (8.13 g) of 2-chloro-N-(4-methyl-3-nitrophenyl)pyridine-4-carboxamide; NMR Spectrum: (DMSOd$_6$) 2.48 (s, 3H), 7.51 (d, 1H), 7.86 (m, 1H), 7.96 (m, 2H), 8.49 (m, 1H), 8.64 (m, 1H), 10.85 (s, 1H); Mass Spectrum: M+H$^+$ 292 and 294.

A mixture of the pyridine-4-carboxamide so produced and morpholine (250 ml) was stirred and heated to 100° C. for 18 hours. The mixture was poured into water (250 ml) and stirred for 10 minutes. Methylene chloride (30 ml) was added and the resultant mixture was stirred for 30 minutes. The resultant solid was isolated, washed with methylene chloride and dried in a vacuum oven at 40° C. for 18 hours. There was thus obtained N-(4-methyl-3-nitrophenyl)-2-morpholinopyridine-4-carboxamide (17.34 g); NMR Spectrum: (DMSOd$_6$) 2.48 (s, 3H), 3.52 (m, 4H), 3.71 (m, 4H), 7.1 (d, 1H), 7.25 (s, 1H), 7.49 (d, 1H) 7.97 (m, 1H), 8.29 (m, 1H), 8.49 (m, 1H), 10.62 (s, 1H); Mass Spectrum: M+H$^+$ 343.

A mixture of a portion (8.5 g) of the material so obtained, 5% palladium-on-carbon catalyst (0.85 g) and methanol (600 ml) was stirred under an atmosphere pressure of hydrogen gas for 18 hours. Methylene chloride (400 ml) was added and the reaction mixture was filtered through diatomaceous earth. The filtrate was evaporated to give N-(3-amino-4-methylphenyl)-2-morpholinopyridine-4-carboxamide (6.41 g); NMR Spectrum: (DMSOd$_6$) 2.01 (s, 3H), 3.52 (m, 4H), 3.73 (m, 4H), 4.83 (s, 2H), 6.78 (d, 1H), 6.84 (d, 1H) 7.04–7.08 (m, 2H), 7.2 (s, 1H), 8.24 (d, 1H), 9.95 (s, 1H); Mass Spectrum M+H$^+$ 313.

3-Chloromethylbenzoyl chloride (2 g) was added to a mixture of N-(3-amino-4-methylphenyl)-2-morpholinopyridine-4-carboxamide (3.0 g), triethylamine (1.5 ml) and methylene chloride (50 ml) and the reaction mixture was stirred at ambient temperature for 3 hours. The mixture was evaporated and the residue was triturated under water. The resultant solid was isolated, washed in turn with a saturated aqueous sodium bicarbonate solution and water and dried under vacuum at 55° C. There was thus obtained the required starting material (4.6 g); NMR Spectrum: (DMSOd$_6$) 2.21 (s, 3H), 3.53 (m, 4H), 3.73 (m, 4H), 4.85 (s, 2H), 7.12 (d, 1H), 7.24 (m, 2H), 7.56 (m, 2H), 7.65 (d, 1H), 7.8 (s, 1H), 7.96 (d, 1H), 8.03 (s, 1H), 8.26 (d, 1H), 9.98 (s, 1H), 10.32 (s, 1H); Mass Spectrum M+H$^+$ 465.

EXAMPLE 12

Using an analogous procedure to that described in Example 11, the appropriate amine was reacted with the appropriate N-[3-(3- or 4-chloromethylbenzamido)-4-methylphenyl]-2-morpholinopyridine-4-carboxamide to give the compounds described in Table III.

TABLE III

| No. | R$^4$ | Q$^2$ | Note |
|---|---|---|---|
| 1 | 3-piperazin-1-ylmethyl | 2-morpholinopyrid-4-yl | a |
| 2 | 3-(3-hydroxypyrrolidin-1-ylmethyl) | 2-morpholinopyrid-4-yl | b |
| 3 | 3-[4-(2-hydroxyethyl)piperazin-1-ylmethyl] | 2-morpholinopyrid-4-yl | c |
| 4 | 3-(3-aminopyrrolidin-1-ylmethyl) | 2-morpholinopyrid-4-yl | d |
| 5 | 3-(2,6-dimethylmorpholin-4-ylmethyl) | 2-morpholinopyrid-4-yl | e |
| 6 | 3-morpholinomethyl | 2-morpholinopyrid-4-yl | f |
| 7 | 3-(4-isopropylpiperazin-1-ylmethyl) | 2-morpholinopyrid-4-yl | g |
| 8 | 4-morpholinomethyl | 2-morpholinopyrid-4-yl | h |
| 9 | 4-(4-methylpiperazin-1-ylmethyl) | 2-morpholinopyrid-4-yl | i |
| 10 | 4-(4-methylhomopiperazin-1-ylmethyl) | 2-morpholinopyrid-4-yl | j |
| 11 | 4-(3-hydroxypyrrolidin-1-ylmethyl) | 2-morpholinopyrid-4-yl | k |
| 12 | 4-[4-(2-hydroxyethyl)piperazin-1-ylmethyl] | 2-morpholinopyrid-4-yl | l |
| 13 | 4-(2,6-dimethylmorpholin-4-ylmethyl) | 2-morpholinopyrid-4-yl | m |
| 14 | 4-piperazin-1-ylmethyl | 2-morpholinopyrid-4-yl | n |
| 15 | 4-pyrrolidin-1-ylmethyl | 2-morpholinopyrid-4-yl | o |
| 16 | 4-(4-isopropylpiperazin-1-ylmethyl) | 2-morpholinopyrid-4-yl | p |
| 17 | 3-(3-pyrrolidin-1-ylpropylaminomethyl) | 2-morpholinopyrid-4-yl | q |
| 18 | 3-[2-(1-methylpyrrolidin-2-ylethyl)aminomethyl] | 2-morpholinopyrid-4-yl | r |
| 19 | 3-[3-(4-methylpiperazin-1-ylpropyl)aminomethyl] | 2-morpholinopyrid-4-yl | s |
| 20 | 3-(2-morpholinoethylaminomethyl) | 2-morpholinopyrid-4-yl | t |
| 21 | 3-(3-morpholinopropylaminomethyl) | 2-morpholinopyrid-4-yl | u |
| 22 | 3-(3-dimethylaminopropylaminomethyl) | 2-morpholinopyrid-4-yl | v |
| 23 | 3-(3-dimethylamino-2,2-dimethylpropyl-aminomethyl) | 2-morpholinopyrid-4-yl | w |
| 24 | 4-(2-morpholinoethylaminomethyl) | 2-morpholinopyrid-4-yl | x |
| 25 | 4-(3-morpholinopropylaminomethyl) | 2-morpholinopyrid-4-yl | y |
| 26 | 4-(2-piperazin-1-ylethylaminomethyl) | 2-morpholinopyrid-4-yl | z |
| 27 | 4-(3-pyrrolidin-1-ylpropylaminomethyl) | 2-morpholinopyrid-4-yl | aa |

TABLE III-continued $$R^4 \text{—} \bigcirc \text{—CONH} \quad \underset{\text{Me}}{\bigcirc} \text{—NHCO—}Q^2$$

| No. | R⁴ | Q² | Note |
|---|---|---|---|
| 28 | 4-[2-(1-methylpyrrolidin-2-ylethyl)aminomethyl] | 2-morpholinopyrid-4-yl | bb |
| 29 | 4-[3-(4-methylpiperazin-1-ylpropyl)aminomethyl] | 2-morpholinopyrid-4-yl | cc |
| 30 | 4-(3-dimethylaminopropylaminomethyl) | 2-morpholinopyrid-4-yl | dd |
| 31 | 4-(3-dimethylamino-2,2-dimethylpropyl-aminomethyl) | 2-morpholinopyrid-4-yl | ee |
| 32 | 4-diethylaminomethyl | 2-morpholinopyrid-4-yl | ff |
| 33 | 4-N-(3-dimethylaminopropyl)-N-methylaminomethyl] | 2-morpholinopyrid-4-yl | gg |

Notes a The reaction was carried out in the presence of piperazine (1.5 mmol) and acetone (5 ml) and the reaction mixture was stirred and heated to 55° C. for 16 hours. The mixture was evaporated and the residue was triturated under water. The resultant solid was isolated, washed with water and dried under vacuum at 55° C. to give the desired product; NMR(DMSOd₆)2.21(s, 3H), 2.32(m, 4H), 2.7(m, 4H), 3.52(m, 6H), 3.71(m, 4H), 7.1(d, 1H), 7.23(m, 2H), 7.46(m, 2H), 7.57(d, 1H), 7.79(s, 1H), 7.85(m, 2H), 8.24(d, 1H), 9.9(s, 1H), 10.28(s, 1H); Mass M+H 515.

b The product gave the following data: NMR(DMSOd₆)1.56(m, 1H), 1.99(m, 1H), 2.2.(s, 3H), 2.31(m, 1H), 2.42(m, 1H), 2.63(m, 2H), 3.52(m, 4H), 3.62(d, 2H), 3.71(m, 4H), 4.2(broad s, 1H), 4.64(d, 1H), 7.12(d, 1H), 7.23(m, 2H), 7.49(m, 2H), 7.58(d, 1H), 7.79 (s, 1H), 7.86(m, 2H), 8.25(d, 1H), 9.9(s, 1H), 10.28(s, 1H); Mass M+H 516.

c The product gave the following data: NMR(DMSOd₆)2.21(s, 3H), 2.4 (m, 10H), 3.5(m, 8H), 3.71(m, 4H), 4.31(t, 1H), 7.1(d, 1H), 7.24(m, 2H), 7.47(m, 2H), 7.56(d, 1H), 7.8 (s, 1H), 7.85(m, 2H), 8.25(d, 1H), 9.88(s, 1H), 10.28(s, 1H); Mass M+H 559.

d The product gave the following data: NMR(DMSOd₆)1.37(m, 1H), 2.0(m, 1H), 2.14(m, 1H), 2.2(s, 3H), 2.61(m, 4H), 3.52(m, 4H), 3.62(d, 2H), 3.71(m, 4H), 7.12(d, 1H), 7.24 (m, 2H), 7.48(m, 2H), 7.57(d, 1H), 7.8(s, 1H), 7.88(m, 2H), 8.25(d, 1H), 9.89(s, 1H), 10.29(s, 1H); Mass M+H 515.

e The product gave the following data: NMR(DMSOd₆)1.02(d, 6H), 1.69(t, 2H), 2.21(s, 3H), 2.69(d, 2H), 3.55(m, 8H), 3.71(m, 4H), 7.11(d, 1H), 7.23(m, 2H), 7.5(m, 3H), 7.8 (s, 1H), 7.87(m, 2H), 8.26(d, 1H), 9.89(s, 1H), 10.29(s, 1H); Mass M+H 544.

f The reaction was carried out in the presence of morpholine (1.5 mmol) and acetone (5 ml) and the reaction mixture was stirred and heated to 55° C. for 16 hours. The mixture was evaporated and the residue was triturated under water. The resultant solid was isolated, washed with water and dried under vacuum at 55° C. to give the desired product; NMR(DMSOd₆)2.22(s, 3H), 2.39(m, 4H), 3.54(m, 6H), 3.6(m, 4H), 3.73(m, 4H), 7.11(d, 1H), 7.28(m, 2H), 7.55(m, 3H), 7.8(s, 1H), 7.89(m, 2H), 8.3(d, 1H), 9.94(s, 1H), 10.32(s, 1H); Mass M+H 516.

g The product gave the following data: NMR(DMSOd₆) 0.95(d, 6H), 2.21(s, 3H), 2.41 (m, 8H), 2.6(m, 1H), 3.52(m, 6H), 3.74(m, 4H), 7.12(d, 1H), 7.24(m, 2H), 7.48(m, 2H), 7.57(d, 1H), 7.8(s, 1H), 7.86(m, 2H), 8.25(d, 1H), 9.88(s, 1H), 10.28(s, 1H); Mass M+H 557.

h The reaction was carried out in the presence of morpholine (1.5 mmol) and acetone (5 ml) and the reaction mixture was stirred and heated to 55° C. for 16 hours. The mixture was evaporated and the residue was triturated under water. The resultant solid was isolated, washed with water and dried under vacuum at 55° C. to give the desired product; NMR(DMSOd₆)2.2(s, 3H), 2.38(m, 4H), 3.56(m, 10H), 3.73(m, 4H), 7.1(d, 1H), 7.22(m, 2H), 7.43(d, 2H), 7.58(d, 1H), 7.8(s, 1H), 7.94(d, 2H), 8.26(d, 1H), 9.85(s, 1H), 10.28(s, 1H); Mass M+H 516.
The
N-[3-(4-chloromethylbenzamido)4-methylphenyl)-2-morpholinopyridine-4-carboxamide used as a starting material was prepared as follows:-
4-Chloromethylbenzoyl chloride (2 g) was added to a mixture of
N-(3-amino-4-methylphenyl)-2-morpholinopyridine-4-carboxamide (3.0 g), triethylamine (1.5 ml) and methylene chloride (50 ml) and the reaction mixture was stirred at ambient temperature for 3 hours. The mixture was evaporated and the residue was triturated under water. The resultant solid was isolated, washed in turn with a saturated aqueous sodium bicarbonate solution and water and dried under vacuum at 55° C. There was thus obtained the required starting material (4.3 g); NMR Spectrum: (DMSOd₆)2.21 (s, 3H), 3.54(m, 4H), 3.74(m, 4H), 4.84(s, 2H), 7.11(d, 1H), 7.24(m, 2H), 7.58(d, 3H), 7.8(s, 1H), 7.98(d, 2H), 8.25(d, 1H), 9.92(s, 1H), 10.29(s 1H); Mass Spectrum M+H⁺465.

i The product gave the following data: NMR(DMSOd₆)2.14(s, 3H), 2.2(s, 3H), 2.36(m, 8H), 3.53(m, 6H), 3.72(m, 4H), 7.12(d, 1H), 7.23(m, 2H), 7.43(d, 2H), 7.58(d, 1H), 7.8(s, 1H), 7.94(d, 2H), 8.25(d, 1H), 9.84(s, 1H), 10.28(s, 1H); Mass M+H 529.

j The product gave the following data: NMR(DMSOd₆)1.72(m, 2H), 2.2(s, 3H), 2.23(s, 3H), 2.6(m, 8H), 3.52(m, 4H), 3.65(s, 2H), 3.73(m, 4H), 7.1(d, 1H), 7.23(m, 2H), 7.44(d, 2H), 7.56(d, 1H), 7.78(s, 1H), 7.92(d, 2H), 8.24(d, 1H), 9.83(s, 1H), 10.28(s, 1H); Mass M+H 543.

TABLE III-continued

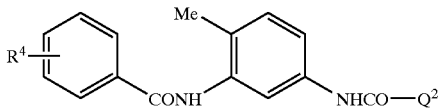

| No. | R[4] | Q[2] | Note |
|-----|------|------|------| k The product gave the following data: NMR(DMSOd₆)1.56(m, 1H), 1.99(m, 1H), 2.2(s, 3H), 2.31(m, 1H), 2.42(m, 1H), 2.58(m, 1H), 2.67(m, 1H), 3.51(m, 4H), 3.63(d, 2H), 3.72(m, 4H), 4.2(broad s, 1H), 4.65(d, 1H), 7.1(d, 1H), 7.23(m, 2H), 7.43(d, 2H), 7.57(d, 1H), 7.78(s, 1H), 7.93(d, 2H), 8.25(d, 1H), 9.83(s, 1H), 10.29(s, 1H); Mass M+H 516.

l The product gave the following data: NMR(DMSOd₆)2.21(s, 3H), 2.39(m, 10H), 3.48 (m, 8H), 3.72(m, 4H), 4.31(broads, 1H), 7.1(d, 1H), 7.23(m, 2H), 7.42(d, 2H), 7.57(d, 1H), 7.78(s, 1H), 7.94(d, 2H), 8.26(d, 1H), 9.84(s, 1H), 10.28(s, 1H); Mass M+H 559.

m The product gave the following data: NMR(DMSOd₆)1.01(d, 6H), 1.66(t, 2H), 2.2(s, 3H), 2.67(d, 2H), 3.53(m, 8H), 3.73(m, 4H), 7.11(d, 1H), 7.22(m, 2H), 7.42(d, 2H), 7.57 (d, 1H), 7.79(s, 1H), 7.93(d, 2H), 8.25(d, 1H), 9.84(s, 1H), 10.28(s, 1H); Mass M+H544.

n The reaction was carried out in the presence of piperazine (1.5 mmol) and acetone (5 ml) and the reaction mixture was stirred and heated to 55° C. for 16 hours. The mixture was evaporated and the residue was triturated under water. The resultant solid was isolated, washed with water and dried under vacuum at 55° C. to give the desired product; NMR(DMSOd₆)2.21(s, 3H), 2.3(m, 4H), 2.7(m, 4H), 3.53(m, 6H), 3.72(m, 4H), 7.1 (d, 1H), 7.22(m, 2H), 7.42(d, 2H), 7.58(d, 1H), 7.79(s, 1H), 7.93(d, 2H), 8.25(d, 1H), 9.83(s, 1H), 10.28(s, 1H); Mass M+H515.

o The reaction was carried out in the presence of pyrrolidine (1.5 mmol) and acetone (5 ml) and the reaction mixture was stirred and heated to 55° C. for 16 hours. The mixture was evaporated and the residue was triturated under water. The resultant solid was isolated, washed with water and dried under vacuum at 55° C. to give the desired product; NMR(DMSOd₆)1.71(m, 4H), 2.22(s, 3H), 2.46(m, 4H), 3.55(m, 4H), 3.67(s, 2H), 3.73(m, 4H), 7.12(d, 1H), 7.26(m, 2H), 7.46(d, 2H), 7.58(d, 1H), 7.80(s, 1H), 7.93(d, 2H), 8.3(d, 1H), 9.89(s, 1H), 10.33(s, 1H); Mass M+H500.

p The product gave the following data: NMR(DMSOd₆)0.94(d, 6H), 2.2(s, 3H), 2.42(m, 8H), 2.62(m, 1H), 3.54(m, 6H), 3.72(m, 4H), 7.1(d, 1H), 7.24(m, 2H), 7.43(d, 2H), 7.57 (d, 1H), 7.79(s, 1H), 7.93(d, 2H), 8.26(d, 1H), 9.85(s, 1H), 10.29(s, 1H); Mass M+H 557.

q The amine reactant was 1-(3-aminopropyl)pyrrolidine. The product gave the following data: NMR(DMSOd₆)1.62(m, 6H), 2.21(s, 3H), 2.39(m, 8H), 3.52(m, 4H), 3.73(m, 6H), 7.13(d, 1H), 7.23(m, 2H), 7.51(m, 3H), 7.8(m, 2H), 7.91(s, 1H), 8.25(d, 1H), 9.85(s, 1H), 10.29(s, 1H); Mass M+H557.

r The amine reactant was 2-(2-aminoethyl)-1-methylpyrrolidine. The product gave the following data: NMR (DMSOd₆)1.35(m, 2H), 1.58(m, 2H), 1.79(m, 2H), 1.98(m, 2H), 2.16(s, 3H), 2.2(s, 3H), 2.5(m, 2H), 2.9(m, 1H), 3.52(m, 4H), 3.73(m, 6H), 7.10(d, 1H), 7.22(m, 2H), 7.5(m, 3H), 7.81(m, 2H), 7.92(s, 1H), 8.24(d, 1H), 9.84(s, 1H), 10.29(s, 1H); Mass M+H557.

s The amine reactant was 1-(3-aminopropyl)4-methylpiperazine. The product gave the following data: NMR (DMSOd₆)1.58(m, 2H), 2.1(s, 3H), 2.21(s, 3H), 2.3(m, 12H), 3.53 (m, 4H), 3.72(m, 6H), 7.12(d, 1H), 7.23(m, 2H), 7.5(m, 3H), 7.81(m, 2H), 7.92(s, 1H), 8.25(d, 1H), 9.86(s, 1H), 10.31(s, 1H); Mass M+H 586.

t The amine reactant was N-(2-aminoethyl)morpholine. The product gave the following data: NMR(DMSOd₆)2.2(s, 3H), 2.25–2.65(m, 9H), 3.54(m, 8H), 3.72(m, 4H), 3.78(m, 2H), 7.11(d, 1H), 7.23(m, 2H), 7.5(m, 3H), 7.8(m, 2H), 7.91(s, 1H), 8.25(d, 1H), 9.85(s, 1H), 10.29(s, 1H); Mass M+H 559.

u The amine reactant was N-(3-aminopropyl)morpholine. The product gave the following data: NMR(DMSOd₆)1.59(m, 2H), 2.2(s, 3H), 2.3(m, 4H), 2.5(m, 4H), 3.53(m, 8H), 3.72 (m, 6H), 7.12(d, 1H), 7.24(m, 2H), 7.5(m, 3H), 7.81(m, 2H), 7.93(d, 1H), 8.24(d, 1H), 9.86(s, 1H), 10.29(s, 1H); Mass M+H 573.

v The amine reactant was 3-dimethylaminopropylamine. The product gave the following data: NMR(DMSOd6)1.57(m, 2H), 2.08(s, 6H), 2.21(m, 5H), 2.5(m, 2H), 3.52(m, 4H), 3.73(m, 6H), 7.11(d, 1H), 7.24(m, 2H), 7.43(t, 1H), 7.55(m, 2H), 7.81(m, 2H), 7.91(d, 1H), 8.25(d, 1H), 9.85(s, 1H), 10.29(s, 1H); Mass M+H 531.

w The amine reactant was 3-dimethylamino-2,2-dimethylpropylamine. The product gave the following data: NMR(DMSOd₆)0.82(s, 6H), 2.1(s, 2H), 2.18(s, 6H), 2.2(s, 3H), 2.32 (s, 2H), 3.54(m, 4H), 3.71(m, 4H), 3.77(s, 2H), 7.12(d, 1H), 7.24(m, 2H), 7.44(t, 1H), 7.55(m, 2H), 7.8(m, 2H), 7.91(d, 1H), 8.25(d, 1H), 9.84(s, 1H), 10.29(s, 1H); Mass M+H 559.

x The product gave the following data: NMR(DMSOd₆)2.2(s, 3H), 2.32(m, 4H), 2.39(m, 2H), 2.58(t, 2H), 3.54(m, 8H), 3.71(m, 4H), 3.77(s, 2H), 7.12(d, 1H), 7.23(m, 2H), 7.44 (d, 2H), 7.57(d, 1H), 7.79(s, 1H), 7.93(d, 2H), 8.25(d, 1H), 9.82(s, 1H), 10.28(s, 1H); Mass M+H 559.

y The product gave the following data: NMR(DMSOd₆)1.61(m, 2H), 2.2(s, 3H), 2.28(m, 4H), 2.5(m, 4H), 3.5(m, 8H), 3.74(m, 6H), 7.12(d, 1H), 7.22(m, 2H), 7.5(m, 3H), 7.78(s, 1H), 7.95(m, 2H), 8.25(d, 1H), 9.84(s, 1H), 10.29(s, 1H); Mass M+H573.

z The amine reactant was N-(2-aminoethyl)piperazine. The product gave the following data: NMR (DMSOd₆)2.2(s, 3H), 2.27(t, 2H), 2.39(m, 6H), 2.5(m, 2H), 2.59(t, 2H), 3.53 (m, 6H), 3.74(m, 4H), 7.12(d, 1H), 7.23(m, 2H), 7.43(d, 2H), 7.58(d, 1H), 7.8(s, 1H), 7.94(d, 2H), 8.25(d, 1H), 9.83(s, 1H), 10.28(s, 1H); Mass M+H 558.

aa The product gave the following data: NMR(DMSOd₆)1.63(m, 6H), 2.2(s, 3H), 2.38(m, 8H), 3.53(m, 4H), 3.74(m, 6H), 7.12(d, 1H), 7.23(m, 2H), 7.44(d, 2H), 7.57(d, 1H), 7.79 (s, 1H), 7.93(d, 2H), 8.24(d, 1H), 9.82(s, 1H), 10.3(s, 1H); Mass M+H 557.

TABLE III-continued

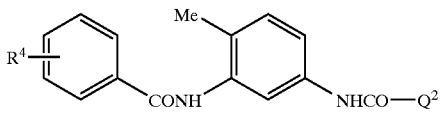

| No. | R⁴ | Q² | Note |
|-----|----|----|------| bb The product gave the following data: NMR(DMSOd₆)1.34(m, 2H), 1.58(m, 2H), 1.79 (m, 2H), 2.0(m, 2H), 2.18(s, 3H), 2.21(s, 3H), 2.5(m, 2H), 2.89(m, 1H), 3.53(m, 4H), 3.74(m, 6H), 7.12(d, 1H), 7.23(m, 2H), 7.44(d, 2H), 7.56(d, 1H), 7.79(s, 1H), 7.92(d, 2H), 8.27(d, 1H), 9.81(s, 1H), 10.30(s, 1H); Mass M+H 557.
cc The product gave the following data: NMR(DMSOd₆)1.56(m, 2H), 2.12(s, 3H), 2.21(s, 3H), 2.28(m, 12H), 3.54(m, 4H), 3.74(m, 6H), 7.13(d, 1H), 7.24(m, 2H), 7.44(d, 2H), 7.58(d, 1H), 7.81(s, 1H), 7.93(d, 2H), 8.25(d, 1H), 9.85(s, 1H); Mass M+H 586.
dd The product gave the following data: NMR(DMSOd₆)1.56(m, 2H), 2.08(s, 6H), 2.2(m, 5H), 2.5(m, 2H), 3.52(m, 4H), 3.72(m, 6H), 7.11(d, 1H), 7.23(m, 2H), 7.44(d, 2H), 7.57 (d, 1H), 7.79(s, 1H), 7.94(d, 2H), 8.25(d, 1H), 9.82(s, 1H), 10.31(s, 1H); Mass M+H 531.
ee The product gave the following data: NMR(DMSOd₆)0.83(s, 6H), 2.09(s, 2H), 2.18(s, 6H), 2.21(s, 3H), 2.28(s, 2H), 3.53(m, 4H), 3.72(m, 4H), 3.75(s, 2H), 7.1(d, 1H), 7.22(m, 2H), 7.45(d, 2H), 7.57(d, 1H), 7.8(s, 1H), 7.93(d, 2H), 8.25(d, 1H), 9.8(s, 1H), 10.28(s, 1H); Mass M+H 559.
ff The reaction was carried out in the presence of diethylammonium chloride (2.5 mmol), potassium carbonate (3 mmol) and acetone (5 ml) and the reaction mixture was stirred and heated to 55° C. for 18 hours. The mixture was evaporated and the residue was triturated under water. The resultant solid was isolated, washed with water and dried under vacuum at 88° C. to give the desired product; NMR(DMSOd₆)0.99(t, 6H), 2.21(s, 3H), 2.45(m, 4H), 3.52(m, 4H), 3.6(s, 2H), 3.72(m. 4H), 7.11(d, 1H), 7.25(m, 2H), 7.52(m, 3H), 7.85(m, 3H), 8.28(d, 1H), 9.92(s, 1H), 10.33(s, 1H); Mass M+H 502.
gg The product gave the following data: NMR(DMSOd₆)1.57(m, 2H), 2.08(s, 6H), 2.12 (s, 3H), 2.2(s, 5H), 2.34(t, 2H), 3.51(m, 6H), 3.7(m, 4H), 7.1(d, 1H), 7.23(m, 2H), 7.42 (d, 2H), 7.55(d, 1H), 7.79(s, 1H), 7.92(d, 2H), 8.25(d, 1H), 9.83(s, 1H), 10.28(s, 1H); Mass M+H 543.

EXAMPLE 13

N-{3-[3-(2-morpholinoethoxy)benzamido]-4-methylphenyl}quinoline-6-carboxamide

Using an analogous procedure to that described in Example 7 except that the reaction mixture was heated to 70° C. rather than 40° C., N-[3-(3-hydroxybenzamido)-4-methylphenyl]quinoline-6-carboxamide was reacted with 2-morpholinoethyl chloride to give the title compound in 41% yield, m.p. 216–217° C.; NMR Spectrum: (DMSOd₆) 2.21 (s, 3H), 2.47 (m, 4H), 2.73 (t, 2H), 3.59 (t, 4H), 4.18 (t, 4H), 7.17 (m, 1H), 7.24 (d, 1H), 7.42 (t, 1H), 7.54 (s, 2H), 7,61 (m, 2H), 7.87 (s, 1H), 8.15 (d, 1H), 8.23 (m, 1H), 8.52 (m, 1H), 8.61 (s, 1H), 9.0 (d, 1H), 9.9 (s, 1H), 10.49 (s, 1H); Mass Spectrum: M+H⁺ 511.

EXAMPLE 14

N-{3-[4-(2-pyridylmethoxy)benzamido]-4-methylphenyl}quinoline-6-carboxamide

Using an analogous procedure to that described in Example 7 except that the reaction mixture was heated to 70° C. for 48 hours rather than to 40° C. for 18 hours, N-[3-(4-hydroxybenzamido)-4-methylphenyl]quinoline-6-carboxamide was reacted with 2-chloromethylpyridine to give the title compound in 72% yield; NMR Spectrum: (DMSOd₆) 2.22 (s, 3H), 5.28 (s, 2H), 7.16 (d, 2H), 7.22 (d, 1H), 7.34 (m, 1H), 7.53 (m, 1H), 7.62 (m, 2H), 7.85 (m, 2H), 7.95 (m, 1H), 8.12 (d, 1H), 8.23 (m, 1H), 8.52 (m, 1H), 8.59 (m, 2H), 9.0 (d, 1H), 10.48 (s, 1H); Mass Spectrum: M+H⁺ 489.

The N-[3-(4-hydroxybenzamido)-4-methylphenyl]quinoline-6-carboxamide used as a starting material was prepared as follows:

Using analogous procedures to those described in the last two paragraphs of the portion of Example 7 which is concerned with the preparation of starting materials, 4-benzyloxybenzoic acid was reacted with N-(3-amino-4-methylphenyl)quinoline-6-carboxamide to give N-[3-(4-benzyloxybenzamido)-4-methylphenyl]quinoline-6-carboxamide in 50% yield, m.p. 227–228° C.; NMR Spectrum: (DMSOd₆) 2.21 (s, 3H), 5.2 (s, 2H), 7.12 (d, 2H), 7.25 (d, 1H), 7.39 (m, 5H), 7.61 (m, 2H), 7.86 (d, 1H), 8.52 (d, 1H), 8.62 (d, 1H), 8.99 (m, 1H), 9.76 (s, 1H), 10.47 (s, 1H); and that compound was hydrogenolysed to give the required starting material in 93% yield; NMR Spectrum: (DMSOd₆) 2.2 (s, 3H), 6.83 (d, 2H), 7.23 (d, 1H), 7.61 (m, 2H), 7.85 (m, 3H), 8.12 (d, 1H), 8.25 (d, 1H), 8.52 (d, 1H), 8.62 (s, 1H), 8.99 (d, 1H), 9.61 (s, 1H), 10.46 (s, 1H); Mass Spectrum: M–H⁻ 396.

EXAMPLE 15

N-[2-methyl-5-(2-morpholinopyrid-4-ylcarbonylamino)phenyl]-5-[N-(3-dimethylaminopropyl)-N-methylamino]-2-nitrobenzamide A mixture of N-[2-methyl-5-(2-morpholinopyrid-4-ylcarbonylamino)phenyl]-5-chloro-2-nitrobenzamide (0.2 g) and N-(3-dimethylaminopropyl)-N-methylamine (1.5 ml) was stirred and heated to 100° C. for 16 hours. The mixture was cooled and poured into water. The resultant precipitate was isolated, washed in turn with water and diethyl ether and dried under vacuum at 40° C. There was thus obtained the title compound (0.223 g); NMR Spectrum: (DMSOd₆) 1.62–1.74 (m, 2H), 2.12 (s, 6H), 2.18–2.26 (m, 5H), 3.08 (s, 3H), 3.50–3.54 (m, 6H), 3.69–3.71 (m, 4H), 6.75 (s, 1H), 6.84 (s, 1H), 7.12 (d, 1H), 7.26 (s, 1H), 7.68 (d, 1H), 7.9 (s, 1H), 8.04 (d, 1H), 8.26 (d, 1H), 9.82 (s, 1H), 10.04 (s, 1H); Mass Spectrum M+H⁺ 576.

The N-[2-methyl-5-(2-morpholinopyrid-4-ylcarbonylamino)phenyl]-5-chloro-2-nitrobenzamide used as a starting material was prepared as follows:

Triethylamine (31.8 ml) was added to a stirred mixture of 4-methyl-3-nitroaniline (15.8 g), 2-chloropyridine-4-carbonyl chloride (20 g) and methylene chloride (1 liter) and the resultant mixture was stirred at ambient temperature for 16 hours. The precipitate was isolated, washed with a saturated aqueous sodium bicarbonate solution and with methylene chloride and dried under vacuum at 40° C. There was thus obtained 2-chloro-N-(4-methyl-3-nitrophenyl)pyridine-4-carboxamide (10.2 g). The organic filtrate was washed with a saturated aqueous sodium bicarbonate solution, dried over magnesium sulphate and evaporated. The residue was triturated under methylene chloride and the resultant solid was isolated and dried under vacuum at 40° C. There was thus obtained a second crop (8.13 g) of 2-chloro-N-(4-methyl-3-nitrophenyl)pyridine-4-carboxamide; NMR Spectrum: (DMSOd$_6$) 2.48 (s, 3H), 7.51 (d, 1H), 7.86 (m, 1H), 7.96 (m, 2H), 8.49 (m, 1H), 8.64 (m, 1H), 10.85 (s, 1H); Mass Spectrum: M+H$^+$ 292 and 294.

A mixture of the pyridine-4-carboxamide so produced and morpholine (250 ml) was stirred and heated to 100° C. for 18 hours. The mixture was poured into water (250 ml) and stirred for 10 minutes. Methylene chloride (30 ml) was added and the resultant mixture was stirred for 30 minutes. The resultant solid was isolated, washed with methylene chloride and dried in a vacuum oven at 40° C. for 18 hours. There was thus obtained N-(4-methyl-3-nitrophenyl)-2-morpholinopyridine-4-carboxamide (17.34 g); NMR Spectrum: (DMSOd$_6$) 2.48 (s, 3H), 3.52 (m, 4H), 3.71 (m, 4H), 7.1 (d, 1H), 7.25 (s, 1H), 7.49 (d, 1H) 7.97 (m, 1H), 8.29 (m, 1H), 8.49 (m, 1H), 10.62 (s, 1H); Mass Spectrum: M+H$^+$ 343.

A mixture of a portion (8.5 g) of the material so obtained, 5% palladium-on-carbon catalyst (0.85 g) and methanol (600 ml) was stirred under an atmosphere pressure of hydrogen gas for 18 hours. Methylene chloride (400 ml) was added and the reaction mixture was filtered through diatomaceous earth. The filtrate was evaporated to give N-(3-amino-4-methylphenyl)-2-morpholinopyridine-4-carboxamide (6.41 g); NMR Spectrum: (DMSOd$_6$) 2.01 (s, 3H), 3.52 (m, 4H), 3.73 (m, 4H), 4.83 (s, 2H), 6.78 (d, 1H), 6.84 (d, 1H) 7.04–7.08 (m, 2H), 7.2 (s, 1H), 8.24 (d, 1H), 9.95 (s, 1H); Mass Spectrum M+H$^+$ 313.

Oxalyl chloride (0.55 g) was added dropwise to a stirred mixture of 5-chloro-2-nitrobenzoic acid (0.726 g), DMF (a few drops) and methylene chloride (25 ml) which had been cooled to 0° C. The mixture was allowed to warm to ambient temperature and was stirred for 5 hours. The mixture was evaporated. The residue was dissolved in methylene chloride (10 ml) and was added dropwise to a stirred mixture of N-(3-amino-4-methylphenyl)-2-morpholinopyridine-4-carboxamide (0.933 g), triethylamine (1.12 ml) and methylene chloride (25 ml). The mixture was stirred at ambient temperature for 16 hours. The resultant precipitate was isolated, washed in turn with water methylene chloride and diethyl ether and dried under vacuum at 40° C. There was thus obtained N-[2-methyl-5-(2-morpholinopyrid-4-ylcarbonylamino)phenyl]-5-chloro-2-nitrobenzamide (1.12 g); NMR Spectrum: (DMSOd$_6$) 2.23 (s, 3H), 3.5–3.54 ( m, 4H), 3.69–3.73 (m, 4H), 7.12 (d, 1H), 7.2–7.25 (m, 2H), 7.58 (d, 1H), 7.81 (d, 1H), 7.87–7.9 (m, 2H), 8.15 (d, 1H), 8.26 (d, 1H); Mass Spectrum M+H$^+$ 496 and 498.

EXAMPLE 16

N-[2-methyl-5-(2-morpholinopyrid-4-ylcarbonylamino)phenyl]-2-amino-5-[N-(3-dimethylaminopropyl)-N-methylamino]benzamide A mixture of N-[2-methyl-5-(2-morpholinopyrid-4-ylcarbonylamino)phenyl]-5-[N-(3-dimethylaminopropyl)-N-methylamino]-2-nitrobenzamide (0.22 g), 10% palladium-on-carbon (0.02 g) and methanol (15 ml) was stirred under an atmosphere of hydrogen gas. After cessation of hydrogen uptake, the catalyst was removed by filtration through diatomaceous earth and the filtrate was evaporated. There was thus obtained the title compound (0.15 g); Mass Spectrum M+H$^+$ 546.

EXAMPLE 17

N-[2-methyl-5-(2-morpholinopyrid-4-ylcarbonylamino)phenyl]-5-(4-methylpiperazin-1-yl)-2-nitrobenzamide In an analogous procedure to that described in Example 15, N-[2-methyl-5-(2-morpholinopyrid-4-ylcarbonylamino)phenyl]-5chloro-2-nitrobenzamide was reacted with 1-methylpiperazine to give the title compound; NMR Spectrum: (DMSOd$_6$) 2.21 (s, 3H), 2.24 (s, 3H), 2.41–2.47 (m, 4H), 2.63–2.69 (m, 2H), 3.46–3.53 (m, 8H), 3.69–3.72 (m, 4H), 7.0 (s, 1H) 7.04–7.12 (m, 2H), 7.19 (d, 1H), 7.25 (s, 1H), 7.57 (d, 1H), 7.88 (s, 1H), 8.04 (d, 1H), 8.26 (d, 1H), 9.83 (s, 1H), 10.33 (s, 1H); Mass Spectrum: M+H$^+$ 560.

EXAMPLE 18

N-[2-methyl-5-(2-morpholinopyrid-4-ylcarbonylamino)phenyl]-2-amino-5-(4-methylpiperazin-1-yl)benzamide In an analogous procedure to that described in Example 16, N-[2-methyl-5-(2-morpholinopyrid-4-ylcarbonylamino)phenyl]-5-(4-methylpiperazin-1-yl)-2-nitrobenzamide was reduced catalytically to give the title compound: Mass Spectrum: M+H$^+$ 530.

EXAMPLE 19

N-[2-methyl-5-(2-morpholinopyrid-4-ylcarbonylamino)phenyl]-3-[N-(3-dimethylaminopropyl)-N-methylamino]-2-nitrobenzamide In an analogous procedure to that described in Example 15, N-[2-methyl-5-(2-morpholinopyrid-4-ylcarbonylamino)phenyl]-3-chloro-2-nitrobenzamide was reacted with N-(3dimethylaminopropyl)-N-methylamine to give the title compound; NMR Spectrum: (DMSOd$_6$) 1.44–1.58 (m, 2H), 2.06 (s, 6H), 2.15 (t, 2H), 2.21 (s, 3H), 2.69 (s, 3H), 3.02 (t, 2H), 3.48–3.53 (m, 4H) 3.69–3.73 (m, 4H), 7.1 (d, 1H), 7.19–7.25 (m, 2H), 7.44–7.62 (m, 3H), 7.74–7.64 (m, 1H), 7.94 (d, 1H), 8.26 (d, 1H), 10.13 (s, 1H), 10.32 (s, 1H); mass spectrum: M+H$^+$ 576.

The N-[2-methyl-5-(2-morpholinopyrid-4-ylcarbonylamino)phenyl]-3-chloro-2-nitrobenzamide used as a starting material was prepared as follows:

In an analogous procedure to that described in the last paragraph of the portion of Example 15 which is concerned with the preparation of starting materials, 3-chloro-2-nitrobenzoyl chloride (obtained by the reaction of 3-chloro-2-nitrobenzoic acid and oxalyl chloride) was reacted with N-(3-amino-4-methylphenyl)-2-morpholinopyridine-4-carboxamide to give the required starting material; NMR Spectrum: (DMSOd$_6$) 2.2 (s, 3H), 3.49–3.53 (m, 4H) 3.69–3.73 (m, 4H), 7.1 (d, 1H), 7.18–7.24 (m, 2H), 7.58 (d, 1H), 7.68–7.78 (m, 2H), 7.58 (d, 1H), 7.68–7.78 (m, 2H), 7.84–8.0 (m, 2H), 8.25 (d, 1H); Mass Spectrum: M+H$^+$ 496 and 498.

EXAMPLE 20

N-[2-methyl-5-(2-morpholinopyrid-4-ylcarbonylamino)phenyl]-2-amino-3-[N-(3-dimethylaminopropyl)-N-methylamino]benzamide In an analogous procedure to that described in Example 16, N-[2-methyl-5-(2-morpholinopyrid-4-ylcarbonylamino)

phenyl]-3-[N3-dimethylaminopropyl)-N-methylamino]-2-nitrobenzamide was reduced catalytically to give the title compound: Mass Spectrum: M+H$^+$ 546.

EXAMPLE 21

N-{3-[3-(4-methylpiperazin-1-ylmethyl)benzamido]-4-methylphenyl}-2,3-dihydrobenzofuran-5-carboxamide 2,3-Dihydrobenzofuran-2-carboxylic acid (0.109 g) was added to a stirred mixture of N-(5-amino-2-methylphenyl)-3-(4-methylpiperazin-1-ylmethyl)benzamide (0.15 g), diisopropyethyllamine (0.232 ml), 2-(7-azabenzotriazol-1-yl)-1,1,3,3-tetramethyluronium hexafluorophosphate(V) (0.253 g) and DMF (10 ml) and the mixture was stirred at ambient temperature for 66 hours. The mixture was partitioned between methylene chloride and water. The organic phase was washed with a saturated aqueous solution of sodium bicarbonate and evaporated. The residue was purified by column chromatography on an ion exchange column (isolute SCX column from International Sorbent Technology Limited, Hengoed, Mid-Glamorgan, UK) using a 99:1 mixture of methanol and a saturated aqueous ammonium hydroxide solution as eluent. The product so obtained was dissolved in acetone and precipitated by the addition of isohexane. There was thus obtained the title compound (0.089 g); NMR Spectrum: (DMSOd$_6$) 2.15 (s, 3H), 2.2 (s, 3H), 2.30–2.45 (m, 8H), 3.25 (t, 2H), 3.55 (s, 2H), 4.6 (t, 2H), 6.85–6.9 (m, 1H), 7.18–7.22 (m, 1H), 7.4–7.66 (m, 3H), 7.75–7.9 (m, 5H), 9.85 (s, 1H), 10.0 (s, 1H); Mass Spectrum: M+H$^+$ 485.

EXAMPLE 22

Using an analogous procedure to that described in Example 21. the appropriate heteroarylcarboxylic acid was reacted with the appropriate aniline to give the compounds described in Table IV.

TABLE IV

| No. | R$^4$ | Q$^2$ | Note |
|---|---|---|---|
| 1 | 3-(4-methylpiperazin-1-ylmethyl) | 2-methyl-2-3-dihydrobenzofuran-7-yl | a |
| 2 | 3-(4-methylpiperazin-1-ylmethyl) | 2,2-dimethylchroman-6-yl | b |
| 3 | 3-(4-methylpiperazin-1-ylmethyl) | 5-phenylpyrid-3-yl | c |
| 4 | 3-(4-methylpiperazin-1-ylmethyl) | 5-benzyloxypyrid-3-yl | d |
| 5 | 3-(4-methylpiperazin-1-ylmethyl) | 2-chloro-6-phenylpyrid-4-yl | e |
| 6 | 3-(4-methylpiperazin-1-ylmethyl) | 2-(1,2,4-triazol-1-yl)pyrid-4-yl | f |
| 7 | 3-(4-methylpiperazin-1-ylmethyl) | 2-chloro-6-morpholinopyrimidin-4-yl | g |
| 8 | 4-diethylaminomethyl | 2-chloro-6-morpholinopyrimidin-4-yl | h |

Notes a The starting material was 2-methyl-2-3-dihydrobenzofuran-7-carboxylic acid which is described in J. Med. Chem., 1992 35 310–319. The product gave the following data: NMR(DMSOd$_6$)1.5(d, 3H), 2.15(s, 3H), 2.2(s, 3H), 2.3–2.45(m, 8H), 2.8–2.95(m, 1H), 3.35–3.5(m, 1H), 3.55(s, 2H), 4.1–4.2(m, 1H), 6.95–7.0(m, 1H), 7.2–7.25(m, 1H), 7.38–7.55(m, 4H), 7.6–7.65(m, 1H), 7.75–7.8(m, 1H), 7.85–7.9(m, 2H), 9.7(s, 1H), 9.9(s, 1H); Mass M+H499.
b The starting material was 2,2-dimethylchroman-6-carboxylic acid which is described in J. Med. Chem., 1997 40, 2445–2451. The product gave the following data: NMR (DMSOd$_6$)1.3(s, 6H), 1.8(t, 2H), 2.2(s, 3H), 2.3(s, 3H), 2.4–2.6(m, 8H), 2.8(t, 2H), 3.55 (s, 2H), 6.75–6.8(m, 1H), 7.15–7.25(m, 1H), 7.4–7.6(m. 3H), 7.65–7.75(m, 1H), 7.75–7.8 (m, 1H), 7.8–7.85(m, 1H), 7.85–7.9(m, 2H), 9.9(s, 1H), 10.0(s, 1H); Mass M+H527.
c The starting material was 5-phenylpyridine-3-carboxylic acid which is described in Tetrahedron Letters, 1998, 39, 4175–4178. The product gave the following data: NMR (DMSOd$_6$)2.15(s, 3H), 2.2(s, 3H), 2.25–2.45(m, 8H), 3.5(s, 2H), 7.25–7.3(m, 1H), 7.4–7.65(m, 6H), 7.8–7.9(m, 5H), 8.55(s, 1H), 9.05(s, 2H), 9.95(s, 1H), 10.5(s, 1H); Mass M+H520.
d The product gave the following data: NMR(DMSOd$_6$)2.2(s, 3H), 2.3(s, 3H), 2.4–2.6(m, 8H), 3.55(s, 2H), 5.2–5.3(m, 2H), 7.2–7.3(m, 1H), 7.3–7.6(m, 8H), 7.8–7.85 (m, 1H), 7.85–7.9(m, 2H), 7.9–7.95(m, 1H), 8.5–8.55(m, 1H), 8.7–8.75(m, 1H), 9.9(s, 1H), 10.37 (s, 1H); Mass M+H550.
The 5-benzyloxypyridine-3-carboxylic acid used as a starting material was obtained as follows:-
Benzyl alcohol (18.4 g) was added over 20 minutes to a stirred mixture of sodium hydride (60% dispersion in mineral oil, 6.8 g) and DMF (200 ml). The resultant mixture was warmed to 60° C. for 1 hour. A solution of 3,5-dibromopyridine (40 g) in DMF (50 ml) was added and the mixture was heated to 80° C. for 2 hours. The mixture was cooled to ambient temperature and evaporated. The residual oil was partitioned between ethyl acetate and water. The organic phase was washed with a saturated aqueous sodium chloride solution, dried over sodium sulphate and evaporated. The material so obtained was triturated under hexane. The solid so obtained was washed with diethyl ether giving 5-benzyloxy-3-bromopyridine (18 g); NMR(CDCl$_3$)5.1(s, 2H), 7.3–7.5(m, 6H), 8.3–8.4 (m, 2H).

TABLE IV-continued

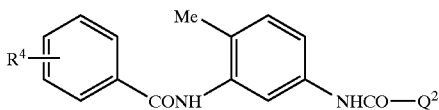

| No. | R⁴ | Q² | Note |
|---|---|---|---|

A solution of a portion (0.95 g) of the material so obtained in diethyl ether (10 ml) was added slowly to a mixture of tert-butyl lithium and diethyl ether (30 ml) which had been cooled to −95° C. An excess of DMF was added and the mixture was stirred and allowed to warm to ambient temperature. The reaction mixture was partitioned between ethyl acetate and water. The organic phase was washed with brine, dried over sodium sulphate and evaporated. The residue was purified by column chromatography on silica using a 4:1 mixture of hexane and ethyl acetate as eluent. There was thus obtained to give 5-benzyloxy-3-formylpyridine (0.5 g); NMR(DMSOd₆)5.3(s, 2H), 7.3–7.55(m, 5H), 7.8–7.85(m, 1H), 8.6–8.65(m, 1H), 8.7(d, 1H), 10.1(s, 1H).
A mixture of a portion (0.43 g) of the material so obtained, 3-chloroperbenzoic acid (0.7 g) and methylene chloride (15 ml) was stirred at ambient temperature for 1 hour. The precipitate was isolated and washed with methylene chloride. There was thus obtained 5-benzyloxypyridine-3-carboxylic acid (0.23 g); NMR(DMSOd₆)5.25(s, 2H), 7.35–7.5(m, 5H), 7.8–7.85(m, 1H), 8.57(d, 1H), 8.67(d, 1H).
e The product gave the following data: NMR(DMSOd₆)2.2–2.3(m, 6H), 3.1–3.5(m, 8H), 3.55(s, 2H), 7.25–7.3(m, 1H), 7.4–7.65(m, 6H), 7.8–7.95(m, 4H), 8.1–8.2(m, 2H), 8.4(s, 1H), 9.95(s, 1H), 10.6(s, 1H); Mass M+H554.
The 2-chloro-6-phenylpyridine-4-carboxylic acid used as a starting material was obtained as follows:-
Phosphorus oxychloride (28 ml) was added carefully to a stirred sample of 2-hydroxy-6-phenylpyridine-4-carboxylic acid (26 g) and the mixture was heated to 110° C. Phosphorus pentachloride (63 g) was added to the hot mixture and the resultant mixture was heated to 140° C. for 1 hour. The excess of phosphorus oxychloride was evaporated under reduced pressure and water was added to the residue which was cooled in an ice-bath. The resultant solid was triturated under industrial methylated spirits. The filtrate was evaporated and the resultant residue was triturated under ethyl acetate. The filtrate so obtained was evaporated and the residual solid was washed with carbon tetrachloride and dried to give 2-chloro-6-phenylpyridine-4-carboxylic acid (11 g), m.p. 188° C.; NMR (DMSOd₆)7.4–7.6(m, 3H), 7.8(s, 1H), 8.0–8.15(m, 2H), 8.25(s, 1H).
f The product gave the following data: NMR(DMSOd₆) 2.2–2.25(m, 6H), 2.35–2.5(m, 8H), 3.55(s, 2H), 7.25–7.3(m, 1H), 7.4–7.55(m, 2H), 7.55–7.6(m, 1H), 7.8–7.9(m, 3H), 7.9–8.0(m, 1H), 8.3–8.4(m, 2H), 8.7–8.75(m, 1H), 9.54(s, 1H), 9.9(s, 1H), 10.71(s, 1H); Mass M+H511.
The 2-(1,2,4-triazol-1-yl)pyridine-4-carboxylic acid used as a starting material was obtained as follows:-
Phosphorus oxychloride (73 ml) was added carefully to a stirred sample of 4-carboxypyridine-N-oxide (21 g) which had been cooled to ° C.; Phosphorus pentachloride (62 g) was added and the resultant mixture was stirred and heated to reflux for 4 hours. The mixture was cooled to ambient temperature and poured onto ice. The resultant precipitate was isolated and dissolved in 2N aqueous sodium hydroxide solution. The solution was filtered and the filtrate was acidified by the addition of 2N aqueous hydrochloric acid. The precipitate was isolated, washed with water and dried to give 2-chloropyridine-4-carboxylic acid (19.7 g), m.p. 236–2380° C.
A mixture of a portion (5 g) of the material so obtained and 1,2,4-triazole (4.38 g) was sealed in a glass Carius tube and heated to 190° C. for 24 hours. The resultant material was triturated under methanol to give a solid which was isolated. There was thus obtained 2-(1,2,4-triazol-1-yl)pyridine-4-carboxylic acid (4.2 g); NMR(DMSOd₆)7.85(m, 1H), 8.2(s, 1H), 8.35(s, 1H), 8.7(d, 1H), 9.4(s, 1H).
g The product gave the following data: NMR(DMSOd₆)2.15(s, 3H), 2.21(s, 3H), 2.33–2.39(m, 8H), 3.53(s, 2H), 3.69(br s, 8H), 7.25(d, 1H), 7.35(s, 1H), 7.43–7.52(m, 2H), 7.63(d, 1H), 7.86–7.92(m, 3H), 9.89(s, 1H), 10.30(s, 1H); Mass M+H564and566.
The 2-chloro-6-morpholinopyrimidine-4-carboxylic acid used as a starting material was obtained as follows:-
A mixture of methyl 2-chloro-morpholinopyrimidine-4-carboxylate(Chemical Abstracts, volume 106, abstract 176313, 0.21 g), lithium hydroxide (1M, 1.01 ml), methanol (10 ml) and water (2 ml) was stirred at ambient temperature for 16 hours. The mixture was evaporated and the residue was dissolved in water (2.0 ml). A hydrogen chloride solution (1M in diethyl ether) was added and the resultant solid was isolated. There was thus obtained 2-chloro 6-morpholinopyrimidine-4-carboxylic acid (0.132 g); NMR(DMSOd₆) 3.66(br s, 8H), 7.28(s, 1H); Mass M+H⁺244 and 246.
h The product gave the following data: NMR(DMSOd₆)0.98(t, 6H), 2.2(s, 3H), 2.43–2.49 (m, 4H), 3.59(s, 2H), 3.68(br s, 8H), 7.23(d, 1H), 7.44(d, 2H), 7.63(d, 1H), 7.75–7.78(m, 1H), 7.92(d, 3H), 8.08(d, 2H), 9.82(s, 1H), 10.39(s, 1H); Mass M+H451and453.

EXAMPLE 23

N-{3-[3-(4-methylpiperazin-1-ylmethyl)benzamido]-4-methylphenyl}-6-morpholinopyridine-2-carboxamide A mixture of N-{3-[3-(4-methylpiperazin-1-ylmethyl) benzamido]-4-methylphenyl}-6-chloropyridine-2-carboxamide (0.2 g) and morpholine (3 ml) was stirred and heated to 110° C. for 16 hours. The resultant solution was cooled to ambient temperature and poured into water and extracted with methylene chloride. The organic phase was evaporated and the residue was purified by reversed-phase column chromatography on a C18 isolute column eluting initially with water and then with a 5:1 mixture of water and methanol. There was thus obtained the title compound (0.169 g); NMR Spectrum: (DMSOd$_6$) 2.15 (s, 3H), 2.19 (s, 3H), 2.25–2.39 (m, 8H), 3.52 (s, 2H), 3.57–3.6 (m, 4H), 3.71–3.75 (m, 4H), 7.05 (d, 1H), 7.22 (d, 1H), 7.4–7.49 (m, 3H), 7.64 (d, 1H), 7.76 (t, 1H), 7.82–7.88 (m, 3H), 9.92 (s, 1H), 10.08 (s, 1H); Mass Spectrum: M+H$^+$ 529.

The N-{3-[3-(4-methylpiperazin-1-ylmethyl) benzamido]-4-methylphenyl}-6-chloropyridine-2-carboxamide used as a starting material was prepared as follows:

A mixture of 6-chloropyridine-2-carbonyl chloride [obtained by the reaction in methylene chloride of 6-chloropyridine-2-carboxylic acid (0.5 g) and oxalyl chloride], N-(5-amino-2-methylphenyl)-3-(4-methylpiperazin-1-ylmethyl)benzamide (0.85 g), triethylamine (0.97 ml) and methylene chloride (20 ml) was stirred at ambient temperature for 16 hours. The mixture was washed with a saturated aqueous solution of sodium bicarbonate. The organic phase was evaporated and the residue was triturated under a mixture of ethyl acetate and isohexane. The resultant solid was isolated and dried under vacuum at 40° C. There was thus obtained the required starting material (0.508 g); NMR Spectrum: (DMSOd$_6$) 2.15 (s, 3H), 2.2 (s, 3H), 2.24–2.42 (m, 8H), 3.52 (s, 2H), 7.24 (d, 1H), 7.42–7.52 (m, 2H), 7.62 (m, 1H), 7.76–7.8 (m, 1H), 7.82–7.88 (m, 2H), 7.93 (s, 1H), 8.07–8.1 (m, 2H), 9.9 (s, 1H), 10.34 (s, 1H); Mass Spectrum: M+H$^+$ 478 and 480.

EXAMPLE 24

Using an analogous procedure to that described in Example 23, the appropriate chloroheteroaryl compound was reacted with the appropriate amine to give the compounds described in Table V.

TABLE V $$R^4 \text{—} \bigotimes \text{—CONH—} \bigotimes^{Me} \text{—NHCO—} Q^2$$

| No. | R$^4$ | Q$^2$ | Note |
|---|---|---|---|
| 1 | 4-diethylaminomethyl | 6-morpholinopyrid-2-yl | a |
| 2 | 4-diethylaminomethyl | 2-piperidinopyrid-4-yl | b |
| 3 | 4-diethylaminomethyl | 2-(3-hydroxypyrrolidin-1-yl)pyrid-4-yl | c |
| 4 | 4-diethylaminomethyl | 2-(3-hydroxymethylpiperidin-1-yl)pyrid-4-yl | d |
| 5 | 4-diethylaminomethyl | 2-(4-hydroxymethylpiperidin-1-yl)pyrid-4-yl | e |
| 6 | 4-diethylaminomethyl | 2-(3-methylpiperidin-1-yl)pyrid-4-yl | f |
| 7 | 4-diethylaminomethyl | 2-(2,6-dimethylpiperidin-1-yl)pyrid-4-yl | g |
| 8 | 4-diethylaminomethyl | 2-chloro-6-morpholinopyrid-4-yl | h |
| 9 | 4-diethylaminomethyl | 2-chloro-6-pyrrolidin-1-ylpyrid-4-yl | i |
| 10 | 4-diethylaminomethyl | 2-chloro-6-piperidinopyrid-4-yl | j |
| 11 | 3-(4-methylpiperazin-1-ylmethyl) | 2-chloro-6-morpholinopyrid-4-yl | k |
| 12 | 3-(4-methylpiperazin-1-ylmethyl) | 2-chloro-6-pyrrolidin-1-ylpyrid-4-yl | l |
| 13 | 3-(4-methylpiperazin-1-ylmethyl) | 2-(3-hydroxymethylpiperidin-1-yl)pyrid-4-yl | m |
| 14 | 3-(4-methylpiperazin-1-ylmethyl) | 2-(4-hydroxymethylpiperidin-1-yl)pyrid-4-yl | n |
| 15 | 3-(4-methylpiperazin-1-ylmethyl) | 2-(3-methylpiperidin-1-yl)pyrid-4-yl | o |
| 16 | 3-(4-methylpiperazin-1-ylmethyl) | 2-(3-pyrrolin-1-yl)pyrid-4-yl | p |
| 17 | 3-(4-methylpiperazin-1-ylmethyl) | 2-cyclobutylaminopyrid-4-yl | q |
| 18 | 3-(4-methylpiperazin-1-ylmethyl) | 2-homopiperidin-1-ylpyrid-4-yl | r |
| 19 | 4-diethylaminomethyl | 6-morpholinopyriinidin-4-yl | s |

Notes a) The product gave the following data: NMR(DMSOd$_6$) 0.98(t, 6H), 2.19(s, 3H), 2.42–2.49 (m, 4H), 3.28(s, 2H), 3.57–3.6(m, 4H), 3.71–3.75(m, 4H), 7.05(d, 1H), 7.14(d, 1H), 7.4–7.46 (m, 3H), 7.64(d, 1H), 7.77(t, 1H), 7.83(s, 1H), 7.92(d, 2H), 9.86(s, 1H), 10.03(s, 1H); Mass M + H 502.
The N-[3-(4-diethylaminomethylbenzamido)-4-methylphenyl]-6-chloropyridine-2-carboxamide used as a starting material was prepared by the reaction of N-(5-amino-2-methylphenyl)4-diethylaminomethylbenzamide and 6-chloropyridine-2-carbonyl chloride using an analogous procedure to that described in the portion of Example 23 which is concerned with the preparation of starting materials. The required starting material gave the following data: NMR (DMSOd$_6$)0.98(t, 6H), 2.2(s, 3H), 2.42–2.49(m, 4H), 3.59(s, 2H), 7.23(d, 1H), 7.44(d, 2H), 7.63(d, 1H), 7.75–7.78(m, 1H), 7.92(d, 3H), 8.08(d, 2H), 9.82(s, 1H), 10.39(s, 1H); Mass M + H 451 and 453.
b) The product gave the following data: NMR(DMSOd$_6$) 1.05(t, 6H), 1.6–1.7(m, 6H), 2.3(s, 3H), 2.5–2.6(m, 4H), 3.55–3.65(m 6H), 6.8–6.85(m, 1H), 7.1(s, 1H), 7.18–7.22(m, 1H), 7.42–7.5(m, 2H), 7.7–7.78(m, 2H), 7.78–7.85(m, 2H), 8.0–8.05(m, 1H), 8.1–8.15(m, 1H), 8.2–8.25(m, 1H); Mass M + H 500.
c) The product gave the following data: Mass M + H 502.
d) DMF(1 ml) was added as a solvent and a large excess of the amine was used. The product gave the following data: Mass M + H 530.
e) DMF(1 ml) was added as a solvent and a large excess of the amine was used. The product gave the following data: Mass M + H 530.
f) DMF(1 ml) was added as a solvent and a large excess of the amine was used. The product gave the following data: Mass M + H 514.

TABLE V-continued g) DMF(1 ml) was added as a solvent and a large excess of the amine was used. The product gave the following data: Mass M + H 528.

h) One equivalent of triethylamine and 2 equivalents of morpholine were added and N-methylpyrrolidin-2-one (1 ml) was added as a solvent. The reaction product was purified by column chromatography on silica using increasingly polar mixtures of ethyl acetate and methanol as eluent. The resultant product gave the following data: NMR(DMSOd$_6$) 0.95–1.0 (m, 6H), 2.2(s, 3H), 2.4–2.55(m, 4H), 3.5–3.6(m, 6H), 3.65–3.75(m, 4H), 7.05–7.1(m, 1H), 7.15–7.3(m, 2H), 7.4– 7.6(m, 3H), 7.75–7.8(m, 1H), 7.9–7.95(m, 2H), 9.8(s, 1H), 10.33(s, 1H); Mass M + H 536.

The N-[3-(4-diethylaminomethylbenzamido)-4-methylphenyl]-2,6-dichloropyridine-4-carboxamide used as a starting material was prepared as follows:
2,6-Dichloropyridine-4-carbonyl chloride(1.5 g) and triethylamine (2.3 ml) were added in turn to a stirred mixture of N-(5-amino-2-methylphenyl)-4-diethylaminomethylbenzamide(1.71 g) and methylene chloride (47 ml). The resultant mixture was stirred at ambient temperature for 16 hours. The mixture was evaporated and the residue was partitioned between methylene chloride and a saturated aqueous solution of sodium bicarbonate. A solid was formed which was insoluble in either phase. The solid was isolated, washed with water and dried. There was thus obtained the required starting material (2.66 g): NMR(DMSOd$_6$) 1.0(t, 6H), 2.2(s, 3H), 2.4–2.5(m, 4H), 3.6(s, 2H), 7.25(d, 1H), 7.45(d, 2H), 7.55(d, 1H), 7.8(s, 1H), 7.9(d, 2H), 8.0 (s, 2H), 9.8(s, 1H); Mass M + H 485.

i) One equivalent of triethylamine and 2 equivalents of pyrrolidine were added and N-methylpyrrolidin-2-one (1 ml) was added as a solvent. The reaction product was purified by column chromatography on silica using increasingly polar mixtures of ethyl acetate and methanol as eluent. The resultant product gave the following data: NMR(DMSOd$_6$) 0.95–1.0 (m, 6H), 1.9–2.0(m, 4H), 2.2(s, 3H), 2.4–2.5(m, 4H), 3.4–3.5(m, 4H), 3.6(s, 2H), 6.8(s, 1H), 7.0(s, 1H), 7.2– 7.25(m, 1H), 7.4–7.45(m, 2H), 7.5–7.6(m, 1H), 7.75–7.8(m, 1H), 7.9–7.95(m, 2H), 9.8(s, 1H), 10.3(s, 1H); Mass M + H 520.

j) One equivalent of triethylamine and 2 equivalents of piperidine were added and N-methylpyrrolidin-2-one (1 ml) was added as a solvent. The reaction product was purified by column chromatography on silica using increasingly polar mixtures of ethyl acetate and methanol as eluent. The resultant product gave the following data: NMR(DMSOd$_6$) 1.0(t, 6H), 1.5–1.7(m, 6H), 2.2(s, 3H), 2.4–2.55(m, 4H), 3.5–3.65(m, 6H), 7.0(s, 1H), 7.15(s, 1H), 7.2–7.25(m 1H), 7.4–7.6(m, 3H), 7.8(s, 1H), 7.9–8.0(m, 2H), 9.8(s, 1H), 10.3(s, 1H); Mass M + H 534.

k) One equivalent of triethylamine and 2 equivalents of morpholine were added and N-methylpyrrolidin-2-one (1 ml) was added as a solvent. The reaction product was purified by column chromatography on silica using increasingly polar mixtures of ethyl acetate and methanol as eluent. The resultant product gave the following data: NMR(DMSO$_6$) 2.15(s, 3H), 2.2(s, 3H), 2.3–2.5(m, 8H), 3.5–3.6(m, 6H), 3.65–3.75(m, 4H), 7.05–7.1(m, 1H), 7.15–7.3(m, 2H), 7.4– 7.6(m, 3H), 7.75–7.9(m, 3H), 9.9(s, 1H), 10.33(s, 1H); Mass M + H 563.

The N-{3-[3-(4-methylpiperazin-1-ylmethyl)benzamido]4-methylphenyl}-2,6-dichloropyridine-4-carboxamide used as a starting material was prepared by the reaction of N-(5-amino-2-methylphenyl)-3-(4-methylpiperazin-1-ylmethyl)benzamide and 2,6-dichloropyridine-4-carbonyl chloride using an analogous procedure to that described in the portion of Example 23 which is concerned with the preparation of starting materials. The required starting material gave the following data: NMR(DMSOd$_6$) 2.2(s, 6H), 2.4(brs, 8H), 3.55(s, 2H), 7.25(d, 1H), 7.4–7.6(m, 3H), 7.8–7.9(m, 3H), 8.0(s, 2H), 9.9(s, 1H), 10.6(s, 1H); Mass M + H 512.

l) One equivalent of triethylamine and 2 equivalents of pyrrolidine were added and N-methylpyrrolidin-2-one (1 ml) was added as a solvent. The reaction product was purified by column chromatography on silica using increasingly polar mixtures of ethyl acetate and methanol as eluent. The resultant product gave the following data: NMR(DMSOd$_6$) 1.9–2.0(m, 4H), 2.15(s, 3H), 2.2(s, 3H). 2.3–2.5(m, 8H), 3.4–3.5(m, 4H), 3.5–3.55(m, 2H), 6.85(s, 1H), 7.0(s, 1H), 7.2–7.3(m, 1H), 7.4–7.6(m, 3H), 7.75–7.9(m, 3H), 9.9(s, 1H), 10.3(s, 1H); Mass M + H 547.

m) DMF (1 ml) was added as a solvent and a large excess of the amine was used. The product gave the following data: Mass M + H 557.

n) DMF (1 ml) was added as a solvent and a large excess of the amine was used. The product gave the following data: Mass M + H 557.

o) DMF (1 ml) was added as a solvent and a large excess of the amine was used. The product gave the following data: Mass M + H 541.

p) DMF (1 ml) was added as a solvent and a large excess of the amine was used. The product gave the following data: Mass M + H 511.

q) DMF (1 ml) was added as a solvent and a large excess of the amine was used. The product gave the following data: Mass M + H 499.

r) The product gave the following data: NMR(DMSOd$_6$) 1.45–1.55(m, 4H), 1.7–1.8(m, 4H), 2.15–2.2(m, 6H), 2.3–2.5(m, 8H), 3.55(s, 2H), 3.6–3.7(m, 4H), 6.9–6.95(m, 1H), 6.95–7.0(m, 1H), 7.2–7.25(m, 1H), 7.4–7.6(m, 3H), 7.75–7.8(m, 1H), 7.85–7.9(m, 2H), 8.15–8.2(m, 1H), 9.9(s, 1H), 10.22(s, 1H); Mass M + H 541.

s) The product gave the following data: NMR(DMSOd$_6$) 0.95(t, 6H), 2.2(s, 3H), 2.35–2.5(m, 4H), 3.55–3.6(m, 2H), 3.65–3.7(m, 8H), 7.2–7.25(m, 1H), 7.35–7.4(m, 1H), 7.4–7.45(m, 2H), 7.6–7.65(m, 1H), 7.85–7.95(m, 3H), 8.65(s, 1H), 9.85(s, 1H), 10.49(s, 1H); Mass M + H 503.

The N-[3-(4-diethylaminomethylbenzamido)-4-methylphenyl]-6-chloropyrimidine-4-carboxamide used as a starting material was prepared by the reaction of N-(5-amino-2-methylphenyl)-4-diethylaminomethylbenzamide and 6-chloropyrimidine-4-carbonyl chloride using an analogous procedure to that described in the portion of Example 23 which is concerned with the preparation of starting materials. The reaction product was purified by column chromatography on silica using increasingly polar mixtures of ethyl acetate and methanol as eluent. The resultant required starting material gave the following data NMR (DMSOd$_6$) 1.0 (t, 6H), 2.2 (s, 3H), 2.4–2.5 (m, 4H), 3.6 (s, 2H), 7.2–7.25 (d, 1H), 7.4–7.45 (d, 2H), 7.6–7.65 (m, 1H), 7.9–8.0 (m, 3H), 8.2 (s, 1H), 9.25 (s, 1H), 9.85 (s, 1H); Mass M+H 452.

The 6-chloropyrimidine-4-carbonyl chloride used as a starting material was prepared as follows:

Phosphorus oxychloride (10 ml) was added carefully to a stirred sample of 6-hydroxypyrimidine-4-carboxylic acid (1 g) and the mixture was heated to reflux for 16 hours. Phosphorus pentachloride (5.8 g) was added and the resultant mixture was heated to reflux for a further 16 hours. The excess of phosphorus oxychloride was evaporated under reduced pressure and the residue was distilled. A solid formed in the cooling condenser. There was thus obtained 6-chloropyrimidine-4-carboxylic acid (0.5 g); NMR (DMSOd$_6$) 8.07 (s, 1H), 9.2 (s, 1H), 14.0–14.3 (br s, 1H).

Oxalyl chloride (0.36 ml) was added to a stirred mixture of 6-chloropyrimidine-4-carboxylic acid (0.5 g), DMF (1 drop) and methylene chloride (13 ml) which had been cooled to 0° C. The resultant mixture was stirred at ambient temperature for 4.5 hours and evaporated to give the required starting material which was used without further purification.

EXAMPLE 25

N-[4-methyl-3-(3-morpholino-5-trifluoromethylbenzamido)phenyl]-2-morpholinopyridine-4-carboxamide 3-Morpholino-5-trifluoromethylbenzoyl chloride (0.226 g; obtained by the reaction of 3-morpholino-5-trifluoromethylbenzoic acid and oxalyl chloride using a conventional procedure) was added to a stirred mixture of N-(3-amino-4-methylphenyl)-2-morpholinopyridine-4-carboxamide (0.207 g), triethylamine (0.21 ml) and methylene chloride (20 ml) and the reaction mixture was stirred at ambient temperature for 16 hours. The organic phase was washed with water and with a saturated aqueous sodium bicarbonate solution, dried over sodium sulphate and evaporated. The residue was purified by column chromatography on silica using a 49:1 mixture of methylene chloride-and methanol as eluent. There was thus obtained the title compound as a solid (0.183 g); NMR Spectrum: (DMSOd$_6$) 2.18 (s, 3H), 3.25 (t, 4H), 3.5 (t, 4H), 3.7 (t, 4H), 3.78 (t, 4H), 7.09 (d, 1H), 7.21 (s, 2H), 7.25 (d, 1H), 7.37 (s, 1H), 7.56 (m, 1H), 7.64 (s, 1H), 7.76 (m, 2H), 8.13 (d, 1H), 10.09 (s, 1H), 10.29 (s, 1H); Mass Spectrum: M+H$^+$ 570.

The 3-morpholino-5-trifluoromethylbenzoic acid used as a starting material was prepared as follows:

Ethyl 3-morpholino-5-trifluoromethylbenzoate was prepared from ethyl 3-fluoro-5-trifluoromethylbenzoate by the method described by Brown et al., *Tetrahedron Lett.*, 1999, 40, 1219. The material so obtained compound gave the following data: NMR Spectrum: (CDCl$_3$) 1.36 (t, 3H), 3.19 (t, 4H), 3.81 (t, 4H), 4.34 (m, 2H), 7.22 (d, 1H), 7.72 (d, 1H), 7.76 (s, 1H).

A mixture of ethyl 3-morpholino-5-trifluoromethylbenzoate (0.67 g), 1N aqueous sodium hydroxide solution (3.3 ml) and ethanol (6 ml) was stirred and heated to reflux for 15 minutes and then left to stand for 16 hours. The ethanol was evaporated and the residue was dissolved in water (6 ml). Hydrochloric acid (1 M, 3.3 ml) was added and the resultant solid was isolated, washed with water and dried. There was thus obtained 3-morpholino-5-trifluoromethylbenzoic acid as a solid (0.464 g); NMR Spectrum: (DMSOd$_6$) 3.25 (t, 4H), 3.73 (t, 4H), 7.4 (s, 1H), 7.53 (s, 1H), 7.65 (s, 1H), 13.3 (s, 1H).

EXAMPLE 26

N-[4-methyl-3-(3-piperidin-4-yloxybenzamido)phenyl]-2-morpholinopyridine-4-carboxamide 1-(3-Dimethylaminopropyl)-3-ethylcarbodiimide hydrochloride (0.23 g) was added to a stirred mixture of 3-(1-tert-butoxycarbonylpiperidin-4-yloxy)benzoic acid (0.32 g), N-(3-amino-4-methylphenyl)-2-morpholinopyridine-4-carboxamide (0.312 g), 1-hydroxybenzotriazole (0.202 g) and DMF (5 ml) which had been cooled to 0° C. The reaction mixture was allowed to come to ambient temperature and was stirred for 16 hours. The reaction mixture was partitioned between ethyl acetate and water. The organic phase was washed with water and with a saturated aqueous sodium bicarbonate solution, dried over magnesium sulphate and evaporated. There was thus obtained N-{3-[3-(1-tert-butoxycarbonylpiperidin-4-yloxy)benzamido]-4-methylphenyl}-2-morpholinopyridine-4-carboxamide (0.46 g); NMR Spectrum: (DMSOd$_6$) 1.4 (s, 9H), 1.52 (m, 2H), 1.97 (m, 2H), 2.19 (s, 3H), 3.2 (m, 2H), 3.5 (t, 4H), 3.63 (m, 2H), 3.70 (t, 4H), 4.62 (m, 1H), 7.1 (d, 1H), 7.18 (m, 1H), 7.22 (d, 2H), 7.41 (t, 1H), 7.57 (in, 3H), 7.78 (d, 1H), 8.79 (d, 1H), 9.85 (s, 1H), 10.29 (s, 1H); Mass Spectrum: M+H$^+$ 616.

Trifluoroacetic acid (1 ml) was added to a stirred solution of a portion (0.308 g) of the material so obtained in methylene chloride (1 ml) which had been cooled to 0° C. The reaction mixture was stirred at ambient temperature for 18 hours. The mixture was evaporated and the residue was triturated under diethyl ether. The solid so obtained was dissolved in water (5 ml) and basified by the addition of potassium carbonate. The resultant precipitate was collected, washed with water and dried under vacuum to give the title compound (0.215 g); NMR Spectrum: (DMSOd$_6$) 1.38 (m, 2H), 1.83 (m, 2H), 2.12 (s, 3H), 2.45 (m, 2H), 2.84 (m, 2H), 3.42 (t, 4H), 3.62.(t, 4H), 4.41 (m, 1H), 7.01 (d, 1H), 7.08 (d, 1H), 7.17 (m, 2H), 7.33 (t, 1H), 7.41 (m, 2H), 7.47 (m 1H), 7.7 (d, 1H), 8.18 (d, 1H), 9.78 (s, 1H), 10.22 (s, 1H); Mass Spectrum: M+H$^+$ 516.

The 3-(1-tert-butoxycarbonylpiperidin-4-yloxy)benzoic acid used as a starting material was obtained as follows:

N-tert-Butoxycarbonyl-4-hydroxypiperidine was obtained from a commercial source, for example from Neosystem, F67100, Strasbourg, France, or was prepared by the following procedure. A solution of di-tert-butyl dicarbonate (53.9 g) in methylene chloride (100 ml) was added dropwise to a stirred mixture of 4-hydroxypiperidine (25 g), triethylamine (50 ml) and methylene chloride (250 ml) which had been cooled to 0° C. The resultant mixture was allowed to warm to ambient temperature and was stirred for 18 hours. The mixture was evaporated and the residue was purified by chromatography on silica a 2:1 mixture of isohexane and ethyl acetate as eluent. The oil so obtained was dried under vacuum at 60° C. to give N-tert-butoxycarbonyl-4-hydroxypiperidine as a white solid (49.1 g); NMR Spectrum: (DMSOd$_6$) 1.39 (s, 9H), 1.55 (m, 2H), 1.78 (m, 2H), 2.95 (m, 2H), 3.76 (m, 2H).

Diethyl azodicarboxylate (1.95 ml) was added dropwise over 5 minutes to a stirred mixture of N-tert-butoxycarbonyl-4-hydroxypiperidine (2 g), ethyl 3-hydroxybenzoate (1.66 g), triphenylphosphine (3.2 g) and THF (40 ml) which had been cooled to 0° C. The mixture was stirred at ambient temperature for 40 hours. The solvent was evaporated and the residue was triturated under a 9:1 mixture (40 ml) of isohexane and ethyl acetate. The mixture was filtered and the filtrate was evaporated. The residue was purified by column chromatography on silica using a 9:1 mixture (40 ml) of isohexane and ethyl acetate as eluent. There was thus obtained ethyl 3-(1-tert-butoxycarbonylpiperidin-4-yloxy)benzoate as an oil (1.82 g); NMR Spectrum: (CDCl$_3$) 1.41 (t, 3H), 1.46 (s, 9H), 1.93 (m, 2H), 3.38 (m, 2H), 3.7 (m, 2H), 4.36 (q, 2H), 4.52 (m, 1H). 7.1 (m, 1H), 7.35 (t, 3H), 7.58 (s, 1H), 7.62 (d, 1H).

Sodium hydroxide solution (10M; 1.0 ml) was added to a solution in ethanol (10 ml) of the ester so obtained and the mixture was stirred at ambient temperature for 18 hours. The mixture was evaporated and the residue was dissolved in water (5 ml). A 1M aqueous hydrochloric acid solution (10 ml) and glacial acetic acid (1 ml) were added in turn and the mixture was extracted with methylene chloride. The organic phase was dried over magnesium sulphate and evaporated to give the required starting material as a colourless solid (1.32 g), m.p. 148–150° C.; Mass Spectrum: M+H$^+$ 322.

EXAMPLE 27

N-{3-[3-(1-tert-butoxycarbonylpyrrolidin-3-yloxy) benzamido]-4-methylphenyl}-2-morpholinopyridine4-carboxamide and N-[4-methyl-3-(3-pyrrolidin-3-yloxybenzamido)phenyl]-2-morpholinopyridine-4-carboxamide Using an analogous procedure to that described in the first paragraph of Example 26, 3-(1-tert-butoxycarbonylpyrrolidin-3-yloxy)benzoic acid was reacted with N-(3-amino4-methylphenyl)-2-morpholinopyridine4-carboxamide to give N-{3-[3-(1-tert-butoxycarbonylpyrrolidin-3-yloxy)benzamido]-4-methylphenyl}-2-morpholinopyridine-4-carboxamide; NMR Spectrum: (DMSOd$_6$) 1.42 (s, 9H), 2.15 (s, 2H), 2.22 (s, 3H), 3.44 (m, 3H), 3.55 (t, 4H), 3.6 (m, 1H), 3.77 (t, 4H), 5.18 (m, 1H), 7.13 (d, 1H), 7.21 (m, 1H), 7.37 (m, 2H), 7.5 (t, 1H), 7.56 (s, 1H), 7.61 (d, 2H), 7.81 (d, 1H), 8.3 (d, 1H), 9.9 (s, 1H), 10.31 (s, 1H); Mass Spectrum: M+H$^+$ 602.

The product so obtained was treated with trifluoroacetic acid using an analogous procedure to that described in the second paragraph of Example 26. There was thus obtained the second title compound; NMR Spectrum: (DMSOd$_6$) 1.75 (m, 1H), 1.97 (m, 1H), 2.19 (s, 3H), 2.8 (m, 3H), 3.05 (m, 1H), 3.15 (s, 1H), 3.47 (t, 4H), 3.7 (t, 4H), 4.92 (m, 1H), 7.08 (d, 2H), 7.19 (d, 1H), 7.21 (s, 1H), 7.37 (t, 1H), 7.42 (s, 1H), 7.56 (m, 2H), 7.71 (s, 1H), 8.25 (d, 1H), 9.91 (s, 1H), 10.4 (s, 1H); Mass Spectrum: M+H$^+$ 502.

The 3-(1-tert-butoxycarbonylpyrrolidin-3-yloxy)benzoic acid used as a starting material was obtained as follows:

Using an analogous procedure to that described in the second paragraph of the portion of Example 26 which is concerned with the preparation of starting materials, N-tert-butoxycarbonyl-3-hydroxypyrrolidine (*J. Amer. Chem. Soc.,* 1982, 104, 5852–5853) was reacted with ethyl 3-hydroxybenzoate. The product so obtained was hydrolysed with sodium hydroxide using an analogous procedure to that described in the third paragraph of the portion of Example 26 which is concerned with the preparation of starting materials. There was thus obtained the required starting material; NMR Spectrum: (DMSOd6) 1.38 (s, 9H), 2.06 (m, 2H), 3.1 (m, 3H), 3.55 (m, 1H), 5.03 (br s, 1H), 7.18 (m, 1H), 7.38 (m, 2H), 7.52 (d, 1H); Mass Spectrum: M+H$^+$ 308.

EXAMPLE 28

N-[4-methyl-3-(4-methoxy-3-piperidin-4-yloxybenzamido)phenyl]-2-morpholinopyridine4-carboxamide Using an analogous procedure to that described in the first paragraph of Example 26, 3-(1-tert-butoxycarbonylpiperidin-4-yloxy)-4-methoxybenzoic acid was reacted with N-(3-amino4-methylphenyl)-2-morpholinopyridine-4-carboxamide to give N-{3-[3-(1-tert-butoxycarbonylpiperidin-4-yloxy)4-methoxybenzamido]-4-methylphenyl}-2-morpholinopyridine-4-carboxamide; NMR Spectrum: (DMSOd$_6$) 1.38 (s, 9H), 1.72 (m, 2H), 1.85 (m, 2H), 2.21 (s, 3H), 3.15 (m, 2H), 3.5 (t, 4H), 3.76 (m, 6H), 3.83 (s, 1H), 4.41 (m, 1H), 6.84 (d, 1H), 6.87 (d, 1H), 7.01 (s, 1H), 7.16 (d, 1H), 7.37 (m, 1H), 7.44 (d, 1H), 7.57 (m, 2H), 8.03 (d, 1H), 8.21 (d, 1H), 9.8 (s, 1H), 10.22 (s, 1H); Mass Spectrum: M+H$^+$ 646.

The product so obtained was treated with trifluoroacetic acid using an analogous procedure to that described in the second paragraph of Example 26. There was thus obtained the title compound; NMR Spectrum: (DMSOd$_6$) 1.44 (m, 2H), 1.86 (m, 2H), 2.19 (s, 3H), 2.45 (m, 2H), 2.97 (m, 2H), 3.42 (t, 4H), 3.7 (t, 4H), 3.82 (s, 3H), 4.38 (m, 1H), 7.07 (d, 1H), 7.07 (d, 1H), 7.21 (m, 2H), 7.57 (m, 3H), 7.78 (d, 1H), 8.13 (d, 1H), 9.75 (s, 1H), 10.3 (s, 1H); Mass Spectrum: M+H$^+$ 546.

The 3-(1-tert-butoxycarbonylpiperidin-4-yloxy)-4-methoxybenzoic acid used as a starting material was obtained by the reaction of N-tert-butoxycarbonyl-4-hydroxypiperidine and ethyl 3-hydroxy4-methoxybenzoate (*J. Amer. Chem. Soc.,* 1953, 7, 2630–2631) using an analogous procedure to that described in the portion of Example 26 which is concerned with the preparation of starting materials. There was thus obtained the required starting material as a solid; NMR Spectrum: (DMSOd$_6$) 1.2 (s, 9H), 1.5 (m, 2H), 1.85 (m, 2H), 3.18 (m, 2H), 3.64 (m, 2H), 3.81 (s, 3H), 4.48 (m, 1H), 7.05 (d, 1H), 7.48 (m, 1H), 7.58 (m, 1H); Mass Spectrum: M–$^-$ 350.

EXAMPLE 29

N-{3-[4-(1-tert-butoxycarbonylpiperidin-4-yloxy) benzamido]-4-methylphenyl}-2-morpholinopyridine-4-carboxamide and N-[4-methyl-3-(4-piperidin-4-yloxybenzamido)phenyl]-2-morpholinopyridine-4-carboxamide Using an analogous procedure to that described in the first paragraph of Example 26, 4-(1-tert-butoxycarbonylpiperidin-4-yloxy)benzoic acid was reacted with N-(3-amino4-methylphenyl)-2-morpholinopyridine-4-carboxamide for 48 hours. The reaction product was purified by column chromatography using a 3:1 mixture of isohexane and ethyl acetate as eluent. There was thus obtained N-{3-[4-(1-tert-butoxycarbonylpiperidin-4yloxy)benzamido]-4-methylphenyl}-2-morpholinopyridine-4-carboxamide; NMR Spectrum: (DMSOd$_6$) 1.4 (s, 9H), 1.52 (m, 2H), 1.92 (m, 2H), 2.18 (s, 3H), 3.19 (m, 2H), 3.51 (t, 4H), 3.65 (m, 2H), 3.7 (t, 4H), 4.66 (m, 1H), 7.09 (m, 3H), 7.23 (m, 2H), 7.55 (m, 1H), 7.53 (m, 2H), 7.77 (d, 1H), 7.93 (d, 2H), 8.26 (d, 1H), 9.7 (s, 1H), 10.27 (s, 1H); Mass Spectrum: M+H$^+$ 616.

The product so obtained was treated with trifluoroacetic acid using an analogous procedure to that described in the second paragraph of Example 26. The excess of trifluoroacetic acid was evaporated. The residue was dissolved in water and basified to pH10 by the addition of aqueous sodium hydroxide solution. The resultant precipitate was extracted into methylene chloride. The organic solution was washed with water, dried over magnesium sulphate and evaporated. The material so obtained was purified by column chromatography using increasingly polar mixtures of methylene chloride and methanol and then a 90:9:1 mixture of methylene chloride, methanol and a a saturated aqueous ammonium hydroxide solution as eluent. The oil so obtained was triturated under diethyl ether. The solid so obtained was washed with diethyl ether and dried under vacuum at 60° C. There was thus obtained the second title compound: NMR Spectrum: (DMSOd₆) 1.46 (m, 2H), 1.95 (m, 2H), 2.18 (s, 3H), 2.55 (m, 2H), 2.94 (m, 2H), 3.5 (t, 4H), 3.7 (t, 4H), 4.51 (m, 1H), 7.03 (d, 2H), 7.09 (d, 1H), 7.21 (m, 2H), 7.53 (m, 2H), 7.77 (d, 1H), 7.92 (d, 2H), 8.26 (d, 1H), 9.7 (s, 1H), 10.26 (s, 1H); Mass Spectrum: M+H⁻ 516.

The 4-(1-tert-butoxycarbonylpiperidin-4-yloxy)benzoic acid used as a starting material was obtained as follows:

Using an analogous procedure to that described in the second paragraph of the portion of Example 26 which is concerned with the preparation of starting materials, N-tert-butoxycarbonyl-4-hydroxypiperidine was reacted with ethyl 4-hydroxybenzoate and the crude reaction product was purified by column chromatography on silica using increasingly polar mixtures of methylene chloride and methanol as eluent. The product so obtained was hydrolysed with sodium hydroxide using an analogous procedure to that described in the third paragraph of the portion of Example 26 which is concerned with the preparation of starting materials. There was thus obtained the required starting material; NMR Spectrum: (DMSO$_d$) 1.38 (s, 9H), 1.51 (m, 2H), 1.9 (m, 2H), 3.15 (m, 2H), 3.64 (m, 2H), 4.65 (m, 1H), 7.03 (d, 2H), 7.84 (d, 2H); Mass Spectrum: M+H⁺ 322.

EXAMPLE 30

N-{4-methyl-3-[4-(2-methylthiazol4-ylmethoxy)benzamido]phenyl}-2-morpholinopyridine-4-carboxamide Using an analogous procedure to that described in the first paragraph of Example 26, 4-(2-methylthiazol4-ylmethoxy)benzoic acid was reacted with N-(3-amino4-methylphenyl)-2-morpholinopyridine-4-carboxamide. The reaction product was purified by column chromatography on silica using a 97:3 mixture of methylene chloride and methanol as eluent. There was thus obtained to give the title compound; NMR Spectrum: (DMSOd₆) 2.2 (s, 3H), 2.44 (s, 3H), 3.5 (t, 4H), 3.7 (t, 4H), 5.19 (s, 2H), 7.11 (m, 3H), 7.23 (m, 2H), 7.4 (t, 2H), 7.54 (m, 3H), 7.68 (d, 1H), 7.78 (d, 1H), 7.96 (d, 2H), 8.24 (d, 1H), 9.73 (s, 1H), 10.27 (s, 1H); Mass Spectrum: M+H⁺ 544.

The 4-(2-methylthiazol-4-ylmethoxy)benzoic acid used as a starting material was obtained as follows:

A mixture of 4-chloromethyl-2-methylthiazole (13.3 g), ethyl 4-hydroxybenzoate (10 g), potassium carbonate (24.9 g) and DMA (200 ml) was stirred and heated to 80° C. for 18 hours. The mixture was cooled to ambient temperature and poured into water (1300 ml). The resultant precipitate was isolated and dried. There was thus obtained ethyl 4-(2-methylthiazol-4-ylmethoxy)benzoate (15.34 g); NMR Spectrum: (DMSOd₆) 1.38 (t, 3H), 2.74 (s, 3H), 4.35 (m, 2H), 5.2 (s, 2H), 7.01 (d, 2H), 7.15 (s, 1H), 7.99 (d, 2H).

A mixture of the material so obtained, sodium hydroxide pellets (3.33 g), water (8 ml) and ethanol (300 ml) was stirred at ambient temperature for 18 hours. Water (50 ml) was added and the bulk of the ethanol was evaporated. The residue was acidified to pH4 by the addition of 1N aqueous hydrochloric acid solution. The precipitate was isolated and dried. There was thus obtained the required starting material (13.23 g); NMR Spectrum: (DMSOd₆) 2.63 (s, 3H), 5.17 (s, 2H), 7.09 (d, 2H), 7.58 (s, 1H), 7.87 (d, 1H), 12.58 (br s, 1H).

EXAMPLE 31

Using an analogous procedure to that described in Example 7, the appropriate N-[3-(3-hydroxybenzamido)-4-methylphenyl]heteroarylcarboxamide was reacted with the appropriate alkyl chloride to give the compounds described in Table VI.

TABLE VI

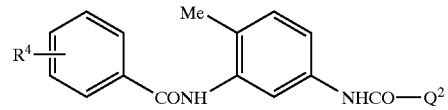

| No. | R⁴ | Q² | Note |
|-----|----|----|------|
| 1 | 3-(2-piperidinoethoxy) | 2-morpholinopyrid-4-yl | a |
| 2 | 3-(3-piperidinopropoxy) | 2-morpholinopyrid-4-yl | b |
| 3 | 3-(2-pyrrolidin-1-ylethoxy) | 2-morpholinopyrid-4-yl | c |
| 4 | 3-(2-diethylaminoethoxy) | 2-morpholinopyrid-4-yl | d |
| 5 | 3-[2-methyl-pyrrolidin-2-yl)ethoxy] | 2-morpholinopyrid-4-yl | e |
| 6 | 3-(N-methylhomo-piperidin-4-yloxy) | 2-morpholinopyrid-4-yl | f |

Notes
a) The product gave the following data: NMR(DMSOd₆) 1.35(m, 2H), 1.46(m, 4H), 2.19(s, 3H), 2.42(t, 4H), 2.65(t, 2H), 3.5(t, 4H), 3.69(t, 4H), 4.15(t, 2H), 7.12(m, 2H), 7.23(d, 2H), 7.42(t, 1H), 7.55(m, 3H), 7.73(d, 1H), 8.24(d, 1H) 9.84(s, 1H), 10.28(s, 1H); Mass M + H 544.
The N-[3-(3-hydroxybenzamido)-4-methylphenyl]-2-morpholinopyridine-4-carboxamide used as a starting material was prepared as follows:
3-Benzyloxybenzoyl chloride [obtained by the reaction of 3-benzyloxybenzoic acid (1.7 g) and oxalyl chloride (0.77 ml) using a conventional procedure] was added to a stirred mixture of N-(3-amino-4-methylphenyl)-2-morpholinopyridine-4-carboxamide (1.94 g), pyridine (1.05 ml) and methylene chloride (45 ml) and the reaction mixture was stirred at ambient temperature for 18 hours. The precipitate so obtained was isolated and dried. There was thus obtained N-[3-(3-benzyloxybenzamido)-4-methylphenyl]-2-morpholinopyridine-4-carboxamide as a solid (2.95 g); NMR (DMSOd₆) 2.21(s, 3H), 3.64(d, 4H), 3.75(d, 4H), 5.18(s, 3H), 7.22(m, 3H), 7.4(m, 6H), 7.57(m, 4H), 7.81 (s, 1H), 8.21(d, 1H), 9.9(s, 1H), 10.53(s, 1H); Mass M + H 523.
A mixture of the material so obtained, 10% palladium-on-carbon (0.3 g) and methanol (450 ml) was stirred under an atmosphere of hydrogen gas for 18 hours. The mixture was filtered and the filtrate was evaporated. The residue was purified by column chromatography on silica using a 9:1 mixture of methylene chloride and methanol as eluent. There was thus obtained the required starting material (1.2 g); NMR(DMSOd₆) 2.19(s, 3H), 3.49(t, 4H), 3.7(t, 4H), 6.95(m, 1H), 7.09(d, 1H), 7.3(m, 4H), 7.4(d, 1H), 7.57(m, 1H), 7.78(d, 1H), 8.24(d, 1H), 9.67(s, 1H), 9.78(s, 1H), 10.27(s, 1H); Mass M + H⁺ 433.
b) The product gave the following data: NMR(DMSOd₆) 1.36(d, 2H), 1.46 (m, 2H), 1.86(m, 2H), 2.19(s, 3H), 2.39(m, 6H), 3.5(t, 4H), 3.69(t, 4H), 4.04(t, 2H), 7.11(m, 2H), 7.22(m, 2H), 7.41(t, 1H), 7.54(t, 3H), 8.23(d, 1H), 9.86(s, 1H), 10.28(s, 1H); Mass M + H 558.
c) The product gave the following data: NMR(DMSOd₆) 1.65(m, 4H), 2.19(s, 3H)⁺, 2.82(t, 2H), 3.51(t, 4H), 3.69(t, 4H), 4.15(t, 2H), 7.1(m, 2H), 7.23(m, 2H), 7.41(t, 1H), 7.53(m, 3H), 7.78(s, 1H), 8.23(d, 1H), 9.83(s, 1H), 10.27(s, 1H); Mass M + H 530.
d) The product gave the following data: NMR(DMSOd₆) 0.96(t, 6H), 2.19 (s, 3H), 2.57(m, 4H), 2.79(t, 2H), 3.5(t, 4H), 3.69(t, 4H), 4.08(t, 2H), 7.1 (m, 2H), 7.22(d, 2H), 7.41(t, 1H), 7.53(m, 3H), 7.77(d, 1H), 8.25(d, 1H), 9.83(s, 1H), 10.28(s, 1H); Mass M + H 532.
e) The reaction product was purified by column chromatography on silica using increasingly polar mixtures of methylene chloride and methanol as eluent The product of Example 31(5) so obtained gave the following data: NMR(DMSOd₆) 1.6(m, 4H), 1.88(m, 1H), 2.07(m, 2H), 2.19(s, 3H), 2.29(s, 3H), 2.98(m, 1H), 3.54(t, 4H), 3.73(t, 4H), 4.14(m, 2H), 7.11(m, 2H), 7.25 (m, 2H), 7.47(m, 4H), 7.82(s, 1H), 8.31(d, 1H), 9.89(s, 1H), 10.3(s, 1H); Mass M + H 544.
f) On further elution of the chromatography column referred to in Note e) immediately above, an isomeric product was obtained. The product of Example 31(6) so obtained gave the following data: NMR(DMSOd₆) 1.62 (m, 1H), 1.84(m, 3H), 2.14(m, 2H), 2.19(s, 3H), 2.28(s, 3H), 2.62(m, 4H), 3.53(t, 4H), 3.71(t, 4H), 4.71(m, 1H), 7.12(m, 2H), 7.24(m, 2H), 7.46(m, 4H), 7.8(s, 1H), 8.29(d, 1H), 9.86(s, 1H), 10.3(s, 1H); Mass M + H 544.

EXAMPLE 32

N-[2-methyl-5(2-morpholinopyrid-4-ylcarbonylamino)phenyl]-3-(4methylpiperazin-1-yl)-2-nitrobenzamide In an analogous procedure to that described in Example 15, N-[2-methyl-5-(2-morpholinopyrid-4ylcarbonylamino)

phenyl]-3-chloro-2-nitrobenzamide was reacted with 1-methylpiperazine to give the title compound; NMR Spectrum: (DMSOd6) 2.84–2.89 (m, 4H), 2.92–3.08 (m, 4H), 3.58–3.61 (m, 4H), 3.81–3.84 (m, 4H), 6.95 (d, 1H), 7.09 (s, 1H), 7.10 (d, 1H), 7.41–7.44 (m, 2H), 7.53 (d, 1H), 7.76 (d, 1H), 7.96 (s, 1H), 8.04 (s, 1H), 8.3 (d, 1H); Mass Spectrum: M+H+ 560.

The N-[2-methyl-5-(2-morpholinopyrid-4-ylcarbonylamino)phenyl]-3-chloro-2-nitrobenzamide used as a starting material was prepared as follows:

Oxalyl chloride (0.377 ml) was added dropwise to a stirred mixture of 3-chloro-2-nitrobenzoic acid (0.726 g), DMF (a few drops) and methylene chloride (25 ml) which had been cooled to 0° C. The mixture was allowed to warm to ambient temperature and was stirred for 5 hours. The mixture was evaporated. The residue was dissolved in methylene chloride (10 ml) and was added dropwise to a stirred mixture of N-(3-amino4-methylphenyl)-2-morpholinopyridine-4-carboxamide (0.933 g), triethylamine (1.12 ml) and methylene chloride (25 ml). The mixture was stirred at ambient temperature for 16 hours. The resultant precipitate was isolated, washed in turn with water, methylene chloride and diethyl ether and dried under vacuum at 40° C. There was thus obtained the required starting material (1.13 g); NMR Spectrum: (DMSOd$_6$) 2.2 (s, 3H), 3.49–3.53 (m, 4H), 3.69–3.73 (m, 4H), 7.1 (d, 1H), 7.18–7.24 (m, 2H), 7.58 (d, 1H), 7.68–7.78 (m, 2H), 7.58 (d, 1H), 7.68–7.78 (m, 2H), 7.84–8.0 (m, 2H), 8.25 (d, 1H); Mass Spectrum M+H+ 496 and 498.

EXAMPLE 33

N-[2-methyl-5-(2-morpholinopyrid-4-ylcarbonylamino)phenyl]-2-amino-3(4-methylpiperazin-1-yl)benzamide In an analogous procedure to that described in Example 16, N-[2-methyl-5-(2-morpholinopyrid-4-ylcarbonylamino)phenyl]-3-(4-methylpiperazin-1yl)-2-nitrobenzamide was reduced catalytically to give the title compound; Mass Spectrum: M+H+ 530.

EXAMPLE 34

N-[2-methyl-5(2-morpholinopyrid-4-ylcarbonylamino)phenyl]-5-(3-dimethylaminopropylamino)-2-nitrobenzamide In an analogous procedure to that described in Example 15, N-[2-methyl-5-(2-morpholinopyrid-4-ylcarbonylamino)phenyl]-5-chloro-2-nitrobenzamide was reacted with 3-dimethylaminopropylamine to give the title compound; NMR Spectrum: (DMSOd$_6$) 1.6–1.72 (m, 2H), 2.12 (s, 6H), 2.22–2.28 (m, 5H), 3.2–3.25 (m, 2H), 3.5–3.54 (m, 4H), 3.69–3.73 (m, 4H), 6.65–6.68 (m, 2H), 7.04 (d, 1H), 7.2 (d, 1H), 7.25 (d, 1H), 7.29 (t, 1H), 7.68 (d, 1H), 8.84 (s, 1H), 8.0 (d, 1H), 8.26 (d, 1H), 9.82 (s, 1H), 10.34 (s, 1H); Mass Spectrum: M+H+ 562.

EXAMPLE 35

N-[2-methyl-5-(2-morpholinopyrid-4ylcarbonylamino)phenyl]-2-amino-5[N-(3-methylaminopropyl)-N-methylamino]benzamide In an analogous procedure to that described in Example 16, N-[2-methyl-5-(2-morpholinopyrid-4-ylcarbonylamino) phenyl]-5-[N-(3-methylaminopropyl)-N-methylamino]-2-nitrobenzamide was reduced catalytically to give the title compound; NMR Spectrum: (DMSOd$_6$) 1.57–1.62 (m, 2H), 2.2 (s, 3H), 2.25 (s, 3H), 2.47–2.5 (m, 2H), 2.77 (s, 3H), 3.19–3.23 (m, 2H), 3.5–3.54 (m, 4H), 3.69–3.73 (m, 4H), 5.6 (s, 2H), 6.68 (d, 1H), 6.82 (d, 1H), 7.04 (s, 1H), 7.1 (d, 1H), 7.2–7.23 (m, 2H), 7.54 (d, 1H), 7.83 (d, 1H), 8.26 (d, 1H), 9.75 (s, 1H), 10.28 (s, 1H); Mass Spectrum: M+H+ 532.

The N-[2-methyl-5-(2-morpholinopyrid-4-ylcarbonylamino)phenyl]-5-N-(3-methylaminopropyl)-N-methylamino]-2-nitrobenzamide used as a starting material was prepared as follows:

In an analogous procedure to that described in Example 15, N-[2-methyl-5-(2-morpholinopyrid-4-ylcarbonylamino) phenyl]-5-chloro-2-nitrobenzamide was reacted with N-(3-methylaminopropyl)-N-methylamine to give the required starting material; NMR Spectrum: (DMSOd$_6$) 1.61–1.74 (m, 2H), 2.35 (s, 3H), 2.26 (m, 3H), 2.38–2.44 (m 2H), 3.09 (s, 3H), 3.5–3.55 (m, 6H), 3.7–3.74 (m, 4H), 6.78 (s, 1H), 6.84 (d, 1H), 7.14 (d, 1H), 7.21 (d, 1H), 7.27 (s, 1H), 7.6 (d, 1H), 7.9 (s, 1H), 8.04 (d, 1H), 8.27 (d, 1H), 9.83 (s, 1H, 10.55 (s, 1H); Mass Spectrum: M+H + 562.

EXAMPLE 36

N-{4-methyl-3-[4-(2-methylthiazol-4-ylmethoxy) benzamido]phenyl}dibenzofuran-4-carboxamide 4-(2-Methylthiazol-4-ylmethoxy)benzoic acid (0.095 g) was added to a stirred mixture of N-(3-amino-4-methylphenyl)dibenzofuran-4-carboxamide (0.12 g), diisopropylethylamine (0.2 ml), 2-(7-azabenzotriazol-1-yl)-1,1,3,3-tetramethyluronium hexafluorophosphate(V) (0.134 g) and methylene chloride (22 ml) and the mixture was stirred at ambient temperature for 16 hours. The mixture was evaporated and the residue was purified by column chromatography on an ion exchange column (isolute SCX column) using initially a 1:1 mixture of ethyl acetate and methanol and then a 99:1 mixture of methanol and a saturated aqueous ammonium hydroxide solution as eluent. The product so obtained was triturated under ethyl acetate. There was thus obtained the title compound (0.051 g); NMR Spectrum: (DMSOd$_6$) 2.25 (s, 3H), 2.65 (s, 3H), 5.2 (s, 2H), 7.15 (d, 2H), 7.25 (d, 1H), 7.4–7.65 (m, 5H), 7.8–7.9 (m, 3H), 7.98 (d, 2H), 8.2 (d, 1H), 8.35 (d, 1H), 9.8 (d, 1H), 10.4 (s, 1H); Mass Spectrum: M+H+ 548.

The N-(3-amino-4-methylphenyl)dibenzofuran-4-carboxamide used as a starting material was prepared as follows:

Dibenzofuran4-carboxylic acid (1 g) was added to a stirred mixture of 4-methyl-3-nitroaniline (0.717 g), diisopropylethylamine (1.64 ml), 2-(7-azabenzotriazol-1-yl)-1,1,3,3-tetramethyluronium hexafluorophosphate(V) (1.79 g) and methylene chloride (50 ml) and the mixture was stirred at ambient temperature for 16 hours. The mixture was evaporated and the residue was partitioned between methylene chloride and a saturated aqueous sodium bicarbonate solution. The organic phase was dried over magnesium sulphate and evaporated. The residue was triturated under isohexane and the resultant solid was isolated. There was thus obtained N-(4-methyl-3-nitrophenyl)dibenzofuran-4-carboxamide (1.22 g); NMR Spectrum: (DMSOd$_6$) 7.4–7.6 (m, 4H), 7.8 (d, 1H), 7.9 (d, 1H), 7.98 (d, 1H), 10.78 (s, 1H); Mass Spectrum: M+H+ 347.

A mixture of the material so obtained, iron powder (1.97 g), glacial acetic acid (0.72 ml), ethanol (36 ml) and water (3.6 ml) was stirred and heated to 100° C. for 5 hours. The reaction mixture was cooled to ambient temperature and water was added. The resultant mixture was basified to pH9 by the addition of solid sodium carbonate and filtered. The filtrate was evaporated and the residue was partitioned between ethyl acetate and water. The organic phase was dried over magnesium sulphate and evaporated. The residue was triturated under isohexane and the resultant solid was isolated. There was thus obtained N-(3-amino-4-methylphenyl)dibenzofuran-4-carboxamide (1.07 g); NMR Spectrum: (DMSOd$_6$) 2.05 (s, 3H), 4.9 (s, 2H), 6.85 (m, 2H), 7.18 (s, 1H), 7.4–7.6 (m, 3H), 7.75–7.85 (m, 2H), 8.2 (d, 1H), 8.3 (d, 1H), 10.03 (s, 1H); Mass Spectrum: M+H$^+$ 317.

EXAMPLE 37

N-{3-[3-(N-isopropylpiperidin-4-yloxy)benzamido]-4-methylphenyl}dibenzofuran-4-carboxamide Oxalyl chloride (0.34 ml) was added to a stirred mixture of 3-(N-isopropylpiperidin-4-yloxy)benzoic acid (0.782 g), DMF (2 drops) and methylene chloride (20 ml) which had been cooled in an ice bath. The resultant mixture was stirred at ambient temperature for 4 hours. The mixture was evaporated and the 3-(N-isopropylpiperidin-4-yloxy)benzoyl chloride so obtained was dissolved in methylene chloride (20 ml).

Triethylamine (0.48 ml) was added to a stirred mixture of a portion (10 ml) of the acid chloride solution, N-(3-amino-4-methylphenyl)dibenzofuran-4-carboxamide (0.36 g) and methylene chloride (10 ml) and the resultant solution was stirred at ambient temperature for 16 hours. The mixture was evaporated and the residue was partitioned between methylene chloride and a saturated aqueous sodium bicarbonate solution. The organic phase was washed with a saturated aqueous sodium chloride solution, dried over magnesium sulphate and evaporated. The residue was purified by column chromatography on silica using increasingly polar mixtures of methylene chloride and methanol as eluent. The material so obtained was dissolved in acetone and reprecipitated by the addition of isohexane. There was thus obtained the title compound (0.06 g); NMR Spectrum: (DMSOd$_6$) 1.0 (d, 6H), 1.55–1.7 (m, 2H), 1.9–2.05 (m, 2H), 2.2 (s, 3H), 2.3–2.45 (m, 2H), 2.7–2.8 (m, 3H), 4.4–4.5 (m, 1H), 7.15 (m, 1H), 7.25 (d, 1H), 7.4–7.65 (m, 7H), 7.8–7.9 (m, 3H), 8.2 (d, 1H), 8.35 (m, 1H), 9.9 (s, 1H); Mass Spectrum: M+H$^+$ 562.

The 3-(N-isopropylpiperidin-4-yloxy)benzoic acid used as a starting material was prepared as follows:

Diethyl azodicarboxylate (2.26 g) was added dropwise to a stirred mixture of N-isopropyl-4-hydroxypiperidine (*Helv. Chim. Acta*, 1966, 46, 693; 1.57 g), ethyl 3-hydroxybenzoate (1.66 g), triphenylphosphine (3.4 g) and THF (40 ml) which had been cooled to 0° C. The mixture was stirred at ambient temperature for 42 hours. The solvent was evaporated and the residue was partitioned between ethyl acetate and 2N aqueous hydrochloric acid. The aqueous phase was washed with ethyl acetate, basified to pH10 by the addition of solid potassium carbonate and extracted with diethyl ether. The organic extract was dried over magnesium sulphate and evaporated to give ethyl 3-(N-isopropypiperidin- 4-yloxy) benzoate as an oil (1.53 g); NMR Spectrum: (CDCl$_3$) 1.06 (d, 6H), 1.38 (t, 3H), 1.8 (m, 2H), 2.07 (m, 2H), 2.41 (m, 2H), 2.72 (m, 1H), 2.78 (m, 2H), 4.38 (m, 2H), 7.08 (m, 1H), 7.32 (t, 1H), 7.57 (d, 1H), 7.62 (d, 1H). The oil so obtained was dissolved in diethyl ether (20 ml) and a 1M solution of hydrogen chloride in diethyl ether (12 ml) was added. The resultant precipitate was isolated to give ethyl 3-(N-isopropypiperidin-4-yloxy)benzoate hydrochloride salt (1.55 g).

Sodium hydroxide (0.48 g) was dissolved in water (5 ml) and the solution was added to a solution of ethyl 3-(N-isopropypiperidin-4-yloxy)benzoate hydrochloride salt (1.55 g) in ethanol (10 ml). The mixture was stirred at ambient temperature for 24 hours. The mixture was evaporated and the residue was dissolved in water (12 ml). A 1M aqueous hydrochloric acid solution (12 ml) was added and the mixture was evaporated. The residue was triturated under methanol. Soluble material was reisolated and triturated under methylene chloride. The resultant solid was isolated and dried. There was thus obtained the required starting material as a colourless solid (0.84 g); NMR Spectrum: (DMSOd$_6$) 1.22 (d, 6H), 2.3 (m, 4H), 3.3 (m, 5H), 4.7 (m, 1H), 7.2 (m, 1H), 7.4 (m, 1H), 7.5 (m, 2H), 11.08 (m, 1H); Mass Spectrum: M+H$^+$ 264.

EXAMPLE 38

N-{3-[3-(4-methylpiperazin-1-ylmethyl)benzamido]-4-methylphenyl}dibenzofuran-4-carboxamide Diisopropylethylamine (0.4 ml) was added to a stirred mixture of N-(5-amino-2-ethylphenyl)-3-(4-methylpiperazin-1-ylmethyl)benzamide (0.2 g), dibenzofuran-4-carboxylic acid (0.133 g), 2-(7-azabenzotriazol-1-yl)-1,1,3,3-tetramethyluronium hexafluorophosphate(V) (0.22 g) and methylene chloride (10 ml) and the mixture was stirred at ambient temperature for 16 hours. The mixture was evaporated and the residue was partitioned between methylene chloride and a saturated aqueous sodium bicarbonate solution. The organic phase was dried over magnesium sulphate and evaporated. The residue was purified by column chromatography on silica using increasingly polar mixtures of methylene chloride and methanol as eluent. The material so obtained was dissolved in acetone and reprecipitated by the addition of isohexane. There was thus obtained the title compound (0.164 g); NMR Spectrum: (DMSOd$_6$) 1.15 (t, 3H), 2.25 (s, 3H), 2.35–2.5 (m, 8H), 2.6 (m, 2H), 3.55 (s, 2H), 7.3 (d, 1H), 7.4–7.6 (m, 5H), 7.65 (m, 1H), 7.8–7.9 (m, 5H), 8.2 (d, 1H), 8.35 (d, 1H), 9.95 (s, 1H), 10.43 (s, 1H); Mass Spectrum: M+H$^+$ 547.

The N-(5-amino-2-ethylphenyl)-3-(4-methylpiperazin-1-ylmethyl)benzamide used as a starting material was prepared as follows:

3-Chloromethylbenzoyl chloride (11.93 g) was added to a stirred mixture of 2-ethyl-5-nitroaniline (10 g), triethylamine (17.3 ml) and methylene chloride (283 ml) and the resultant mixture was stirred at ambient temperature for 16 hours. The mixture was evaporated. Methylene chloride was added to the residue and the resultant precipitate was isolated and washed in turn with 1N aqueous hydrochloric acid, a saturated aqueous sodium bicarbonate solution and diethyl ether. There was thus obtained 3-chloromethyl-N-(2-ethyl-5-nitrophenyl)benzamide (11.14 g); NMR Spectrum: (DMSOd$_6$) 2.77 (m, 2H), 4.05 (s, 2H), 7.5–7.6 (m, 2H), 7.65–7.7 (m, 1H), 7.95–8.0 (m, 1H), 8.05–8.1 (m, 2H), 8.25 (s, 1H), 10.26 (s, 1H).

1-Methylpiperazine (4.27 ml) was added to a stirred mixture of the material so obtained, potassium carbonate (9.7 g) and acetone (500 ml) and the mixture was heated to reflux and stirred for 6 hours. The resultant solution was evaporated and the residue was dissolved in methylene chloride. The organic solution was washed with a saturated aqueous sodium bicarbonate solution, dried over magnesium sulphate and evaporated. There was thus obtained N-(2-ethyl-5-nitrophenyl)-3-(4-methylpiperazin-1-ylmethyl) benzamide (9.69 g); NMR Spectrum: (DMSOd$_6$) 1.2 (t, 3H), 2.15 (s, 3H), 2.3–2.5 (m, 8H), 2.8 (m, 2H), 3.75 (s, 2H), 7.4–7.6 (m, 3H), 7.8–7.9 (m, 2H), 8.05 (m, 1H), 8.3 (s, 1H), 10.13 (s, 1H); Mass Spectrum: M+H$^+$ 383.

Iron powder (14.17 g) was added to a stirred mixture of the material so obtained, ethanol (260 ml), water (26 ml) and glacial acetic acid (5.2 ml). The resultant mixture was stirred and heated to reflux for 8 hours. The mixture was cooled to ambient temperature and basified to pH9 by the addition of solid sodium carbonate. The resultant mixture was filtered and the filtrate was evaporated to dryness. The residue was partitioned between ethyl acetate and water. The organic phase was dried over magnesium sulphate and evaporated. There was thus obtained N-(5-amino-2-ethylphenyl)-3-(4-methylpiperazin- I -ylmethyl)benzamide (7.2 g); NMR Spectrum: (DMSOd$_6$) 1.05 (t, 3H), 2.15 (s, 3H), 2.2–2.5 (m, 10H), 3.5 (s, 2H), 4.9 (s, 2H), 6.45 (m, 1H), 6.55 (d, 1H), 6.9 (d, 1H), 7.4–7.5 (m, 2H), 7.8–7.9 (m, 1H), 9.6 (s, 1H);

Mass Spectrum: 353.

EXAMPLE 39

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 10 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph.Eur | 488.5 |
| | Magnesium | 1.5 |

| (e) | Injection I | (50 mg/ml) |
|---|---|---|
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1M Sodium hydroxide solution | 15.0% v/v |
| | Water for injection to 100% | |

| (g) | Injection III | (1 mg/ml, buffered to pH 6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

| (l) | Ointment | ml |
|---|---|---|
| | Compound X | 40 mg |
| | Ethanol | 300 μl |
| | Water | 300 μl |
| | 1-Dodecylazacycloheptan-2-one | 50 μl |
| | Propylene glycol | to 1 ml |

Note The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate polysorbate 80, polyglycerol oleate or oleic acid.

What is claimed is:
1. An amide derivative of the Formula I

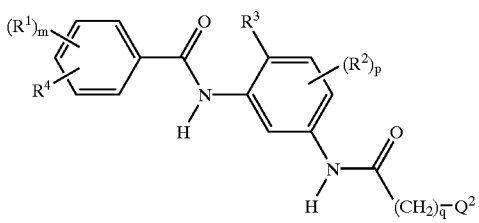

wherein
R³ is (1–6C)alkyl or halogeno;
m is 0, 1, 2 or 3;
R¹ is hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino or di-[(1–6C)alkyl]amino-(2–6C)alkanoylamino,
or R¹ is aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl or heterocyclyl-(2–6C)alkanoylamino, and wherein any aryl, heteroaryl or heterocyclyl group in a R¹ substituent may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

p is 0, 1 or 2;
R² is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino;

R⁴ is amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino or di-[(1–6C)alkyl]amino-(2–6C)alkanoylamino,
or R⁴ is heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl or N-(1–6C)alkyl-heterocyclyl-(1–6C)alkylamino-(1–6C)alkyl, and wherein any of the $R^4$ substituents defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a $R^4$ substituent may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy(1–6C)alkyl, (1–6C)alkoxy(1–6C)alkyl, cyano -6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

q is 0, 1, 2, 3 or 4; and $Q^2$ is heteroaryl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl or heteroaryl-(2–6C)alkanoylamino and $Q^2$ is optionally substituted with 1, 2 or 3 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-( 1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heterocyclylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl and N-(1–6C)alkyl-heterocyclyl-(1–6C)alkylamino-(1–6C)alkyl, and wherein any of the substituents on $Q^2$ defined hereinbefore which comprises a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a substituent on $Q^2$ may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

or a pharmaceutically-acceptable salt or in-vivo-cleavable ester thereof.

2. An amide derivative of the Formula I according to claim 1 wherein $Q^2$ is a heteroaromatic 5- or 6-membered monocyclic ring or a 9- or 10-membered bicyclic ring with up to five ring heteroatoms selected from oxygen, nitrogen and sulphur which bears a basic substituent selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C)alkanoylamino, heteroaryl, heteroaryl-(1–6C)alkyl, heteroaryl-(1–6C)alkoxy, heterocyclyl, heterocyclyl-(1–6C)alkyl and heterocyclyl-(1–6C)alkoxy, and wherein any heteroaryl or heterocyclyl group in a basic substituent on $Q^2$ may optionally bear 1 or 2 substituents selected from halogeno, (1–6C)alkyl, (2–6C)alkanoyl, amino, (1–6C)alkylamino and di-[(1–6C)alkyl]amino.

3. An amide derivative of the Formula I according to claim 1 wherein $Q^2$ is a heteroaromatic 5- or 6-membered monocyclic ring, a 9- or 10-membered bicyclic ring or a 13- or 14-membered tricyclic ring each with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3C)alkylenedioxy, (1–6C)alkylamino, di-[(1–6C)alkyl]amino and (1–6C)alkoxycarbonyl.

4. An amide derivative of the Formula I according to claim 1 wherein $R^4$ is amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, pyridyl, imidazolyl, pyridyl-(1–6C)alkyl, imidazolyl-(1–6C)alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, homopiperazinyl, 4-(1–6C)alkylhomopiperazinyl, 4-(2–6C)alkanoylpiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, homopiperazinyl-(1–6C)alkyl, 4-(1–6C)alkylhomopiperazinyl-(1–6C)alkyl, 4-(2–6C)alkanoylpiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy or 4-(2–6C)alkanoylpiperazinyl-(2–6C)alkoxy.

5. An amide derivative of the Formula I according to claim 1 wherein $R^3$ is methyl, ethyl, chloro or bromo;

m is 0 or 1;

$R^1$ is hydroxy, fluoro, chloro, bromo, trifluoromethyl, cyano, amino, methyl, ethyl, methoxy, ethoxy, methylamino, ethylamino, dimethylamino or diethylamino;

p is 0;

$R^4$ is amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy or 3-(4-acetylpiperazinyl)propoxy;

q is 0; and $Q^2$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothiophenyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, aminomethyl, methylaminomethyl, ethylaminomethyl, dimethylaminomethyl, diethylaminomethyl, 2-hydroxyethoxy, 3-hydroxypropoxy, 2-methoxyethoxy, 2-ethoxyethoxy, 3-methoxypropoxy, 3-ethoxypropoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, pyridyl, pyridylmethyl, pyridylmethoxy, pyrrolidinyl, piperidinyl, morpholinyl, piperazinyl, 4-methylpiperazinyl, 4-acetylpiperazinyl, pyrrolidinylmethyl, piperidinylmethyl, morpholinylmethyl, piperazinylmethyl, 4-methylpiperazinylmethyl, 4-acetylpiperazinylmethyl, piperidinyloxy, 1-methylpiperidinyloxy, 2-(pyrrolidinyl)ethoxy, 3-(pyrrolidinyl)propoxy, 2-(piperidinyl)ethoxy, 3-(piperidinyl)propoxy, 2-(morpholinyl)ethoxy, 3-(morpholinyl)propoxy, 2-(piperazinyl)ethoxy, 3-(piperazinyl)propoxy, 2-(4-methylpiperazinyl)ethoxy, 3-(4-methylpiperazinyl)propoxy, 2-(4-acetylpiperazinyl)ethoxy and 3-(4-acetylpiperazinyl)propoxy;

or a pharmaceutically-acceptable salt thereof.

6. An amide derivative of the Formula I according to claim 1 wherein $R^3$ is methyl;

m is 0 or m is 1 and $R^1$ is hydroxy, fluoro, chloro, amino, methyl, methoxy, methylamino or dimethylamino;

each of p and q is 0;

R⁴ is located at the 3- or 4-position and is selected from dimethylaminomethyl, diethylaminomethyl, 2-dimethylaminoethoxy, 2-diethylaminoethoxy, 3-dimethylaminopropoxy, 3-diethylaminopropoxy, 3-dimethylamino-2-hydroxypropoxy, 3-diethylamino-2-hydroxypropoxy, 2-aminoethylamino, 3-aminopropylamino, 4-aminobutylamino, 3-methylaminopropylamino, 2-dimethylaminoethylamino, 2-diethylaminoethylamino, 3-dimethylaminopropylamino, 4-dimethylaminobutylamino, 3-amino-2-hydroxypropylamino, 3-dimethylamino-2-hydroxypropylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, 4-methylhomopiperazin-1-yl, piperazin-1-ylmethyl, 4-methylpiperazin-1-ylmethyl, 4-methylhomopiperazin-1-ylmethyl, morpholinomethyl, 3-aminopyrrolidin-1-ylmethyl, 3-hydroxypyrrolidin-1-ylmethyl, 4-(2-hydroxyethyl)piperazin-1-ylmethyl, piperidin-4-yloxy, 1-methylpiperidin-4-yloxy, 1-benzylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-4-methylpiperazin-1-yl)ethoxy, 3-(4-methylpiperazin-1-yl)propoxy, 2-hydroxy-3-pyrrolidin-1-ylpropoxy, 2-hydroxy-3-piperidinopropoxy, 2-hydroxy-3-morpholinopropoxy, piperidin-4-ylamino, 1-methylpiperidin-4-ylamino, 1-benzylpiperidin-4-ylamino, 2-pyrrolidin-1-ylethylamino, 3-pyrrolidin-1-ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 2-(methylaminoethylaminomethyl, 3-dimethylaminopropylaminomethyl, 3-dimethylamino-2,2-dimethylpropylaminomethyl, 2-(1-methylpyrrolidin-2-ylethyl)aminomethyl, 3-pyrrolidin-1-ylpropylaminomethyl, 2-morpholinoethylaminomethyl, 3-morpholinopropylaminomethyl, 2-piperazin-1-ylethylaminomethyl, 3-(4-methylpiperazin-1-ylpropyl)aminomethyl and 2-pyridylmethoxy; and Q² is 2-pyridyl, 3-pyridyl or 4-pyridyl which bears a substituent selected from pyrrolidin-1-yl, 3-hydroxypyrrolidin-1-yl, 2-hydroxymethylpyrrolidin-1-yl, morpholino, piperidino, 4-hydroxypiperidin-1-yl and piperazin-1-yl;

or a pharmaceutically-acceptable salt thereof.

7. An amide derivative of the Formula I according to claim 1 wherein

R³ is methyl;

m is 0 or m is 1 and R¹ is nitro or amino;

each of p and q is 0;

R⁴ is located at the 3- or 4-position and is selected from diethylaminomethyl, N-(3-dimethylaminopropyl)-N-methylamino, pyrrolidin-1-yl, morpholino, piperidino, piperazin-1-yl, 4-methylpiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, homopiperazin-1-ylmethyl, 4-methylhomopiperazin-1-ylmethyl, 3-aminopyrrolidin-1-ylmethyl, 3-hydroxypyrrolidin-1-ylmethyl, 4-(2-hydroxyethyl)piperazin-1-ylmethyl, pyrrolidin-3-yloxy, N-methylpyrrolidin-3-yloxy, piperidin-4-yloxy, N-methylpiperidin-4-yloxy, N-ethylpiperidin-4-yloxy, N-isopropylpiperidin-4-yloxy, homopiperidin-4-yloxy, N-methylhomopiperidin-4-yloxy, 3-pyrrolidin-1-ylpropylaminomethyl, 2-(1-methylpyrrolidin-2-ylethyl)aminomethyl, 2-morpholinoethylaminomethyl, 3-morpholinopropylaminomethyl, 3-(4-methylpiperazin-1-ylpropyl)aminomethyl, pyrid-2-ylmethoxy, thiazol-4-ylmethoxy and 2-methylthiazol-4-ylmethoxy; and Q² is 2-pyridyl, 3-pyridyl or 4-pyridyl which bears a substituent selected from pyrrolidin-1-yl, 2-hydroxymethylpyrrolidin-1-yl, morpholino and piperidino, and wherein any of the 4 last-named substituents may optionally bear 1 or 2 methyl groups, or Q² is 2- or 4-dibenzofuranyl;

or a pharmaceutically-acceptable salt thereof.

8. An amide derivative of the Formula I according to claim 1 wherein

R³ is methyl;

m is 0 or m is 1 and R¹ is nitro or amino;

each of p and q is 0;

R⁴ is located at the 3- or 4-position and is selected from diethylaminomethyl, N-3-dimethylaminopropyl)-N-methylamino, pyrrolidin-1-yl, morpholino, piperidino, piperazin-1-yl, 4-methylpiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, homopiperazin-1-ylmethyl, 4-methylhomopiperazin-1-ylmethyl, 3-aminopyrrolidin-1-ylmethyl, 3-hydroxypyrrolidin-1-ylmethyl, 4-(2-hydroxyethyl)piperazin-1-ylmethyl, pyrrolidin-3-yloxy, piperidin-4-yloxy, 3-pyrrolidin-1-ylpropylaminomethyl, 2-(1-methylpyrrolidin-2-ylethyl)aminomethyl, 2-morpholinoethylaminomethyl, 3-morpholinopropylaminomethyl, 3-(4-methylpiperazin-1-ylpropyl)aminomethyl or pyrid-2-ylmethoxy; and Q² is 2-pyridyl, 3-pyridyl or 4-pyridyl which bears a substituent selected from pyrrolidin-1-yl, 2-hydroxymethylpyrrolidin-1-yl, morpholino and piperidino;

or a pharmaceutically-acceptable salt thereof.

9. An amide derivative of the Formula I according to claim 1 wherein

R³ is methyl;

each of m, p and q is 0;

R⁴ is located at the 3- or 4-position and is selected from diethylaminomethyl, 4-methylpiperazin-1-yl, morpholinomethyl, piperazin-1-ylmethyl, 4-methylpiperazin-1-ylmethyl, 4-methylhomopiperazin-1-ylmethyl, 3-hydroxypyrrolidin-1-ylmethyl, pyrrolidin-3-yloxy, piperidin-4-yloxy, N-methylpiperidin4-yloxy, N-isopropylpiperidin-4-yloxy, N-methylhomopiperidin-4-yloxy, 2-(N-methylpyrrolidin-2-yl)ethoxy, 3-dimethylamino-2,2- dimethylpropylaminomethyl N-(3-dimethylaminopropyl)-N-methylaminomethyl, 3-morpholinopropylaminomethyl and 2-methylthiazol-4-ylmethoxy; and Q² is 4-pyridyl which bears a substituent selected from morpholino, piperidino, 3-methylpiperidin-1-yl and homopiperidin-1-yl, or Q² is 4-dibenzofuranyl;

or a pharmaceutically-acceptable salt thereof.

10. An amide derivative of the Formula I according to claim 1 selected from:

N-{4-methyl-3-[3-(4-methylpiperazin-1-ylmethyl)benzamido]phenyl}furan-2-carboxamide, N-{4-methyl-3-[3-(4-methylpiperazin-1-ylmethyl)benzamido]phenyl}isoxazole-5-carboxamide, N-[3-4-diethylaminomethylbenzamido)-4-methylphenyl]-2-morpholinopyridine-4-carboxamide, N-{3-[3-(4-methylpiperazin-1-ylmethyl)benzamido]-4-methylphenyl}-2-pyrrolidin-1-ylpyridine-4-carboxamide, N-{3-[3-(4-methylpiperazin-1-ylmethyl)benzamido]-4-methylphenyl}-2-morpholinopyridine-4-carboxamide, N-{3-[3-(4-methylhomopiperazin-1-ylmethyl)benzamido]-4-methylphenyl}-2-morpholinopyridine-4-carboxamide, N-{3-[4-(4-methylhomopiperazin-1-ylmethyl)benzamido]-4-methylphenyl}-2-morpholinopyridine-4-carboxamide, N-[3-(3-piperazin-1-ylmethylbenzamido)-4-methylphenyl]-2-morpholinopyridine-4-carboxamide, N-{3-[4-(3-hydroxypyrrolidin-1-ylmethyl)benzamido]-4-methylphenyl}-2-morpholinopyridine-4-carboxamide, N-{3-[3-(3-pyrrolidin-1-ylpropylaminomethyl)benzamido]-4-methylphenyl}-2-morpholinopyridine-4-carboxamide, N-{3-[4-(3-morpholinopropylaminomethyl)benzamido]-4-methylphenyl}-2-morpholinopyridine-4-carboxamide, N-[3-(3-diethylaminomethylbenzamido)-4-methylphenyl]-2-morpholinopyridine-4-carboxamide, N-[3-(4-diethylaminomethylbenzamido)-4-methylphenyl]-5-morpholinopyridine-3-carboxamide, N-[3-(4-diethylaminomethylbenzamido)-4-methylphenyl]-2-piperidinopyridine-4-carboxamide, N-{3-[3-(4-methylpiperazin-1-ylmethyl)benzamido]-4-methylphenyl}-2-(3-methylpiperidin-1-yl)pyridine-4-carboxamide, N-{3-[3-(4-methylpiperazin-1-ylmethyl)benzamido]-4-methylphenyl}-2-homopiperidin-1-ylpyridine-4-carboxamide, N-[4-methyl-3-(4-morpholinomethylbenzamido)phenyl]-2-morpholinopyridine-4-carboxamide, N-{3-[3-(3-dimethylamino-2,2-dimethylpropylaminomethyl)benzamido]-4-methylphenyl}-2-morpholinopyridine-4-carboxamide, N-{3-[4-(3-dimethylamino-2,2-dimethylpropylaminomethyl)benzamido]-4-methylphenyl}-2-morpholinopyridine-4-carboxamide, N-(3-{4-N-(3-dimethylaminopropyl)-N-methylaminomethyl]benzamido}-4-methylphenyl)-2-morpholinopyridine-4-carboxamide, N-[4-methyl-3-(3-piperidin-4-yloxybenzamido)phenyl]-2-morpholinopyridine-4-carboxamide, N-[4-methyl-3-(3-pyrrolidin-3-yloxybenzamido)phenyl]-2-morpholinopyridine-4-carboxamide, N-{3-[3-(N-methylhomopiperidin-4-yloxy)benzamido]-4-methylphenyl}-2-morpholinopyridine-4-carboxamide, N-(3-{3-[2-(N-methylpyrrolidin-2-yl)ethoxy]benzamido}-4-methylphenyl)-2-morpholinopyridine-4-carboxamide, N-{4-methyl-3-[4-(2-methylthiazol-4-ylmethoxy)benzamido]phenyl}-2-morpholinopyridine-4-carboxamide and N-{3-[3-(4-methylpiperazin-1-ylmethyl)benzamido]-4-methylphenyl}dibenzofuran-4-carboxamide;

or a pharmaceutically-acceptable salt thereof.

11. A process for the preparation of an amide derivative of the Formula I, or a pharmaceutically-acceptable salt or in-vivo-cleavable ester thereof, according to claim 1 which comprises:

(a) reacting an aniline of the Formula II

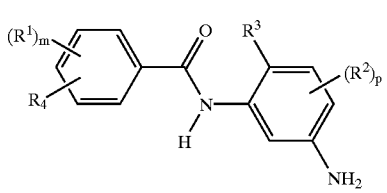

with an acid of the Formula III, or a reactive derivative thereof,

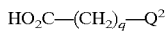

under standard amide bond forming conditions, wherein variable groups are as defined in claim 1 and wherein any functional group is protected if necessary, and:

(i) removing any protecting groups; and
(ii) optionally forming a pharmaceutically-acceptable salt or in-vivo-cleavable ester;

(b) reacting an acid of the Formula V, or an activated derivative thereof,

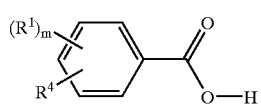

with an aniline of the Formula VII

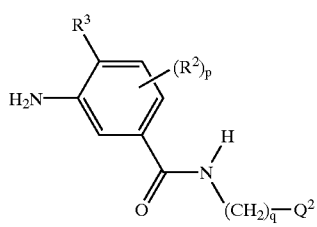

under standard amide bond forming conditions, wherein variable groups are as defined in claim 1 and wherein any functional group is protected, if necessary, and:

(i) removing any protecting groups; and
(ii) optionally forming a pharmaceutically-acceptable salt or in-vivo-cleavable ester;

(c) for the preparation of a compound of the Formula I wherein $R^1$, $R^4$ or a substituent on $Q^2$ is (1–6C)alkoxy or substituted (1–6C)alkoxy, (1–6C)alkylthio, (1–6C)alkylamino, di-[(1–6C)alkyl]amino or substituted (1–6C)alkylamino, the alkylation, conveniently in the presence of a suitable base, of an amide derivative of the Formula I wherein $R^1$, $R^4$ or a substituent on $Q^2$ is hydroxy, mercapto or amino as appropriate;

(d) for the preparation of a compound of the Formula I wherein a substituent on $Q^2$ is amino, (1–6C)alkylamino, di-[(1–6C)alkyl]amino, substituted (1–6C)alkylamino, substituted N-(1–6C)alkyl-(2–6C)alkylamino or a N-linked heterocyclyl group, the reaction, conveniently in the presence of a suitable base, of an amide derivative of the Formula I wherein a substituent on $Q^2$ is a suitable leaving group with an appropriate amine;

(e) for the preparation of a compound of the Formula I wherein $R^1$, $R^4$ or a substituent on $Q^2$ is (1–6C) alkanoylamino or substituted (2–6C)alkanoylamino, the acylation of a compound of the Formula I wherein $R^1$, $R^4$ or a substituent on $Q^2$ is amino;

(f) for the preparation of a compound of the Formula I wherein $R^1$ or a substituent on $Q^2$ is (1–6C) alkanesulphonylamino, the reaction of a compound of the Formula I wherein $R^1$ or a substituent on $Q^2$ is amino with a (1–6C)alkanesulphonic acid, or an activated derivative thereof; or (g) for the preparation of a compound of the Formula I wherein $R^1$ or a substituent on $Q^2$ is carboxy, carboxy-(1–6C)alkyl, carboxy-(1–6C)alkoxy, carboxy-(1–6C)alkylamino, N-(1–6C)alkyl-carboxy-(1–6C)alkylamino or carboxy-(2–6C)alkanoylamino, the cleavage of a compound of the Formula I wherein $R^1$ or a substituent on $Q^2$ is (1–6C)alkoxycarbonyl, (1–6C)alkoxycarbonyl-(1–6C)alkyl, (1–6C)alkoxycarbonyl-(1–6C)alkoxy, (1–6C) alkoxycarbonyl-(1–6C)alkylamino, N-(1–6C)alkyl-(1–6C)alkoxycarbonyl-(1–6C)alkylamino or (1–6C) alkoxycarbonyl-(2–6C)alkanoylamino as appropriate.

12. A pharmaceutical composition which comprises an amide derivative of the Formula I, or a pharmaceutically-acceptable salt or in-vivo-cleavable ester thereof, according to claim 1 in association with a pharmaceutically-acceptable diluent or carrier.

13. A method of treating a disease or medical condition mediated by one or more cytokines, which comprises administering to a warm-blooded animal in need thereof an effective amount of an amide derivative of the formula I as claimed in claim 1.

* * * * *